(12) United States Patent
Lee

(10) Patent No.: US 10,527,592 B2
(45) Date of Patent: Jan. 7, 2020

(54) ULTRASONIC PROBE, ULTRASONIC IMAGING APPARATUS INCLUDING THE SAME, AND METHOD FOR CONTROLLING THE ULTRASONIC IMAGING APPARATUS

(71) Applicant: SAMSUNG MEDISON CO., LTD., Hongcheon-gun, Gangwon-do (KR)

(72) Inventor: Hong-Gyo Lee, Seoul (KR)

(73) Assignee: SAMSUNG MEDISON CO., LTD., Hongcheon-gun, Gangwon-do (KR)

( * ) Notice: Subject to any disclaimer, the term of this patent is extended or adjusted under 35 U.S.C. 154(b) by 124 days.

(21) Appl. No.: 15/254,733

(22) Filed: Sep. 1, 2016

(65) Prior Publication Data
US 2017/0074837 A1 Mar. 16, 2017

(30) Foreign Application Priority Data

Sep. 16, 2015 (KR) .......................... 10-2015-0130797
Apr. 15, 2016 (KR) .......................... 10-2016-0046378

(51) Int. Cl.
*G01N 29/52* (2006.01)
*G01N 29/06* (2006.01)
(Continued)

(52) U.S. Cl.
CPC .............. *G01N 29/52* (2013.01); *A61B 8/00* (2013.01); *A61B 8/08* (2013.01); *A61B 8/4444* (2013.01);
(Continued)

(58) Field of Classification Search
CPC ...... G01N 29/52; G01N 29/0654; A61B 8/00; A61B 8/08; A61B 8/4444; A61B 8/54;
(Continued)

(56) References Cited

U.S. PATENT DOCUMENTS 4,542,746 A * 9/1985 Takamizawa ........ G10K 11/346
  348/163
5,590,658 A * 1/1997 Chiang .................. A61B 8/463
  600/447
(Continued)

FOREIGN PATENT DOCUMENTS

EP    0087318 A2    8/1983
EP    0702247 A2    3/1996
(Continued)

OTHER PUBLICATIONS

European Office Action dated Jan. 2, 2018 issued in European Patent Application No. 16186772.6.
(Continued)

*Primary Examiner* — Helen C Kwok
(74) *Attorney, Agent, or Firm* — Morgan, Lewis & Bockius LLP

(57) ABSTRACT

An ultrasonic probe, an ultrasonic imaging apparatus including the same, and a method for controlling the same are disclosed, which relate to a method for changing a pulse signal received by an ultrasonic probe by controlling a switching element mounted to an ultrasonic probe during pulse inversion harmonic imaging. The ultrasonic probe includes: a transducer array configured to transmit and receive an ultrasonic signal; a printed circuit board (PCB) electrically connected to the transducer array so as to transmit a pulse signal received from a main body of an ultrasonic imaging apparatus to the transducer array; and a switching circuit configured to change a waveform of the pulse signal received by the PCB and transmitted to the transducer array.

20 Claims, 37 Drawing Sheets

(51) Int. Cl.
*A61B 8/08* (2006.01)
*A61B 8/00* (2006.01)
*A61B 8/14* (2006.01)
*A61B 90/00* (2016.01)
*B06B 1/02* (2006.01)

(52) U.S. Cl.
CPC ............... *A61B 8/54* (2013.01); *A61B 90/36* (2016.02); *B06B 1/0215* (2013.01); *G01N 29/0654* (2013.01); *A61B 8/145* (2013.01); *A61B 8/4405* (2013.01); *A61B 8/4494* (2013.01); *A61B 2562/166* (2013.01); *G01N 2291/017* (2013.01); *G01N 2291/106* (2013.01)

(58) Field of Classification Search
CPC ..... A61B 8/145; A61B 8/4405; A61B 8/4494; A61B 8/4483
See application file for complete search history.

(56) References Cited

U.S. PATENT DOCUMENTS

| | | | | |
|---|---|---|---|---|
| 5,722,412 A * | 3/1998 | Pflugrath | ................ | A61B 8/00 600/441 |
| 6,050,945 A * | 4/2000 | Peterson | ................ | B06B 1/0215 600/443 |
| 6,095,980 A * | 8/2000 | Burns | ................ | A61B 8/481 600/453 |
| 6,126,602 A * | 10/2000 | Savord | ................ | G01S 7/52046 600/443 |
| 6,142,946 A * | 11/2000 | Hwang | ................ | A61B 8/00 600/459 |
| 6,491,634 B1 * | 12/2002 | Leavitt | ................ | G01N 29/06 600/447 |
| 6,994,674 B2 * | 2/2006 | Sheljaskow | ........... | B06B 1/0622 600/459 |
| 7,105,981 B2 * | 9/2006 | Lazenby | ................ | G01S 15/895 310/317 |
| 7,115,094 B2 * | 10/2006 | Azuma | ................ | A61B 8/00 600/459 |
| 7,686,766 B2 * | 3/2010 | Quistgaard | .......... | A61B 5/0402 600/459 |
| 7,745,976 B2 * | 6/2010 | Cerofolini | ................ | A61B 8/00 310/334 |
| 8,345,508 B2 * | 1/2013 | Wodnicki | ............ | B23K 1/0016 367/7 |
| 9,202,457 B2 * | 12/2015 | Song | ................ | G10K 11/346 |
| 9,639,056 B2 * | 5/2017 | Falter | ................ | G03H 3/00 |
| 2004/0002435 A1 * | 1/2004 | Petersen | ................ | B06B 1/0622 510/314 |
| 2005/0096545 A1 * | 5/2005 | Haider | ................ | G01S 7/52079 600/447 |
| 2005/0203391 A1 * | 9/2005 | Phelps | ................ | G01S 7/52019 600/437 |
| 2007/0016026 A1 * | 1/2007 | Thomenius | ........... | G01S 7/5208 600/437 |
| 2007/0106159 A1 | 5/2007 | Iwama | | |
| 2008/0264171 A1 * | 10/2008 | Wodnicki | ................ | A61B 8/00 73/618 |
| 2010/0228128 A1 * | 9/2010 | Lee | ................ | A61B 8/00 600/443 |
| 2011/0101824 A1 * | 5/2011 | Nishigaki | ................ | B06B 1/0215 310/317 |
| 2011/0184289 A1 * | 7/2011 | Oshiki | ................ | B06B 1/023 600/443 |
| 2013/0310689 A1 * | 11/2013 | Nishigaki | ............ | A61B 8/4483 600/437 |
| 2014/0005048 A1 | 1/2014 | Gutsche et al. | | |

FOREIGN PATENT DOCUMENTS

| | | |
|---|---|---|
| EP | 2294981 A1 | 3/2011 |
| JP | 2011050571 A | 3/2011 |

OTHER PUBLICATIONS

Extended European Search Report dated Feb. 1, 2017 issued in European Patent Application No. 16186772.6.

* cited by examiner

FIG.2
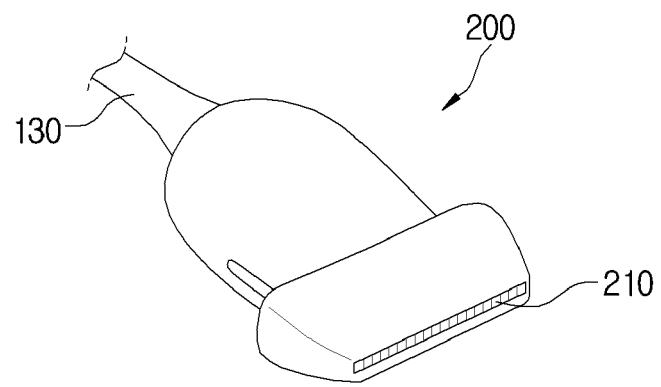
(a)
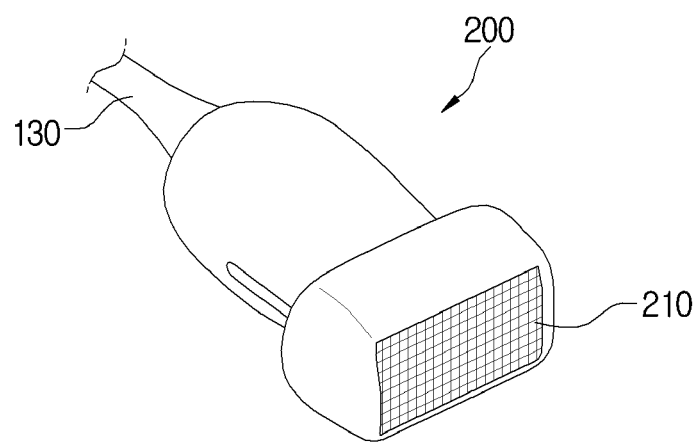
(b)

FIG.4
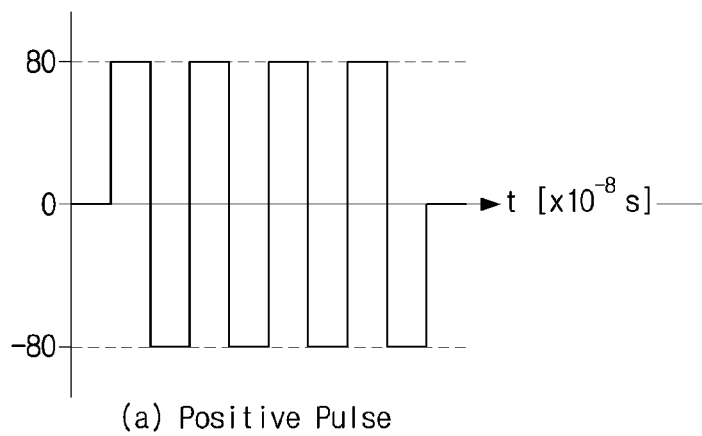
(a) Positive Pulse
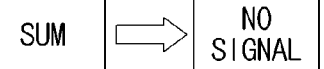
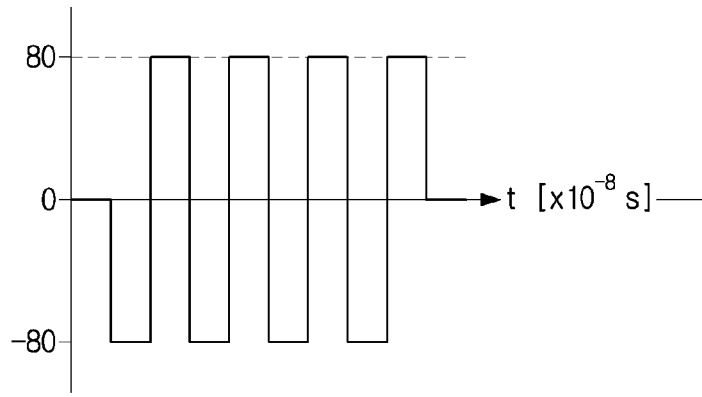
(b) Negative Pulse

ULTRASONIC PROBE, ULTRASONIC IMAGING APPARATUS INCLUDING THE SAME, AND METHOD FOR CONTROLLING THE ULTRASONIC IMAGING APPARATUS

CROSS-REFERENCE TO RELATED APPLICATION

This application claims the benefit of Korean Patent Application Nos. 10-2015-0130797 and 10-2016-0046378, respectively filed on Sep. 16, 2015 and Apr. 15, 2016 in the Korean Intellectual Property Office, the disclosure of which is incorporated herein by reference.

BACKGROUND

1. Field

Embodiments of the present disclosure relate to an ultrasonic probe, an ultrasonic imaging apparatus including the same, and a method for controlling the same, and more particularly to a method for changing a pulse signal received by an ultrasonic probe by controlling a switching element mounted to an ultrasonic probe during pulse inversion harmonic imaging.

2. Description of the Related Art

An ultrasonic imaging apparatus applies an ultrasonic signal generated by a transducer of an ultrasonic probe from the surface of an object (for example, a human body) to a target site of the inside of the body of the object, and non-invasively acquires tomograms of soft tissues or images regarding blood flow upon receiving reflected ultrasonic signals (ultrasonic echo signals), such that the ultrasonic imaging apparatus may be used for medical purposes, for example, acquisition of images regarding the interior of the object, detection of foreign materials, injury measurement, etc.

The ultrasonic imaging apparatus has compact size and low price, displays a diagnostic image in real time, as compared to other image diagnostic apparatuses, for example, an X-ray diagnostic apparatus, an X-ray computed tomography (CT) scanner, a magnetic resonance imaging (MRI) apparatus, and a nuclear medical diagnostic apparatus. In addition, since the ultrasonic imaging apparatus does not cause radiation exposure, the ultrasonic imaging apparatus is inherently safe. Accordingly, the ultrasonic imaging apparatus has been widely used in various fields along with other image diagnostic apparatuses.

The ultrasonic imaging apparatus includes an ultrasonic probe which emits ultrasonic signals to the object and receives echo ultrasonic signals reflected from the object, such that it can acquire images regarding the interior of the object. In order to emit ultrasonic signals to the interior of the human body, a transducer array to convert an electrical signal into an ultrasonic signal and vice versa may be used. The transducer array may include a plurality of transducer elements.

Meanwhile, pulse inversion harmonic imaging may be used for ultrasonic diagnosis, and the pulse inversion harmonic imaging is an ultrasonic diagnostic technology for effectively detecting harmonic signals or non-linear signals.

SUMMARY

Therefore, it is an aspect of the present disclosure to provide a technology which inverts a pulse signal received by an ultrasonic probe upon receiving a control signal from a switching element mounted to the ultrasonic probe, such that occurrence of residual signals caused by reception of an asymmetrical inversion signal is prevented, resulting in improvement of image resolution. It is another aspect of the present disclosure to provide a technology which blocks a pulse signal by controlling a switching element so as to selectively use only a transducer element used for transmission of the pulse signal, such that occurrence of signals caused by an abnormal signal is prevented, resulting in improvement of user stability. It is another aspect of the present disclosure to provide a technology which controls a transducer element unused in transmission/reception (Tx/Rx) of a pulse signal to be grounded, resulting in improvement of resolution of an ultrasonic image. It is another aspect of the present disclosure to provide a technology for stabilizing transducer elements after transmission of a pulse signal during pulse signal transmission, resulting in improvement of a simultaneous mode image.

Additional aspects of the invention will be set forth in part in the description which follows and, in part, will be obvious from the description, or may be learned by practice of the invention.

In accordance with one aspect of the present disclosure, an ultrasonic probe includes: a transducer array configured to transmit and receive an ultrasonic signal; a printed circuit board (PCB) electrically connected to the transducer array so as to transmit a pulse signal received from a main body of an ultrasonic imaging apparatus to the transducer array; and a switching circuit configured to change a waveform of the pulse signal received by the PCB and transmitted to the transducer array.

The switching circuit may include a first switching element and a second switching element, wherein the first switching element is connected to any one of a pulse signal reception terminal, a ground terminal, and a predetermined terminal, and the second switching element is connected to any one of the pulse signal reception terminal, the ground terminal, and the predetermined terminal.

The transducer array may include a plurality of transducer elements, and the switching circuit may include a plurality of switching circuits corresponding to respective transducer elements.

If the first switching element is connected to the pulse signal reception terminal and the second switching element is connected to the ground terminal, the transducer element may transmit an ultrasonic signal having the same waveform as the pulse signal received by the PCB.

If the first switching element is connected to the ground terminal and the second switching element is connected to the pulse signal reception terminal, the transducer element may receive an ultrasonic signal corresponding to an inversion waveform of the pulse signal received by the PCB.

The transducer element may transmit no ultrasonic signal when each of the first switching element and the second switching element are connected to the pulse signal reception terminal, the ground terminal, and the predetermined terminal.

Among the plurality of switching elements corresponding to the respective transducer elements, one switching circuit in which each of the first switching element and the second switching element is connected to any one of the pulse signal reception terminal, the ground terminal, and the predetermined terminal may be configured to prevent the pulse signal received by the PCB from being applied to the transducer element.

The ultrasonic probe may further include: a control board configured to control the first switching element to be connected to the pulse signal reception terminal, the ground terminal, and the predetermined terminal, and configured to control the second switching element to be connected to the pulse signal reception terminal, the ground terminal, and the predetermined terminal.

The printed circuit board (PCB) may be configured to transmit the pulse signal received from the transducer array to a main body of the ultrasonic imaging apparatus.

In accordance with another aspect of the present disclosure, an ultrasonic imaging apparatus includes: a pulse transmitter configured to generate a pulse signal and transmit the generated pulse signal; an ultrasonic probe which includes a printed circuit board (PCB) electrically connected to the transducer array so as to transmit the pulse signal received from the pulse transmitter to the transducer array, and a switching circuit configured to change a waveform of the pulse signal received by the PCB and transmitted to the transducer array; and a processor configured to control the switching circuit for changing a waveform of the pulse signal generated by the pulse transmitter and transmitted to the PCB.

The ultrasonic probe may include a switching circuit implemented as a first switching element and a second switching element, wherein the first switching element is connected to any one of a pulse signal reception terminal, a ground terminal, and a predetermined terminal, and the second switching element is connected to any one of the pulse signal reception terminal, the ground terminal, and the predetermined terminal.

The transducer array may include a plurality of transducer elements, and the switching circuit may include a plurality of switching circuits corresponding to respective transducer elements.

The processor may connect the first switching element to the pulse signal reception terminal, may connect the second switching element to the ground terminal, and may thus control transmission of an ultrasonic signal having the same waveform as the pulse signal received by the PCB.

The processor may connect the first switching element to the ground terminal, may connect the second switching element to the pulse signal reception terminal, and may thus control transmission of an ultrasonic signal having an inversion waveform of the pulse signal received by the pulse signal received by the PCB.

The processor may connect each of the first switching element and the second switching element to any one of the pulse signal reception terminal, the ground terminal, and the predetermined terminal, such that no ultrasonic signal is transmitted.

Among the plurality of switching elements corresponding to the respective transducer elements, one switching circuit in which each of the first switching element and the second switching element is connected to any one of the pulse signal reception terminal, the ground terminal, and the predetermined terminal may be configured to prevent the pulse signal received by the PCB from being applied to the transducer element.

The printed circuit board (PCB) may be configured to transmit the pulse signal received from the transducer array to a main body of the ultrasonic imaging apparatus.

In accordance with another aspect of the present disclosure, a method for controlling an ultrasonic imaging apparatus equipped with an ultrasonic probe including a switching circuit implemented as a first switching element and a second switching element includes: transmitting a pulse signal to the ultrasonic probe; and changing a waveform of the pulse signal received by the ultrasonic probe.

The changing the pulse signal received by the ultrasonic probe may include: connecting the first switching element to any one of a pulse signal reception terminal, a ground terminal, and a predetermined terminal; connecting the second switching element to any one of the pulse signal reception terminal, the ground terminal, and the predetermined terminal; and thus changing a waveform of the pulse signal.

The changing the pulse signal received by the ultrasonic probe may include: connecting the first switching element to the pulse signal reception terminal; connecting the second switching element to the ground terminal; and thus transmitting an ultrasonic signal having the same waveform as the pulse signal received by the PCB.

The changing the pulse signal received by the ultrasonic probe may include: connecting the first switching element to the ground terminal; connecting the second switching element to the pulse signal reception terminal; and thus transmitting an ultrasonic signal having an inversion waveform of the pulse signal received by the pulse signal received by the PCB.

The changing the pulse signal received by the ultrasonic probe may include: connecting each of the first switching element and the second switching element to any one of the pulse signal reception terminal, the ground terminal, and the predetermined terminal, resulting in transmission of no ultrasonic signal.

In the changing the pulse signal received by the ultrasonic probe, from among the plurality of switching elements corresponding to the respective transducer elements, one switching circuit in which each of the first switching element and the second switching element is connected to any one of the pulse signal reception terminal, the ground terminal, and the predetermined terminal may prevent the pulse signal received by the PCB from being applied to the transducer element.

In accordance with another aspect of the present disclosure, an ultrasonic probe includes: a transducer transmission element configured to transmit an ultrasonic signal; a transducer reception element configured to receive an ultrasonic signal; a printed circuit board (PCB) electrically connected to the transducer transmission element and the transducer reception element, configured to transmit a pulse signal received from a main body of an ultrasonic imaging apparatus to the transducer transmission element, and configured to transmit a pulse signal received from the transducer reception element to the main body of the ultrasonic imaging apparatus; and a switching circuit configured to change not only a waveform of the pulse signal received by the PCB and transmitted to the transducer transmission element, but also a waveform of the pulse signal received by the transducer reception element and transmitted to the PCB.

The switching circuit may include: a first switching element and a second switching element, wherein the first switching element is connected to any one of a pulse signal reception terminal, a ground terminal, and a predetermined terminal, and the second switching element is connected to any one of the pulse signal reception terminal, the ground terminal, and the predetermined terminal.

BRIEF DESCRIPTION OF THE DRAWINGS

These and/or other aspects of the invention will become apparent and more readily appreciated from the following description of the embodiments, taken in conjunction with the accompanying drawings of which:

FIG. 2 is a view illustrating an ultrasonic probe including a one-dimensional (1D) transducer array and a two-dimensional (2D) transducer array according to an embodiment of the present disclosure.

FIG. 4 is a graph illustrating waveforms of pulse signals used for pulse inversion harmonic imaging of ultrasonic imaging diagnosis.

DETAILED DESCRIPTION

Figure 1:
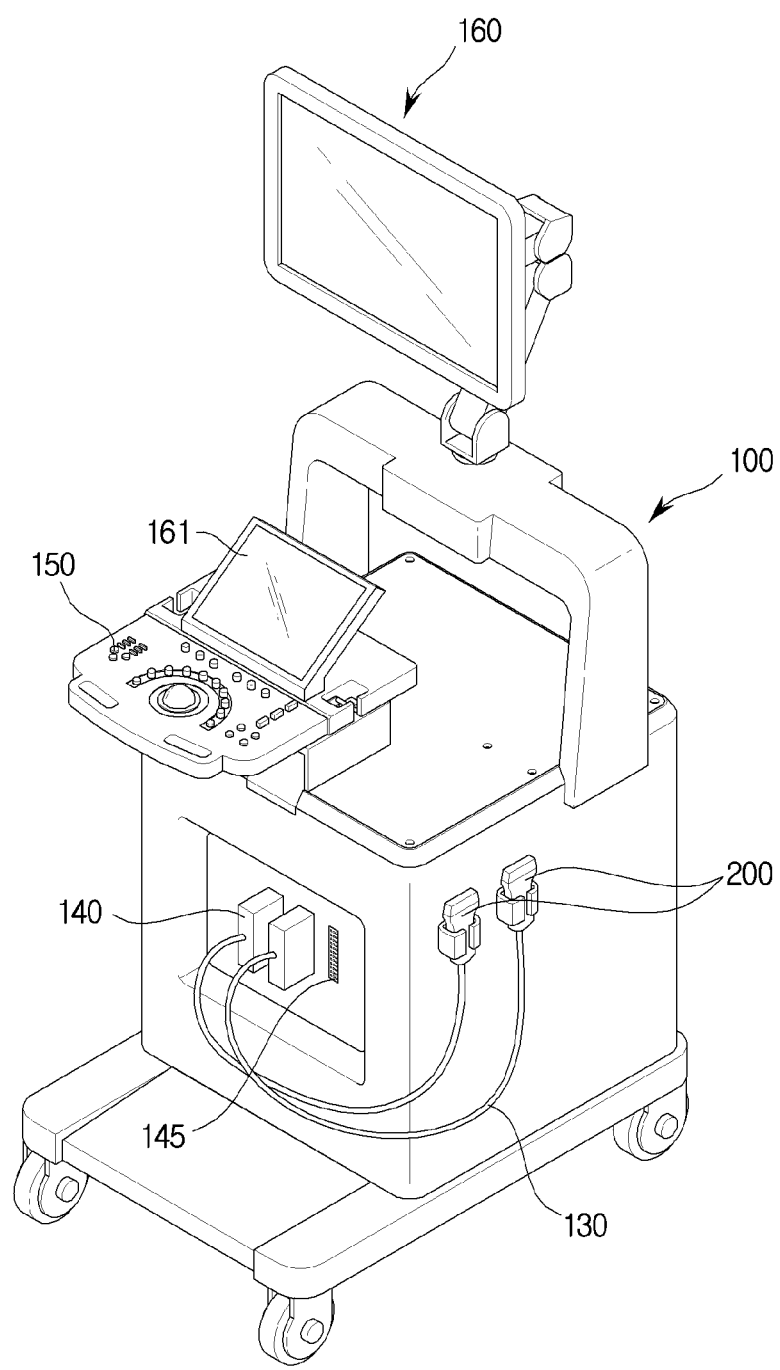
FIG. 1 is a perspective view illustrating the external appearance of an ultrasonic imaging apparatus according to an embodiment of the present disclosure.

Advantages and features of the present disclosure and a method of achieving the advantages and features of the present disclosure will be clearly understood from embodiments described hereinafter in conjunction with the accompanying drawings. Reference will now be made in detail to the embodiments of the present disclosure, examples of which are illustrated in the accompanying drawings, wherein like reference numerals refer to like elements throughout.

The target object may indicate organs of a human body, animals, or some parts thereof. For example, the target object may include organs of the human body (e.g., a liver, a heart, a uterus, a brain, a breast, an abdomen) or blood vessels. The term "users" may indicate medical experts, for example, doctors, nurses, medical technologists, medical image specialists, ultrasonic inspectors, etc. In addition, the term "users" may also indicate technicians who repair medical devices. However, the scope or spirit of the present disclosure is not limited thereto.

The term "ultrasonic image" used in the entire specification of the present disclosure may denote images regarding the target object to be imaged using ultrasonic signals, and may also denote images regarding the target object using various diagnostic devices, for example, an X-ray diagnostic device, an X-ray CT scanner, an MRI (magnetic resonance imaging) device, and a nuclear medicine diagnostic device. In addition, the diagnostic devices to which the ultrasonic imaging apparatus and the method for controlling the same according to embodiments of the present disclosure can be applied may also be applied to an X-ray imaging device, an X-ray fluoroscopy device, a computed tomography (CT) scanner, a magnetic resonance imaging (MRI) device, a positron emission tomography (PET) device, and an ultrasonic imaging device. Although the embodiments will exemplarily disclose the ultrasonic imaging apparatus for convenience of description and better understanding of the present disclosure, it should be noted that the scope or spirit of the present disclosure is not limited thereto.

Throughout the specification of the present disclosure, if it is assumed that a certain part includes a certain component, the term 'comprising or including' means that a corresponding component may further include other components unless a specific meaning opposed to the corresponding component is written. In addition, another term '... circuit', '... portion', '... part', '... module' or the like means a unit for processing at least one function or operation, and this unit may be implemented by hardware, software, or a combination thereof.

The term "switching element" used in the entire specification of the present disclosure may denote a wiring element for connecting or blocking a current of an electronic device. The switching element may include a transistor for connecting the current according to a control signal, and may include a Bipolar Junction Transistor (BJT), a field effect transistor (FET), a High Voltage MUX (HVMUX), and a relay without being limited thereto.

However, for example, if the switching element operates as the FET, it is obvious to those skilled in the art that the switching element includes a gate terminal, a drain terminal, and a source terminal, the drain terminal may function as a source terminal according to an input signal, and the source terminal may function as a drain terminal.

In addition, the switching element may be classified into a low-voltage switching element (LN) operated at a low voltage and a high-voltage switching element (HN) operated at a high voltage according to operation voltages. Specifically, the high-voltage switching element (HN) may be configured to endure a high voltage even when high voltage is applied to a drain terminal thereof. Generally, the HNs have been widely used in various power elements.

The HNs may include a Double-diffused MOSFET (DMOSFET), an Insulated Gate Bipolar Transistor (IGBT), an Extended Drain MOSFET (EDMOSFET), a Lateral Double-diffused MOSFET (LDMOSFET), etc. without being limited thereto.

An ultrasonic probe, an ultrasonic imaging apparatus including the same, and a method for controlling ultrasonic imaging apparatus according to embodiments of the present disclosure will hereinafter be described with reference to the attached drawings. Wherever possible, the same reference numbers will be used throughout the drawings to refer to the same or like parts. In the following description, known functions or structures, which may confuse the substance of the present disclosure, are not explained. It will be understood that, although the terms first, second, etc. may be used herein to describe various elements, components, regions, layers and/or sections, these elements, components, regions, layers and/or sections should not be limited by these terms.

FIG. 1 is a perspective view illustrating the external appearance of an ultrasonic imaging apparatus according to an embodiment of the present disclosure.

Referring to FIG. 1, the ultrasonic imaging apparatus may include a main body 100, an input module 150 connected to the main body 100, a display 160, a sub-display panel 161, and an ultrasonic probe 200.

A plurality of casters (not shown) for mobility of the ultrasonic imaging apparatus may be located below the main body 100 of the ultrasonic imaging apparatus. The casters may fix the ultrasonic imaging apparatus to a specific place, and may move the ultrasonic imaging apparatus in a specific direction. This ultrasonic imaging apparatus may be referred to as a cart-type ultrasonic imaging apparatus.

Alternatively, differently from FIG. 1, the ultrasonic imaging apparatus may be a mobile (or portable) ultrasonic imaging apparatus that is capable of being carried by the user. In this case, the mobile ultrasonic imaging apparatus may not include casters therein. The mobile ultrasonic imaging apparatus may be implemented as any one of a picture archiving communication system (PACS) viewer, a smartphone, a laptop computer, a personal digital assistant (PDA), a tablet, etc., without being limited thereto.

The ultrasonic probe 200 configured to contact the skin of a target object may transmit and receive ultrasonic signals to or from the target object. In more detail, the ultrasonic probe 200 may generate ultrasonic signals according to input pulses, may transmit the generated ultrasonic signals to the inside of the target object, and may receive echo ultrasonic signals reflected from a specific part of the target object.

The ultrasonic imaging apparatus 100 may transmit ultrasonic signals to the ultrasonic probe 200, may receive echo ultrasonic signals from the ultrasonic probe 200, and may thus generate an ultrasonic image on the basis of the received resultant signals.

The ultrasonic image may be provided to a user through the display 160, and the user may visually recognize the received ultrasonic image of the interior part of the target object, such that the user can diagnose the target object (i.e., the patient).

The display 160 may also display various user interfaces (UIs) associated with control of the ultrasonic imaging apparatus. The user may confirm the UI received through the display 160, and may input either a control command for the ultrasonic imaging apparatus or a control command for one constituent element of the ultrasonic imaging apparatus through the input module 150.

In addition, the display 160 may display ultrasonic images obtained through the ultrasonic diagnosis procedure. The display 160 may be implemented as a Cathode Ray Tube (CRT), a Liquid Crystal Display (LCD), etc., or may also be implemented as any one of examples well known to those skilled in the art. The display unit 160 may also provide 2D images and 3D images as necessary.

The user may input a control command for the ultrasonic imaging apparatus by touching the display 160, and may also input a touch command for setting a user region of interest (to be observed or diagnosed by the user) in an ultrasonic image of the target object.

The display 160 may include a touch panel to receive a user's touch input signal. The touch panel may be implemented as any one of a Liquid Crystal Display (LCD) panel, a Light Emitting Diode (LED) panel, an Organic Light Emitting Diode (OLED) panel, etc.

The sub display panel 161 may display various user interfaces (UIs) associated with control of the ultrasonic imaging apparatus in the same manner as in the display 160, and the user may confirm the UI received through the sub display panel 161, and may input either a control command of the ultrasonic imaging apparatus or a control command of one constituent element of the ultrasonic imaging apparatus through the input module 150 or a touchscreen of the sub display panel 161.

The sub display panel 161 may include a touch panel to receive a user's touch input command. The touch panel may be implemented as any one of a Liquid Crystal Display (LCD) panel, a Light Emitting Diode (LED) panel, an Organic Light Emitting Diode (OLED) panel, etc.

Although the ultrasonic imaging apparatus 100 illustrated in FIG. 1 includes the display 160 and the sub display panel 161, it should be noted that the sub display panel 161 may be omitted for convenience of description. In this case, the application or menu displayed through the sub display panel 161 may be displayed on the display 160.

Figure 7:
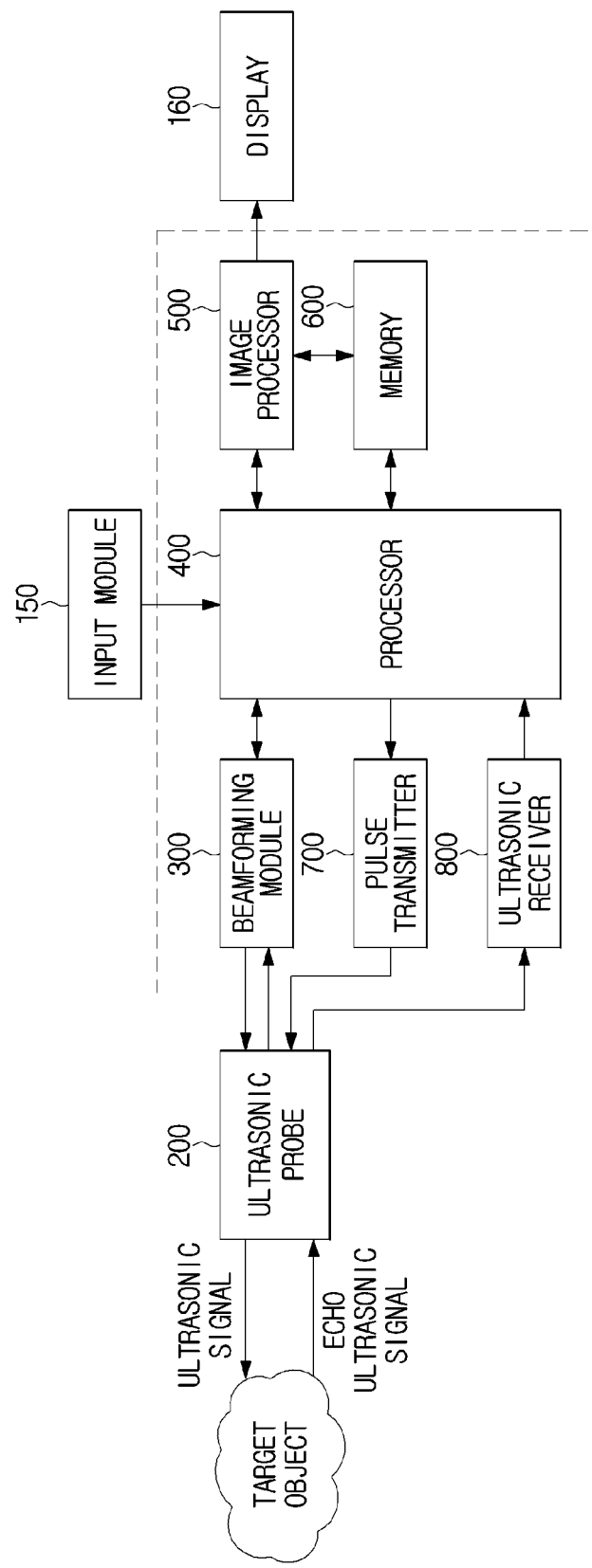
FIG. 7 is a block diagram illustrating an ultrasonic imaging apparatus including an ultrasonic probe according to an embodiment of the present disclosure.

In the meantime, an image processor 500 for converting echo ultrasonic signals received by the ultrasonic probe 200 into an ultrasonic image may be contained in the main body of the ultrasonic imaging apparatus 100, as illustrated in FIG. 7. The image processor 500 may be implemented as hardware such as a microprocessor, or may also be implemented as software running on hardware.

The image processor 500 may form an ultrasonic image through scan conversion of echo ultrasonic signals. The ultrasonic image may include not only a grayscale image and a three-dimensional (3D) image, that are obtained by scanning the target object in an amplitude (A) mode, a brightness (B) mode, and a motion (M) mode, but also a Doppler image for indicating a moving object using the Doppler effect. The Doppler image may include a blood-flow Doppler image (also called a color Doppler image) indicating blood flow, a tissue Doppler image indicating the movement of tissues, and a spectrum Doppler image for displaying the moving speed of the target object in a waveform format.

In order to generate a B-mode image, the image processor 500 may extract a B-mode component from echo ultrasonic data received by the ultrasonic probe 200, and process the extracted B-mode component. The image generator 500 may generate an ultrasonic image in which strength of the echo ultrasonic signal is represented by brightness on the basis of the B-mode component extracted by the B-mode processor.

The image processor 500 may extract the Doppler component from echo ultrasonic data, and the image processor 500 may generate a Doppler image in which movement of the target object is represented by colors or waveforms on the basis of the extracted Doppler component.

In addition, the image processor 500 may perform rendering of obtained volume data, such that it may generate a 3D ultrasonic image or may generate an elastic image for displaying the modification degree of the target object in response to pressure. Furthermore, the image processor 500 may also display various additional information (e.g., text or graphics) on the ultrasonic image.

The generated ultrasonic image may be stored in the memory located inside or outside the main body. In addition, the ultrasonic image may also be stored in a web-based storage or cloud server configured to perform a storage function of the memory over the Internet.

The input module 150 may receive commands regarding the operations of the ultrasonic imaging apparatus 100. For example, the input module 150 may receive commands for selecting modes (e.g., A mode, B mode, M mode, Doppler image mode, etc.). Furthermore, the input module 150 may receive commands to select one of ultrasonic diagnosis start, diagnosis part selection, diagnosis category selection, and mode selection of the output ultrasonic images, from the user.

The user may select a pulse inversion harmonic imaging ultrasonic diagnostic mode through the input module 150, and may input the pulse signal to be applied to the ultrasonic probe. In addition, the user may input a command for controlling the first switching element and the second switching element of the switching circuit contained in the ultrasonic probe through the input module 150. As shown in FIG. 1, the input module 150 may be located at the top of the main body 100. In this case, the input module 150 may include at least one of a switch, a key, a wheel, a joystick, a track ball, and a knob.

The commands input through the input module 150 may be transmitted to the main body of the ultrasonic imaging apparatus 100 through wired communication or wireless communication.

The ultrasonic probe 200 may be connected to one end of the cable 130, and the other end of the cable 130 may be connected to a male connector 140. The male connector 140 connected to the other end of the cable 140 may be physically connected to a female connector 145 of the main body 100.

As described above, one ultrasonic probe 200 may be connected to one main body 100, and several ultrasonic probes 200 may also be connected to one main body 100 in a similar way to the above example. For this purpose, several female connectors may be mounted to the main body 100. As can be seen from FIG. 1, two ultrasonic probes 200 are connected to one main body 100.

Alternatively, differently from FIG. 1, the ultrasonic probe 200 may be wirelessly connected to the main body 100. In this case, the ultrasonic probe 200 may wirelessly transmit an echo ultrasonic signal corresponding to echo ultrasonic waves received from the target object to the main body 100.

The ultrasonic probe 200 may contact the skin of the target object, and thus transmit and receive ultrasonic signals to and from the target object. In more detail, the ultrasonic probe 200 may emit ultrasonic waves to the target object according to ultrasonic signals corresponding to electric signals received from the main body 100, may collect echo ultrasonic waves reflected from a specific part contained in the target object, and may transmit echo ultrasonic signals corresponding to the collected echo ultrasonic waves to the main body 100.

For this purpose, the ultrasonic probe 200 may include a transducer and a multiplexer (MUX) circuit. The transducer may include several transducer elements which vibrate to convert an electric signal into an ultrasonic signal and vice versa. The transducer elements may be arranged over one surface of the housing of the ultrasonic probe. In more detail, several transducers may be arranged in parallel to one or more apertures in a manner that ultrasonic signals can be transmitted and received through the apertures mounted to one surface of the housing.

The ultrasonic imaging apparatus 100 may further include a communication module. The communication module may communicate with the external device or the server over a wired or wireless network. The communication module may communicate with a hospital server or other in-hospital medical machines connected through a Picture Archiving and Communication System (PACS). In addition, the communication module may perform data communication according to medical digital imaging and Digital Imaging and Communications in Medicine (DICOM) standard.

The communication module may transmit and receive diagnostic data (e.g., ultrasonic images, echo ultrasonic signals, Doppler data, etc. of the target object) of the target object over the network, and may also transmit and receive medical images captured by other medical machines such as CT, MRI, X-ray, etc. Furthermore, the communication module may receive information regarding diagnosis history or medical treatment schedule of the patient from the server, and may use the received information to diagnose the target object. The communication module may communicate with the server or medical device of the hospital, and may communicate with a mobile phone of the doctor or patient as necessary.

The communication module may communicate with the server, the medical device, or the mobile phone over a wired or wireless network. The communication module may include one or more constituent elements capable of communicating with the external device. For example, the communication module may include a local area network (LAN) communication module, a wired communication module, and a mobile communication module. The LAN communication module may denote a communication module for short-range communication within a predetermined distance. The LAN communication technology according to one embodiment may include Wireless LAN, Wi-Fi, Bluetooth, ZigBee, Wi-Fi Direct (WFD), Ultra wideband (UWB), Infrared Data Association (IrDA), Bluetooth Low Energy (BLE), Near Field Communication (NFC), etc. without being limited thereto.

The wired communication network may denote a communication module using electrical signals or optical signals. The wired communication technology according to one embodiment may include a twisted-pair cable, a coaxial cable, an optical fiber cable, or an Ethernet cable.

The mobile communication module may transmit and receive radio frequency (RF) signals to and from at least one of a base station (BS), an external terminal (such as a user equipment UE), and a server over a wireless communication network. In this case, the RF signal may include a voice call signal, a video call signal, or various types of data based on text/multimedia message transmission/reception (Tx/Rx).

Figure 3:
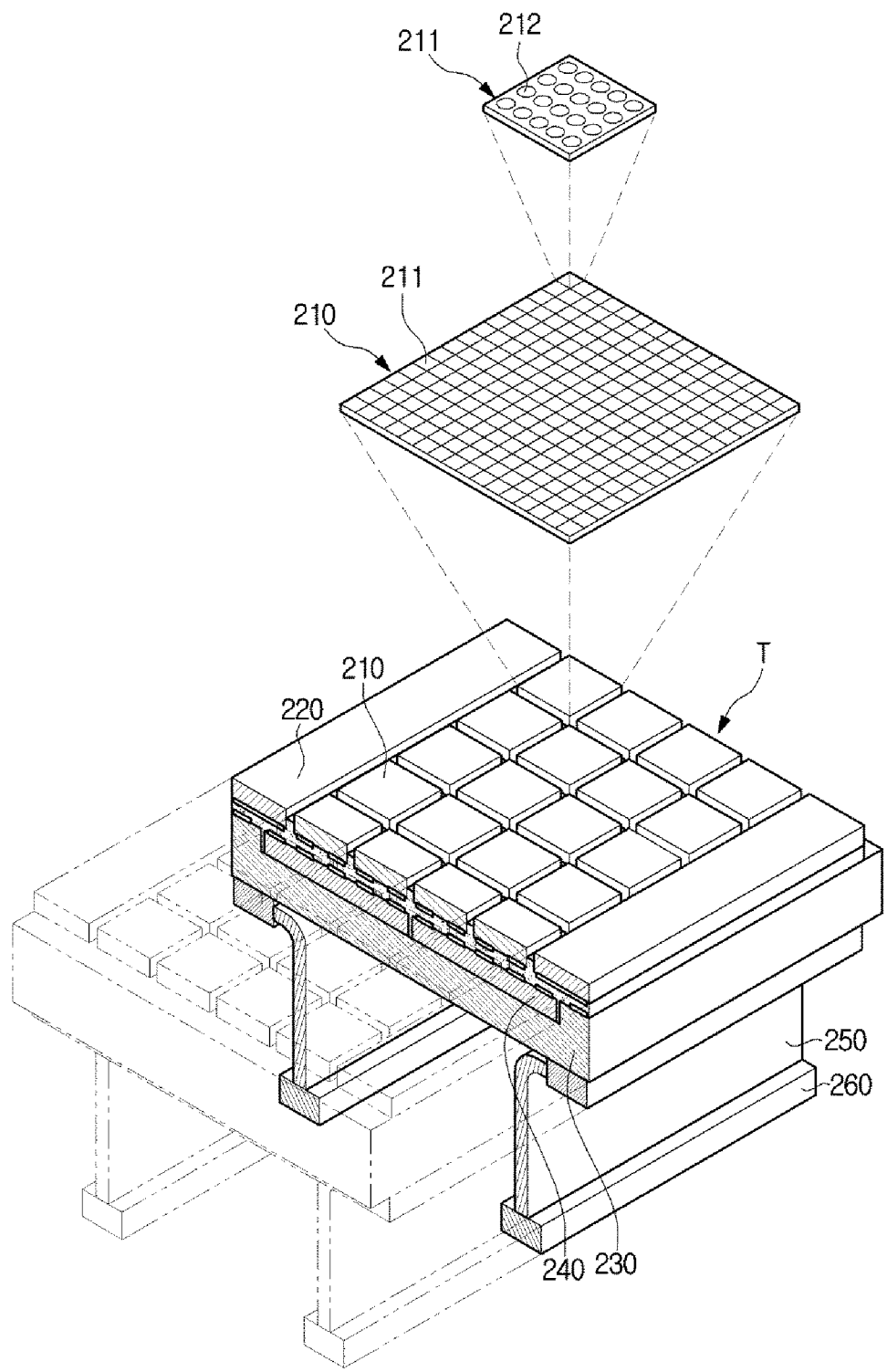
FIG. 3 is a view illustrating an exemplary structure of a transducer array of the ultrasonic probe.

FIG. 2 is a view illustrating an ultrasonic probe including a one-dimensional (1D) transducer array and a two-dimensional (2D) transducer array according to an embodiment of the present disclosure. FIG. 3 is a view illustrating an exemplary structure of a transducer array of the ultrasonic probe.

For example, the transducer array 210 may include a one-dimensional (1D) transducer array as shown in FIG. 2(a). Respective transducer elements 211 constructing the 1D transducer array 210 may convert ultrasonic signals into electric signals and vice versa. For this purpose, the transducer elements 211 may include a magnetostrictive ultrasonic transducer using magnetostrictive effects of a magnetic material, a piezoelectric ultrasonic transducer using piezoelectric effects of a piezoelectric material, and a piezoelectric micromachined ultrasonic transducer (pMUT). If necessary, the transducer elements 211 may also include capacitive micromachined ultrasonic transducer (cMUT) to transmit and receive ultrasonic waves using vibration of several hundred or thousand micromachined thin films 212.

The transducer array 210 may generate ultrasonic signals according to a pulse signal or Alternating Current (AC) signal, and may emit the ultrasonic signals to the target object. The ultrasonic signals emitted to the target object may be reflected from a target site of the interior of the target object. The transducer array 210 may receive the reflected echo ultrasonic signals, may convert the received echo ultrasonic signals into electrical signals, and may generate an ultrasonic image.

The transducer array 210 may receive a power source from an external power-supply device, an internal battery, or the like. If the transducer array 210 is powered on, a piezoelectric vibrator or a thin film 212 of the transducer elements 211 of the transducer array 210 vibrates. The transducer array 210 may emit ultrasonic signal generated by vibration of the piezoelectric vibrator or thin film 212 to the target object. Upon receiving the reflected echo ultrasonic signals from the target object, the piezoelectric vibrator or thin film 212 constructing the transducer array 210 may vibrate in response to the received echo ultrasonic signals. The transducer array 210 may generate an AC signal having a frequency corresponding to a vibration frequency of the piezoelectric vibrator or thin film 212, and may convert ultrasonic waves into electrical signals (hereinafter referred to as ultrasonic signals).

Meanwhile, the transducer array 210 of the ultrasonic probe 200 may be configured in a linear shape as shown in FIG. 2(a), or may be configured in a convex shape. Although the basic operation principles of the ultrasonic probe 200 are identical in the above-mentioned two cases. If the transducer array 210 is a convex-shaped transducer array, an ultrasonic beam emitted from the transducer array 210 may be generated in a fan shape such that the generated ultrasonic image may also be generated in a fan shape.

In another example, the transducer array 210 may include the 2D transducer array 210 as shown in FIG. 2(b). If the transducer array 210 includes the 2D transducer array 210, the internal image of the target object may be 3D-imaged.

In the case of using the 1D transducer array 210, the ultrasonic probe 200 may acquire volume data according to the freehand scheme. Alternatively, the ultrasonic probe 200 may acquire volume data according to the mechanical scheme without using user manipulation. In the case of using the 2D transducer array 210, the ultrasonic probe 200 may acquire volume data by controlling the transducer elements 211.

The respective transducer elements 211 constructing the 2D transducer array 210 is identical to the transducer elements 211 constructing the 1D transducer array 210, and as such a detailed description thereof will herein be omitted for convenience of description.

In addition, assuming that the transducer array 210 includes the 2D transducer array 210, it may be possible to acquire a superior beamforming effect higher than in the case of using the 1D transducer array 210 having the same number of transducer elements 211 even though the same delay frequency is applied.

The ultrasonic probe 200 is connected to the main body of the ultrasonic imaging apparatus 100 through the cable 130 as described above, such that the ultrasonic probe 200 may receive various signals needed to control the ultrasonic probe 200, or may transmit an analog signal or digital signal corresponding to the echo ultrasonic signals received by the ultrasonic probe 200 to the main body.

However, the scope or spirit of the ultrasonic probe 200 according to the present disclosure is not limited thereto, the ultrasonic probe 200 is implemented as a wireless communication probe, and the ultrasonic probe 200 may also communicate with the main body over the network as necessary.

Referring to FIG. 3, the transducer module T configured to transmit and receive ultrasonic waves may include a transducer array 210 for transmission/reception (Tx/Rx) of ultrasonic waves; a pad bridge 220 configured to include wiring blocks (or line blocks) for electrical connection between an integrated circuit (IC) 240 and a printed circuit board (PCB) 230; the integrated circuit (IC) 240 to which the transducer array 210 is bonded; the PCB 230 and a flexible PCB 250 configured to connect the IC 240 to a control board 260 so as to transmit a transmission (Tx) signal generated from the control board 260 to the IC 240; and the control board 260 configured to output a transmission (Tx) signal for generating ultrasonic waves to the IC 240. Although FIG.

3 exemplarily illustrates the ultrasonic probe 200 including the 2D transducer array 210 for convenience of description, an ultrasonic probe, an ultrasonic imaging apparatus including the same, and a method for controlling the ultrasonic imaging apparatus according to one embodiment may also be implemented by the ultrasonic probe 200 including the 1D transducer array 210.

The PCB 230 may be electrically connected to the transducer array 210 through the IC 240, may receive the pulse signal from the main body of the ultrasonic imaging apparatus 100, and may transmit the received pulse signal to the transducer array 210.

The IC 240 may be connected to the PCB 230, may receive the pulse signal from the PCB 230, and may transmit the received pulse signal to the transducer array 210. Although the IC 240 can be used in the ultrasonic probe including the 2D transducer array 210 illustrated in FIG. 2, the IC 240 may not be used in the ultrasonic probe 200 including the 1D transducer array 210. That is, the PCB 230 may be directly connected to the transducer array 210 through wiring or like, such that the signal received by the PCB 230 may also be directly transferred to the transducer array 210.

The transducer array 210 of the transducer module T may be bonded to the IC 240 such as Application Specific Integrated Circuits (ASIC) according to the flip chip bonding scheme. Upon receiving the pulse signal from the main body of the ultrasonic imaging apparatus 100 through the control board 260, the IC 240 may adjust generation of ultrasonic or pulse signals by controlling the signal applied to the transducer array 210 according to logic operation.

As illustrated in FIG. 3, the PCB 230 may be electrically connected to the IC 240 through the pad bridge 220 composed of line blocks, or may be connected to the IC 240 through wiring.

The control board 260 may control the switching circuit contained in the ultrasonic probe 200 according to one embodiment of the present disclosure.

The transducer array 210 may be a basic unit for constructing the transducer module T. The transducer array 210 may be comprised of the transducer elements 211 arranged in a 2D array. The transducer elements 211 may include 2D-array shaped thin films 212 configured to vibrate upon receiving the electrical signal.

For example, the transducer module T may include a (4×8)-sized 2D array comprised of 32 transducer arrays 210, and one transducer array 210 may include a (16×16)-sized 2D array comprised of 256 transducer elements 211. One transducer element 211 may include 20 to 25 thin films 212 that vibrate by the electric signal so as to generate ultrasonic waves. In this case, the transducer module T may include a total of 163,840 to 204,800 thin films 212.

FIG. 4 is a graph illustrating waveforms of pulse signals used for pulse inversion harmonic imaging of ultrasonic imaging diagnosis.

In ultrasonic imaging diagnosis, the pulse inversion harmonic imaging scheme may be an ultrasonic technology for effectively detecting a harmonic signal or a non-linear signal. Whereas the ultrasonic probe 2200 transmits only one ultrasonic signal during general grayscale ultrasound transmission, the pulse inversion harmonic imaging scheme may successively transmit ultrasonic pulse signals having opposite phases and the same waveform. That is, as illustrated in FIG. 4(a), positive pulse signals may be successively transmitted. As illustrated in FIG. 4(b), negative pulse signals may be successively transmitted. FIG. 4 illustrates that voltage pulses of about −80V~+80V are generated as transmission pulse signals and transmitted.

According to the pulse inversion harmonic imaging scheme, a linear signal in which an ultrasonic waveform is hardly modified is not formed because the positive pulse signal and the negative pulse signal are offset, and a non-linear signal in which an ultrasonic waveform is modified is not offset so that the non-linear signal is greatly amplified. That is, the pulse inversion harmonic imaging scheme can effectively image only non-linear signals regarding tissues of the target object.

As illustrated in FIG. 4, a pulse signal comprised of two fundamental frequencies having different polarities may be emitted to the human body through the ultrasonic probe 200. Thereafter, an image is formed using two signals having different polarities reflected from the human body. The return signal obtained by incidence of the positive signal illustrated in FIG. 4(a) may include a positive fundamental frequency component and a harmonic component. The return signal obtained by incidence of the negative signal illustrated in FIG. 4(b) may include a negative fundamental frequency component and a harmonic component. In this case, if two return signals are summed, the fundamental frequency components have different polarities, so that the fundamental frequency components are offset such that no signal occurs and the harmonic frequency component may be doubled in size. The pulse inversion harmonic imaging scheme can have raw ultrasonic information without execution of frequency filtering, and can effectively separate the non-linear signal from the linear signal, such that the pulse inversion harmonic imaging scheme can provide a smaller number of imaginary images as well as high-quality images. Accordingly, if lesion or the like exists in the target object, signals other than the offset and disappeared fundamental frequency pulse signals are generated, such that ultrasonic diagnosis can be carried out using the generated signals. As can be seen from the waveforms of FIG. 4, a positive pulse signal and a negative pulse signal are correctly symmetrical such that the sum of the positive pulse signal and the negative pulse signal is offset. Generally, the positive pulse signal and the negative pulse signal for use in the pulse inversion harmonic imaging method are transmitted by the pulse transmitter located in the main body of the ultrasonic imaging apparatus 100, and the transmission part of the positive pulse signal and the transmission part of the negative pulse signal are separated from each other.

Figure 5:
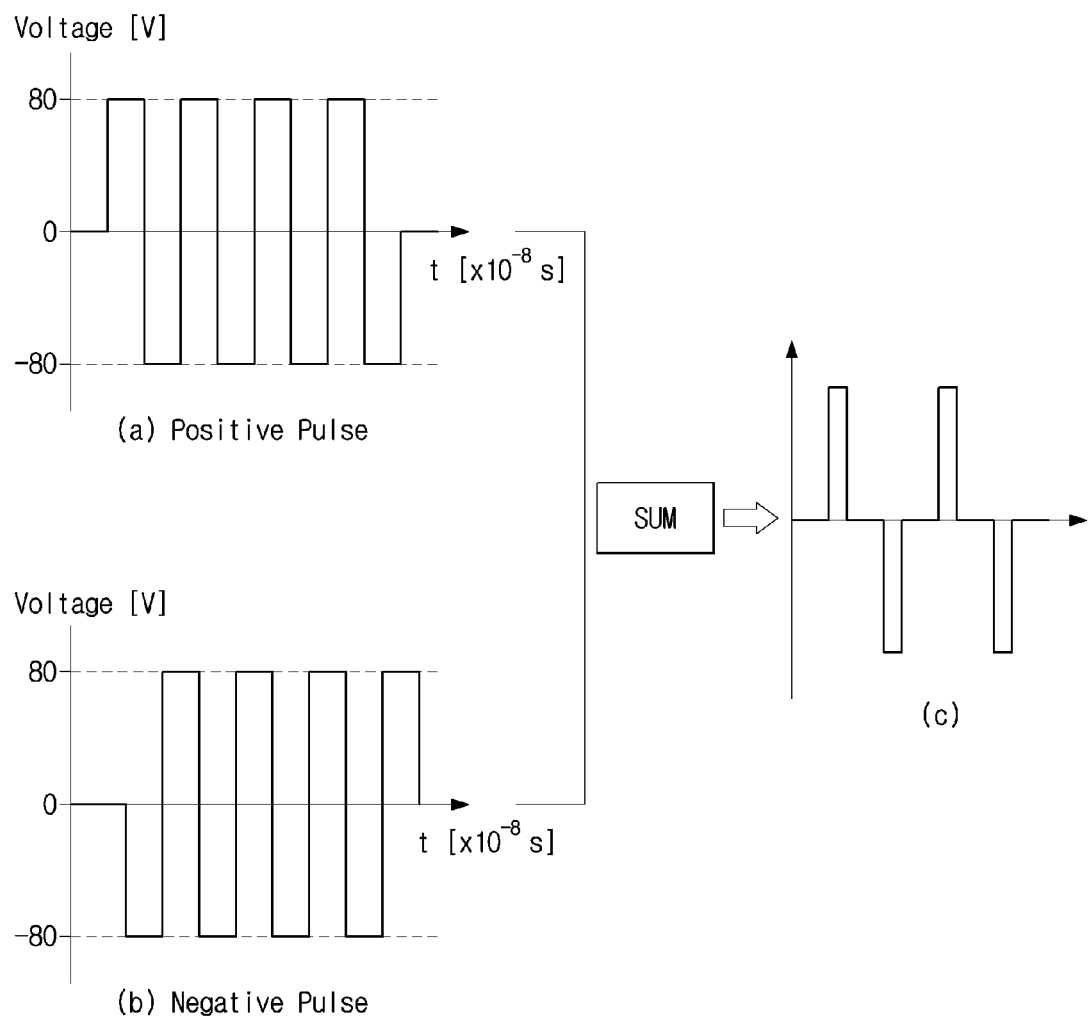
FIG. 5 is a graph illustrating the problem encountered by asymmetry in pulse signals used for pulse inversion harmonic imaging of ultrasonic imaging diagnosis.

FIG. 5 is a graph illustrating the problem encountered by asymmetry in pulse signals used for pulse inversion harmonic imaging of ultrasonic imaging diagnosis.

Referring to FIG. 4, the positive pulse signal and the negative pulse signal according to the pulse inversion harmonic imaging scheme must be correctly symmetrical to offset fundamental frequency components. However, assuming that the positive pulse signal and the negative pulse signal are asymmetrical to each other, the fundamental frequency components are not offset and the residual pulse signals remain.

Referring to FIG. 5, the negative pulse signal of FIG. 5(a) is inaccurately symmetrical to the positive pulse signal of FIG. 5(b), for various reasons. Generally, there may be slight differences between the transmission (Tx) elements contained in the pulse transmitter for transmitting pulse signals. The pulse transmitter of the ultrasonic imaging apparatus 100 may include a positive transmission element for outputting positive pulse signals and a negative transmission element for outputting negative pulse signals. In this case, fabrication characteristics of the positive transmission element and the negative transmission element are different from each other, and device characteristics of the positive transmission element and the negative transmission element are different from each other, such that it may be impossible to transmit pulse signals in which symmetry is completely guaranteed during transmission of the pulse signals. In addition, there may be a little difference in phase between signals in signal transmission. The pulse signal generated from the main body of the ultrasonic imaging apparatus 100 arrives at the ultrasonic probe 200, and must pass through the cable having a length of 1 to 3 m such that the pulse signal can be emitted through the transducer array 210. In this case, the pulse signals may be modulated. Differently from FIGS. 4 and 5, asymmetrical signals may occur due to asymmetrical voltages of the positive and negative pulse signals.

FIG. 5(*c*) illustrates the residual pulse signals generated in signal synthesis due to asymmetry between the positive pulse signal and the negative pulse signal. If the positive pulse signal and the negative pulse signal are synthesized, asymmetry between the positive pulse signal and the negative pulse signal is not guaranteed although the fundamental frequency components must be offset and cancelled, such that the residual pulse signals may remain. The positive pulse signal and the negative pulse signal are different in waveform from those of FIGS. 4 and 5. Waveforms of the residual pulse signals generated by asymmetrical characteristics may also be different from those of FIGS. 4 and 5.

Figure 6A:
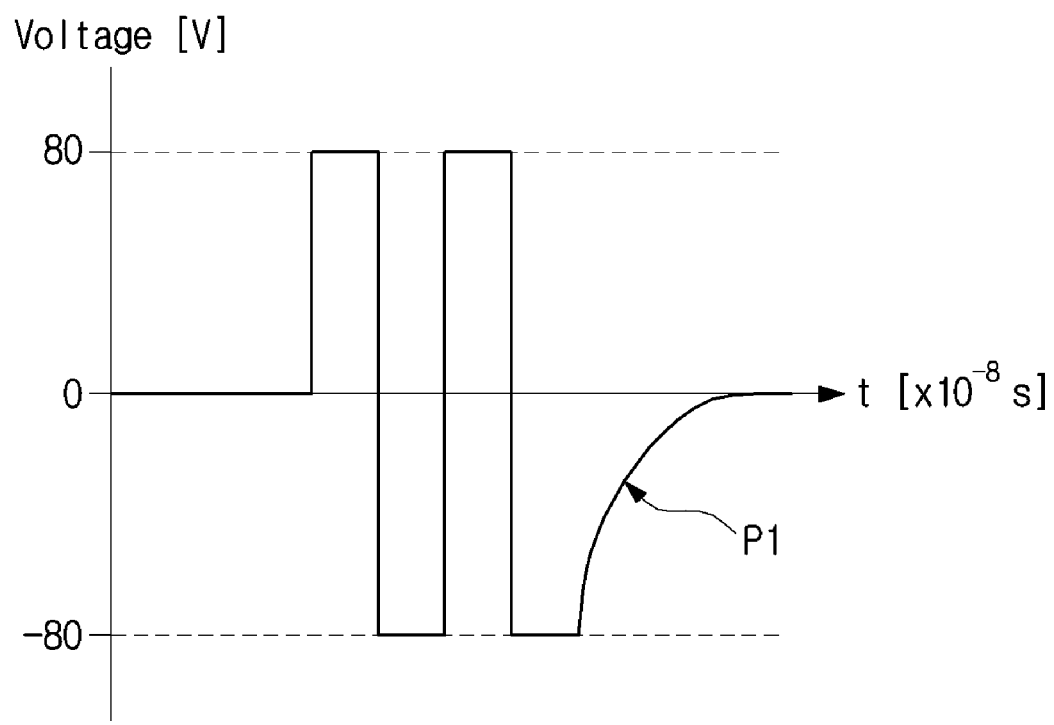
FIGS. 6A and 6B are graphs illustrating the problem encountered by waveforms of signals generated by the residual voltage of pulse signals.
Figure 6B:
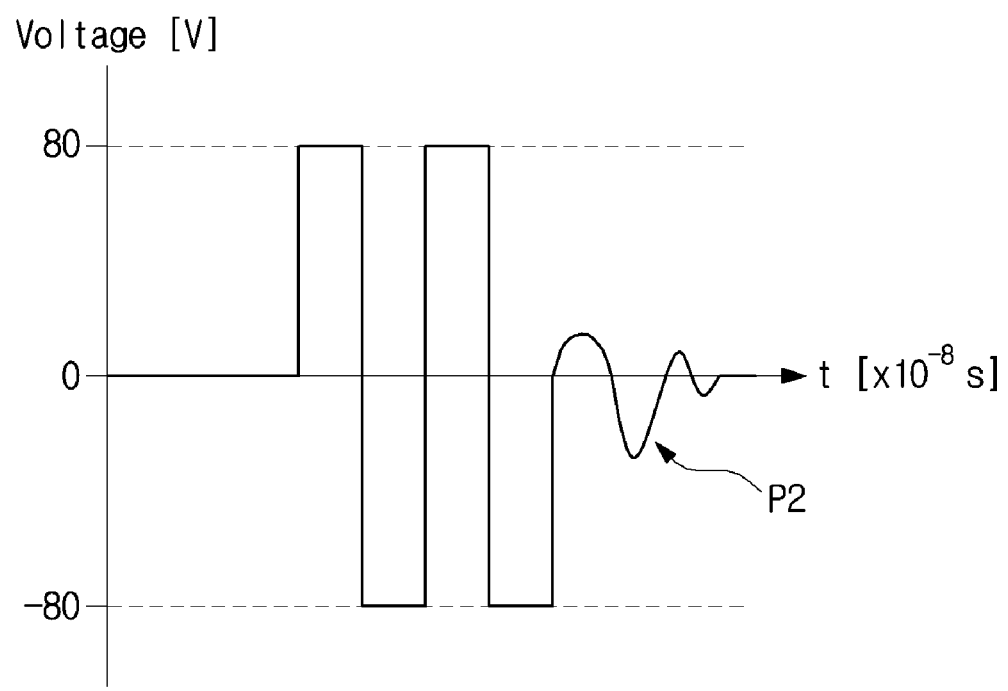

FIGS. 6A and 6B are graphs illustrating the problem encountered by waveforms of signals generated by the residual voltage of pulse signals.

Referring to FIG. 6A, drooping P1 of the pulse signals transferred from the main body of the ultrasonic imaging apparatus 100 to the ultrasonic probe 200 may encounter some problems. That is, the positive pulse signal or the negative pulse signal needs to be a voltage pulse alternately having a voltage of +80V or a voltage of −80V as illustrated in FIG. 6A. In this case, signal drooping P1 may occur when the voltage pulse ranges from 0V to +80V or ranges from −80V to 0V. The signal drooping P1 may be caused either by signal modulation generated when the pulse signals are transferred from the main body of the ultrasonic imaging apparatus 100 to the ultrasonic probe 200, or by signal modulation generated when the pulse signals are transferred from the PCB 230 of the ultrasonic probe 200 to the transducer elements 211.

Differently from FIG. 6A, rolling P2 of the pulse signals transferred from the main body of the ultrasonic imaging apparatus 100 to the ultrasonic probe 200 may occur as shown in FIG. 6B. That is, there may arise the signal rolling P2 when voltage pulses of the positive pulse signal or the negative pulse signal have curved waveforms. In the same manner as in the signal drooping P1 of FIG. 6A, the signal rolling P2 may be transferred from the main body of the ultrasonic imaging apparatus 100 to the ultrasonic probe 200, and may be encountered by pulse signal demodulation generated when signals are applied to the transducer elements 211.

An additional circuit is needed to remove the drooping P1 or the rolling P2 of the pulse signals. If such circuits are added, circuit complexity caused by additional circuits unavoidably increases and the controller for controlling the circuits is additionally needed. As a result, the ultrasonic probe, the ultrasonic imaging apparatus including the same, and the method for controlling the ultrasonic imaging apparatus according to one embodiment can address the above issues.

Figure 8:
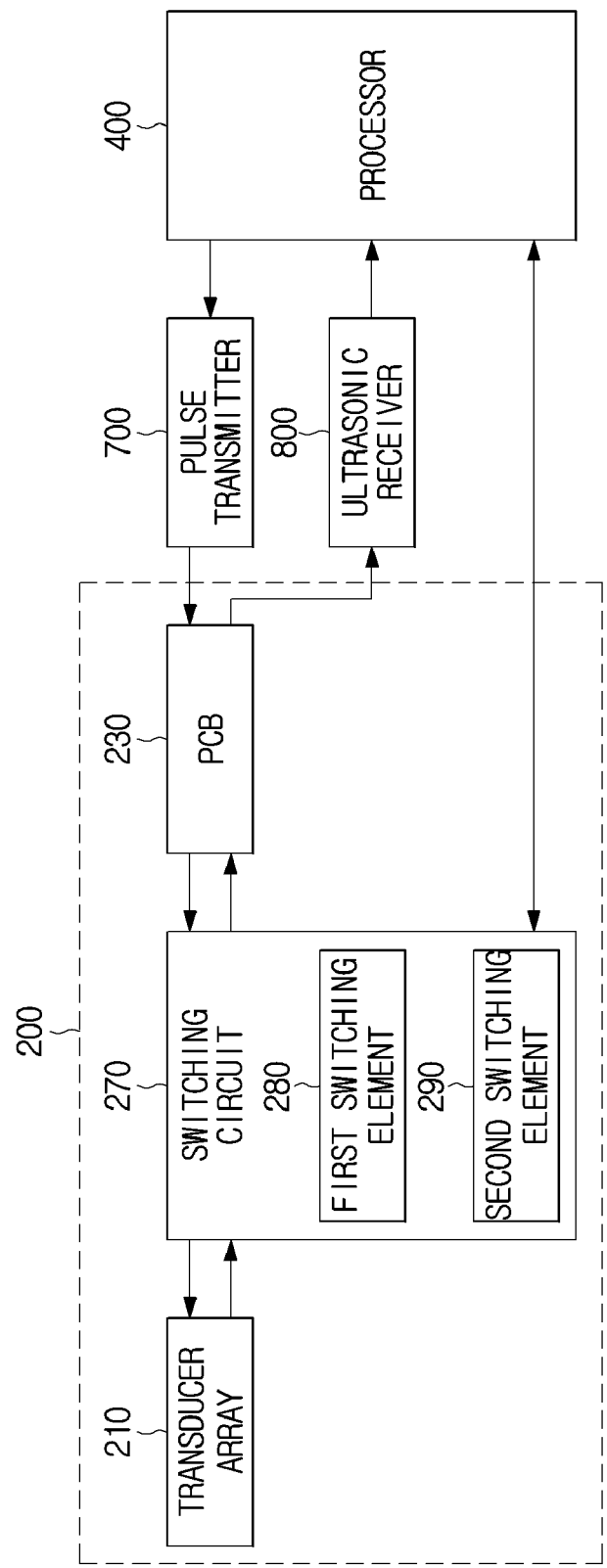
FIG. 8 is a block diagram illustrating an ultrasonic probe according to an embodiment of the present disclosure.

FIG. 7 is a block diagram illustrating an ultrasonic imaging apparatus including an ultrasonic probe according to an embodiment of the present disclosure. FIG. 8 is a block diagram illustrating an ultrasonic probe according to an embodiment of the present disclosure.

Referring to FIG. 7, the ultrasonic imaging apparatus 100 may include a display 160, an ultrasonic probe 200, a beamforming module 300, a processor 400, an image processor 500, a memory 600, a pulse transmitter 700, and an ultrasonic receiver 800.

Referring to FIG. 8, the ultrasonic probe 200 according to one embodiment may include a transducer array 210, a switching circuit 270 including both a first switching element 280 and a second switching element 290, and a printed circuit board (PCB) 230.

The ultrasonic probe 200 may be implemented in various ways within the scope of technology idea of acquiring volume data of the target object. The ultrasonic probe 200 configured to contact the skin of a target object may transmit and receive ultrasonic signals to or from the target object. In more detail, the ultrasonic probe 200 may generate ultrasonic signals according to input pulses, may transmit the generated ultrasonic signals to the inside of the target object, and may receive echo ultrasonic signals reflected from a specific part of the target object.

In addition, the ultrasonic probe 200 according to one embodiment may include the PCB 230 and the switching circuit 270, and may change waveforms of the pulse signals received from the ultrasonic imaging apparatus 100. As illustrated in FIG. 3, the ultrasonic probe 200 may include the PCB 230 and the IC 240. The PCB 230 may receive the pulse signals from the ultrasonic imaging apparatus 100. In the case of the one-dimensional (1D) transducer array, the IC 240 may not be contained in the ultrasonic probe 200. In contrast, in the case of the 2D transducer array, the IC 240 may be contained in the ultrasonic probe 200.

The pulse transmitter 700 of the main body of the ultrasonic imaging apparatus 100 may transmit the pulse signals to the ultrasonic probe 200 under the control of the processor 400. The pulse signal transmitted from the pulse transmitter 700 may arrive at the PCB 230 of the ultrasonic probe 200 after passing through the cable 130. In this case, signals may also be transmitted through the control board 260. The PCB 230 may transmit the received pulse signal to the switching circuit 270. The switching circuit 270 may be contained in the IC 240 such as an ASIC, or may be directly connected to the transducer array 210. The switching circuit 270 may include the first switching circuit 280 and the second switching element 290, may change a waveform of the received pulse signal, and may transmit the changed pulse signal to the transducer array 210. The transducer array 210 may emit the pulse signal to the target object, and may receive the echo ultrasonic signals reflected from the target object. The sound signal received by the transducer array 210 may be converted into an electrical signal, and may be transferred to the switching circuit 270. The reflected ultrasonic signal may be received by the ultrasonic receiver 800 of the main body of the ultrasonic imaging apparatus 100 after passing through the PCB 230, such that the resultant ultrasonic signal may be transferred to the processor 400. A control method for changing waveforms of the pulse signals using the first switching element 280 and the second switching element 290 contained in the switching circuit 270 will hereinafter be described with reference to FIGS. 9 to 13.

The beamforming module 300 may perform beamforming to focus ultrasonic signals transmitted/received through the ultrasonic probe 200. The beamforming module 300 may include a transmission beamformer (not shown) and a reception beamformer (not shown) such that an analog signal is converted into a digital signal or vice versa. As a result, a difference in time between ultrasonic signals transmitted from one or more transducers, or a difference in time between ultrasonic signals received from one or more transducers may be adjusted. Although the beamforming module 300 may be contained in the main body of the ultrasonic imaging apparatus 100, the beamforming module 300 may also be contained in the ultrasonic probe 200 so as to perform its own role. Even when the ultrasonic probe is a wireless probe connected to the ultrasonic imaging apparatus 100 over a wireless communication network, the beamforming module 300 may also be contained in the wireless probe as necessary. The beamforming module 300 may be implemented using any one of various well-known beamforming methods, may be implemented by a combination of various methods or may be selectively used.

The processor 400 may receive beamforming data from the beamforming module 300, and may transmit data in a manner that the image processor 500 may perform image processing. In addition, information received from the input module 150 may be stored in the memory 600, and the processor 400 may generate the pulse signal by controlling the pulse transmitter 700 and may control the pulse transmitter 700 to transmit the pulse signal to the ultrasonic probe 200. In addition, the processor 400 may control the ultrasonic receiver 800 to receive the ultrasonic signal reflected from the ultrasonic probe 200, and the image processor 500 may control the image processor 500 to process the signal received by the ultrasonic receiver 800 so that the resultant signal can be displayed on the display 160. The processor may be implemented as an array composed of a plurality of logical gates, and may also be implemented as a combination of a universal microprocessor and a memory storing programs capable of being executed in the universal microprocessor.

The image processor 500 may generate an ultrasonic image by processing the beamformed echo ultrasonic signals. The image processor 500 may process the echo ultrasonic signals using any well-known image processing methods. For example, the image processor 500 may perform time gain compensation (TGC) processing of the beamformed echo ultrasonic signals. Thereafter, the image processor 500 may establish a dynamic range (DR). After the DR is established, the image processor 500 may compress the echo ultrasonic signals belonging to the DR. Finally, the image processor 500 rectifies the echo ultrasonic signals, and thus removes noise from the rectified ultrasonic signals. The image processor 500 may generate an ultrasonic image using the processed echo ultrasonic signals. The image processor 500 may generate various kinds of ultrasonic images. For example, the ultrasonic images generated by the image processor 500 may include an A-mode (Amplitude Mode) image, a B-mode (Brightness Mode) image, an M-mode (Motion Mode) image, and a Doppler mode image.

The image processor 500 may process image signals obtained by pulse signal transmission/reception according to the pulse inversion harmonic imaging scheme. In this case, the image processor 500 may be one or more processors.

The memory 600 may store information regarding the switching operation of the first switching element 280 and information regarding the switching operation of the second switching element 290 according to one embodiment. In addition, data regarding the control command, which selectively operates the first switching element 280 and the second switching element 290 from among the plurality of switching circuits 270 respectively connected to the plurality of transducer elements 211, may also be stored in the memory 600.

For example, although the memory 600 may include a high-speed random access memory (RAM), a magnetic disk, an SRAM, a DRAM, a ROM, etc., the scope or spirit of the present disclosure is not limited thereto. In addition, the storage unit 600 may be detachably coupled to the ultrasonic imaging apparatus 100. For example, although the storage unit 600 may include a Compact Flash (CF) card, a Secure Digital (SD) card, a Smart Media (SM) card, a Multimedia Card (MMC), or a memory stick, the scope or spirit of the present disclosure is not limited thereto. In addition, the memory 600 is located outside the ultrasonic imaging apparatus 100, and may transmit or receive data to or from the ultrasonic imaging apparatus 100 by wire or wirelessly.

As shown in FIG. 1, the input unit 150 may input a control command for the ultrasonic imaging apparatus 100 or a control command for one constituent element contained in the ultrasonic imaging apparatus 100, and the user may input a control command for pulse inversion harmonic imaging through the input module 150. That is, the user may select the pulse inversion harmonic imaging technique mode of the ultrasonic imaging apparatus 100 through the input module 150, and may input a command for controlling the first switching element and the second switching element 290 contained in the switching circuit 270 of the ultrasonic probe 200.

The display 160 may display various user interfaces (UIs) related to overall control of the ultrasonic imaging apparatus 100, may display ultrasonic images obtained from the ultrasonic diagnosis procedure, or may also provide 2D images and 3D images as necessary. In addition, the display 160 may display waveforms of pulse signals transmitted/received by the pulse inversion harmonic imaging scheme. The user may also input a control command of the ultrasonic imaging apparatus 100 by touching the display 160.

The pulse transmitter 700 may transmit the pulse signal for the pulse inversion harmonic imaging scheme to the ultrasonic probe 200. Although the above-mentioned technology for pulse inversion harmonic imaging must include a transmitter to transmit the positive pulse signal and a transmitter to transmit the negative pulse signal, one embodiment of the present disclosure may include only the pulse signal transmitter 700 to transmit the positive pulse signal as shown in FIG. 4(*a*). That is, the pulse inversion harmonic imaging scheme may be implemented even when the embodiment of the present disclosure includes only the pulse transmitter 700 for transmitting the positive pulse signal. The pulse transmitter 700 may transmit the positive pulse signal according to a control signal of the processor 400, and the PCB 230 of the ultrasonic probe 200 may receive the pulse signal such that the received pulse signal may be transmitted to the switching circuit 270.

The ultrasonic receiver 800 may receive the pulse signal emitted from the ultrasonic probe 200 to the target object and then reflected from the target object. The received pulse signal may be displayed on the display 160 according to a control signal of the processor 400.

Figure 9:
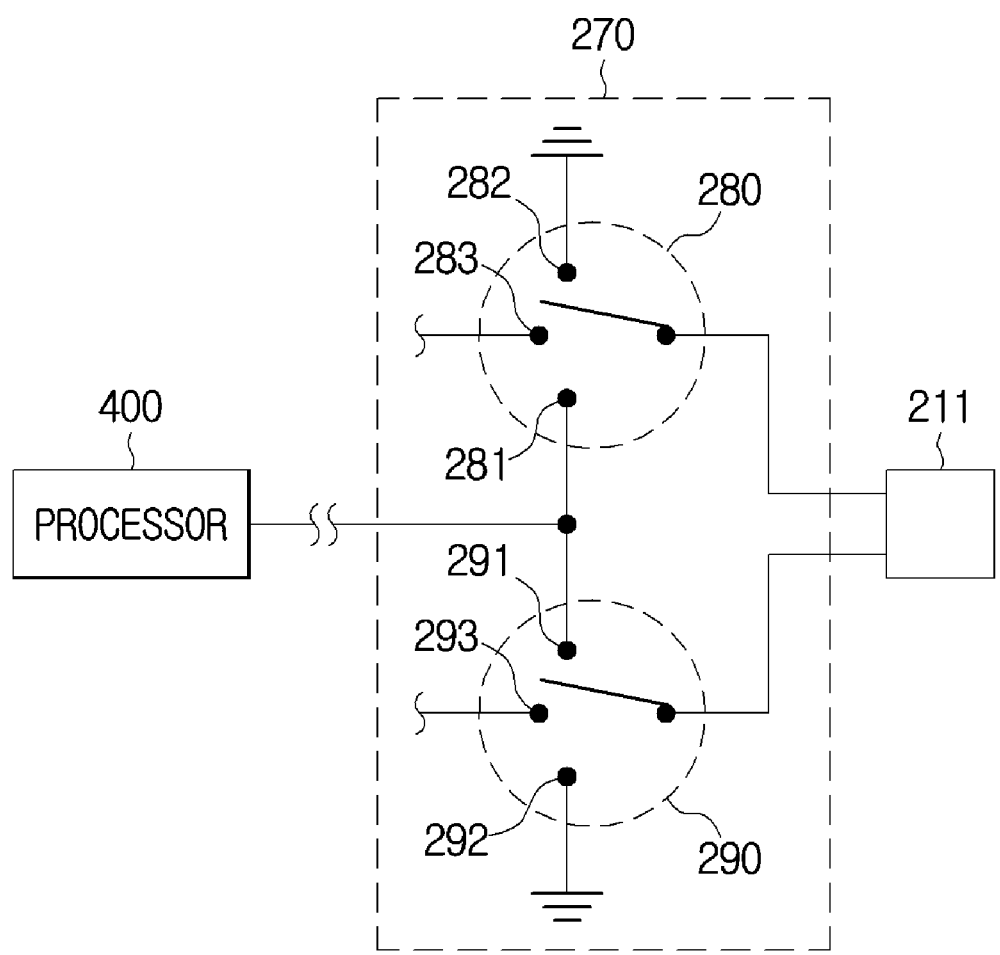
FIG. 9 is a conceptual diagram illustrating a switching circuit configured to change waveforms of pulse signals according to an embodiment of the present disclosure.

FIG. 9 is a conceptual diagram illustrating a switching circuit configured to change waveforms of pulse signals according to an embodiment of the present disclosure.

Referring to FIG. 9, the switching circuit 270 may be connected to the transducer element 211. That is, the switching circuit 270 may be contained in the IC 240 such as an ASIC and may be electrically connected to the transducer element 211. If the IC 240 such as the 1D transducer array 210 is not present, the switching circuit 270 is installed at an arbitrary position contained in the ultrasonic probe 200 so that the switching circuit 270 may be directly connected to the transducer element 211.

The switching circuit 270 may include the first switching element 280 and the second switching element 290. The first switching element 280 may include a pulse signal reception (Rx) terminal 281, a ground terminal 282, and a predetermined terminal 283. The second switching element 291 may include a pulse signal reception (Rx) terminal 291, a ground terminal 292, and a predetermined terminal 293. One end of the switching element 270 may be connected to the transducer array 211, and the other end of the switching element may be connected to the main body of the ultrasonic imaging apparatus 100 after passing through the PCB 230.

In this case, the predetermined terminal (283 or 293) may be a terminal having a predetermined potential or may be a terminal having no potential. That is, the predetermined terminal 283 may be assigned a predetermined potential and may be connected to the first switching element 280, and the predetermined terminal 293 may be assigned a predetermined potential and may be connected to the second switching element 290. In this case, the predetermined terminal 283 of the first switching element 280 and the predetermined terminal 293 of the second switching element 290 may have the same potential or different potentials.

In addition, if the predetermined terminal 283 or 293 has no potential, even when the first switching element 280 is connected to the predetermined terminal 283 or the second switching element 290 is connected to the predetermined terminal 293, the predetermined terminal 283 or 293 also has no potential, which means that the predetermined terminals (283, 293) are not connected to anything.

The first switching element 280 of the switching circuit 270 may be connected to any one of the pulse signal reception terminal 281, the ground terminal 282, and the predetermined terminal 283 according to a control signal of the processor 400. The second switching element 290 of the switching circuit 270 may be connected to any one of the pulse signal reception terminal 291, the ground terminal 292, and the predetermined terminal 293 according to a control signal of the processor 400. In addition, the control board 260 contained in the ultrasonic probe 200 may control the first switching element 280 and the second switching element 290.

The first switching element 280 may be connected to the pulse signal reception terminal 281, and the second switching element 290 may be connected to any one of the ground terminal 292 and the predetermined terminal 293. Alternatively, the first switching element 20 may be connected to the ground terminal 282 and the second switching element 290 may be connected to any one of the pulse signal reception terminal 291 and the predetermined terminal 293. The first switching element 280 may be connected to the predetermined terminal 283, and the second switching element 290 may be connected to any one of the pulse signal reception terminal 291 and the ground terminal 292.

The first switching element 280 and the second switching element 290 may be connected to the ground terminals 282 and 292, respectively. The first switching element 280 and the second switching element 290 may be connected to the pulse signal reception terminals 281 and 291, respectively. The first switching element 280 and the second switching element 290 may be connected to the predetermined terminals 283 and 293, respectively.

As described above, the first switching element 280 and the second switching element 290 may indicate a line element for connecting or blocking a current of the electronic device. The switching element may include a transistor for connecting a current in response to a control signal, and may include a bipolar junction transistor (BJT), a field effect transistor (FET), a High Voltage MUX (HVMUX), and a relay, without being limited thereto.

Figure 10:
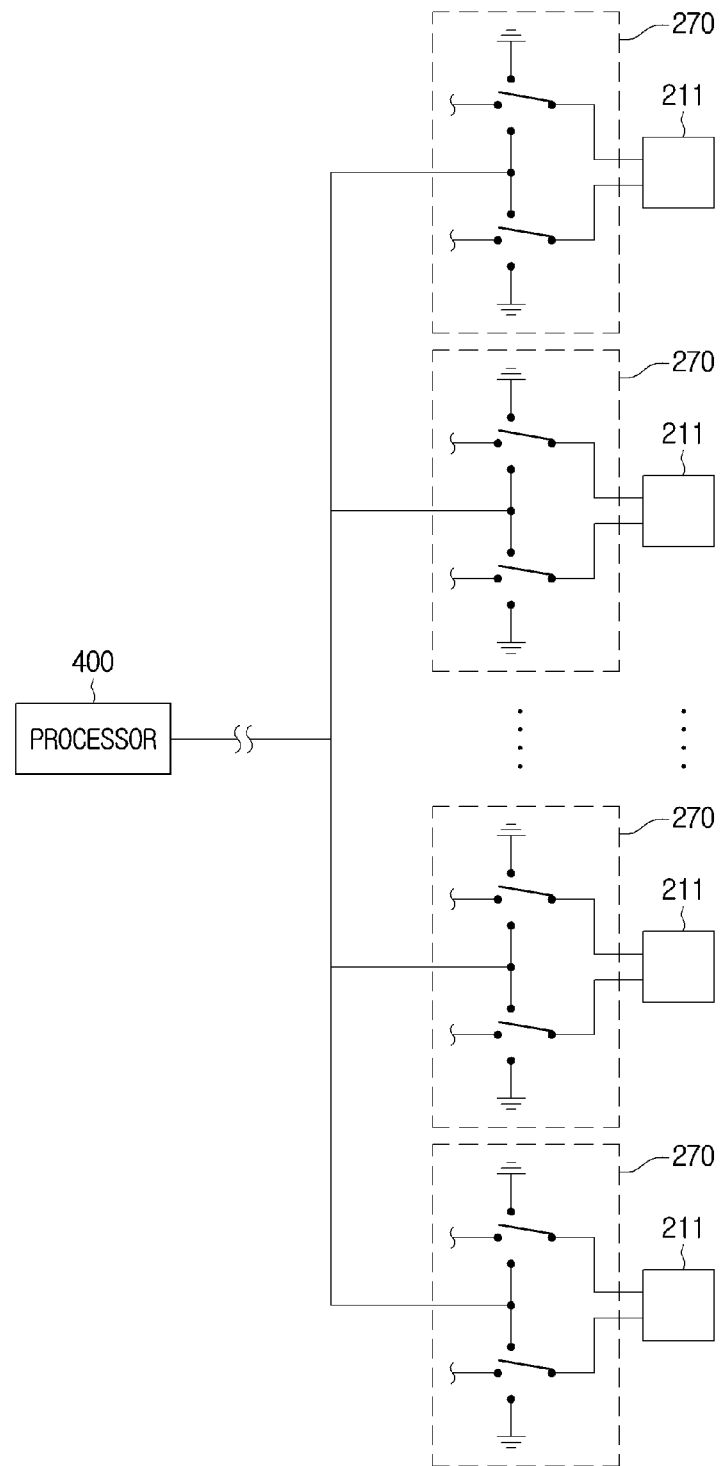
FIG. 10 is a conceptual diagram illustrating a structure in which plural switching circuits configured to change waveforms of pulse signals are respectively connected to plural transducer elements according to an embodiment of the present disclosure.

FIG. 10 is a conceptual diagram illustrating a structure in which plural switching circuits configured to change waveforms of pulse signals are respectively connected to plural transducer elements according to an embodiment of the present disclosure.

Referring to FIG. 3, the transducer array 210 may include a plurality of transducer elements 211. The transducer elements 211 may respectively transmit the pulse signals to the target object. The switching circuits 270 may be respectively connected to the transducer elements 211, the processor 400 or the control board 260 may control the first switching element 280 and the second switching element 290 contained in the switching circuit 270, such that a waveform of the Tx pulse signal for each transducer element 211 may be changed.

The user may input a command for controlling the switching circuit 270 connected to a target transducer element 211 (to be used for change of a waveform of the pulse signal) from among the plurality of transducer elements 211 using the input module 150. In addition, the memory 600 may store data regarding a control command of the switching circuit 270 established for each transducer element 211, and may retrieve a pulse signal change control command regarding the plurality of transducer elements 211 using the stored data in future.

Figure 11:
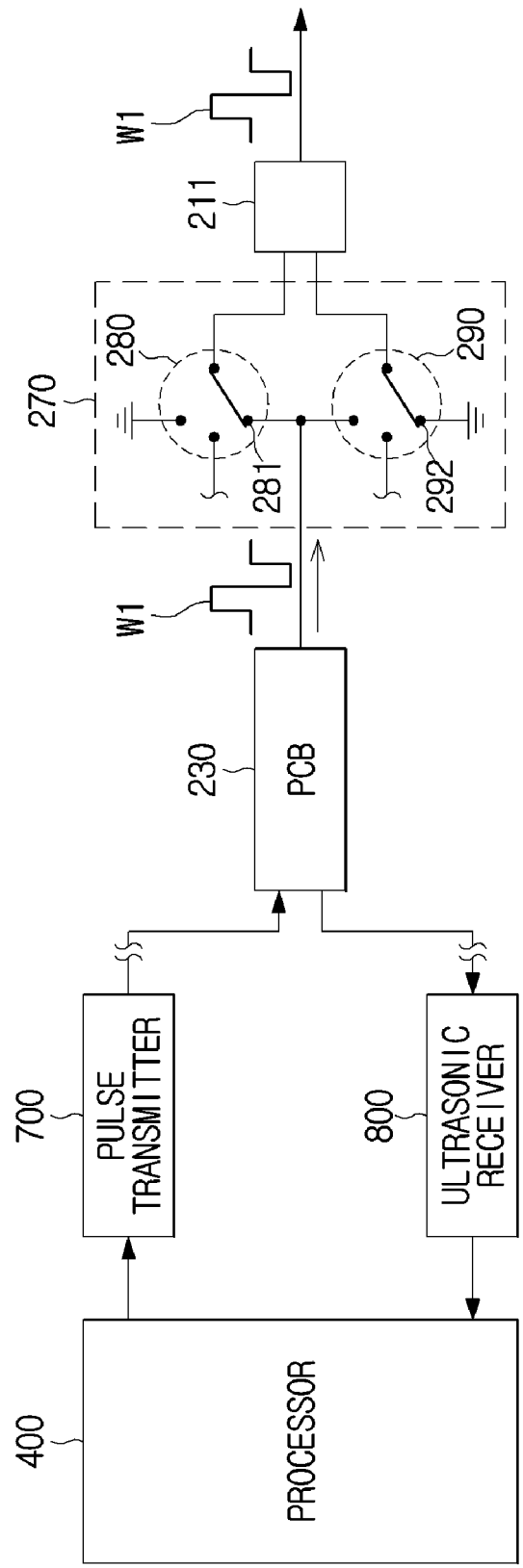
FIG. 11 is a conceptual diagram illustrating operation states of a first switching element and a second switching element which are configured to transmit the same waveform as the pulse signal received by the switching element according to an embodiment of the present disclosure.
Figure 12:
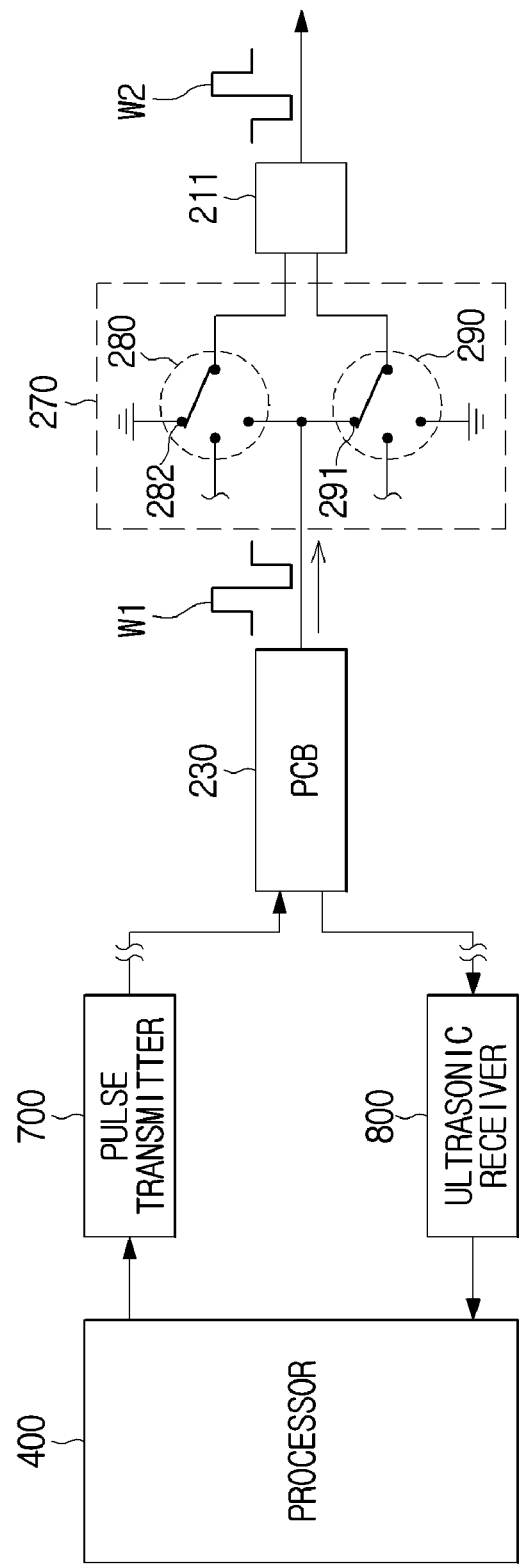
FIG. 12 is a conceptual diagram illustrating operation states of a first switching element and a second switching element which are configured to transmit inversion waveforms of the pulse signals received by the switching circuit according to an embodiment of the present disclosure.
Figure 13A:
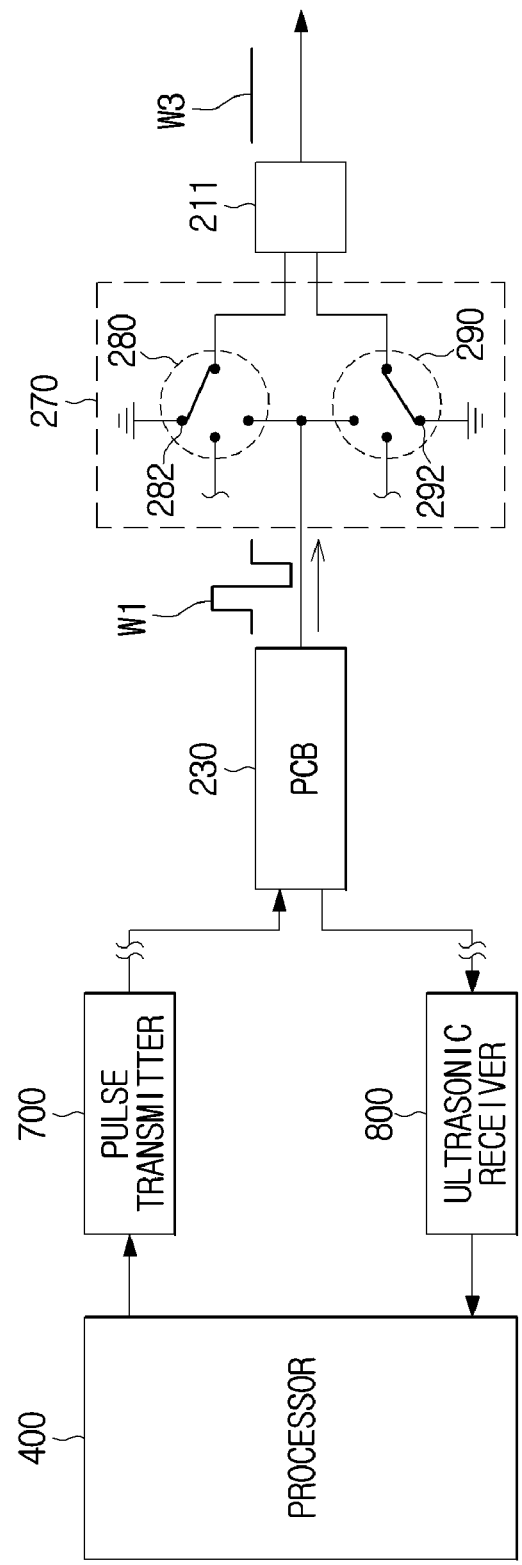
FIG. 13A is a conceptual diagram illustrating operation states of a first switching element and a second switching element in a manner that the first and second switching elements contained in the switching circuit are connected to a ground terminal such that a signal from which the received pulse signal is removed is transmitted.
Figure 13B:
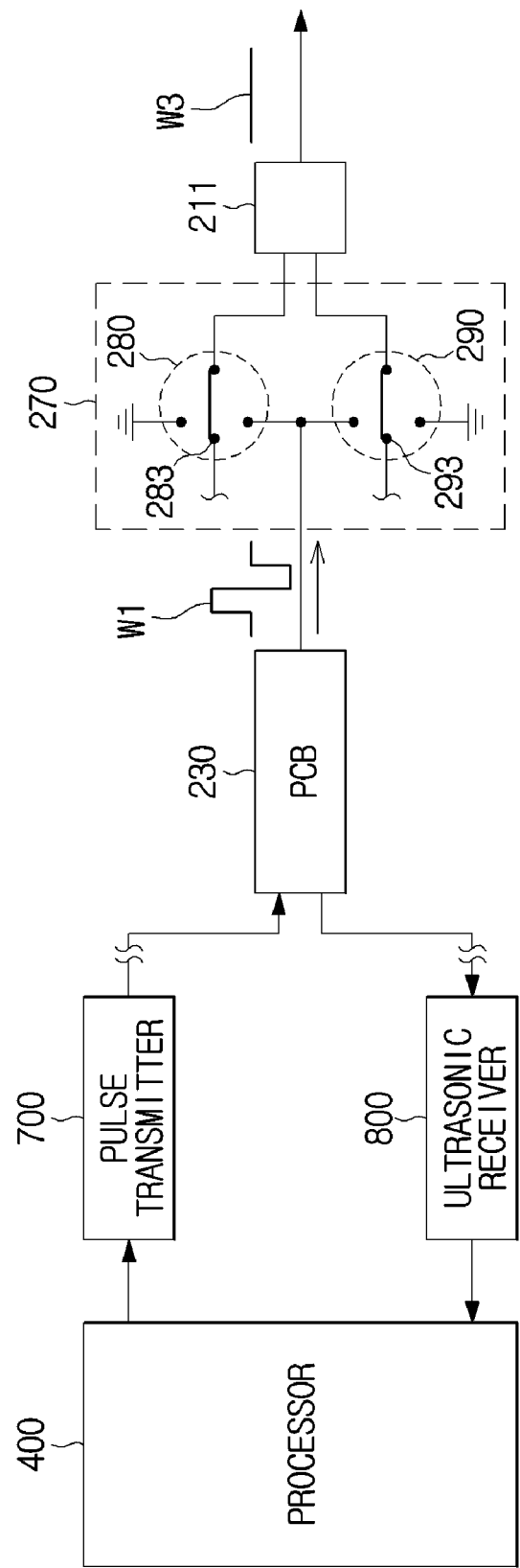
FIGS. 13B to 13D are conceptual diagrams illustrating operation states of a first switching element and a second switching element in a manner that the first and second switching elements contained in the switching circuit are connected to any one of a ground terminal and a predetermined terminal such that a signal from which the received pulse signal is removed is transmitted.
Figure 13C:
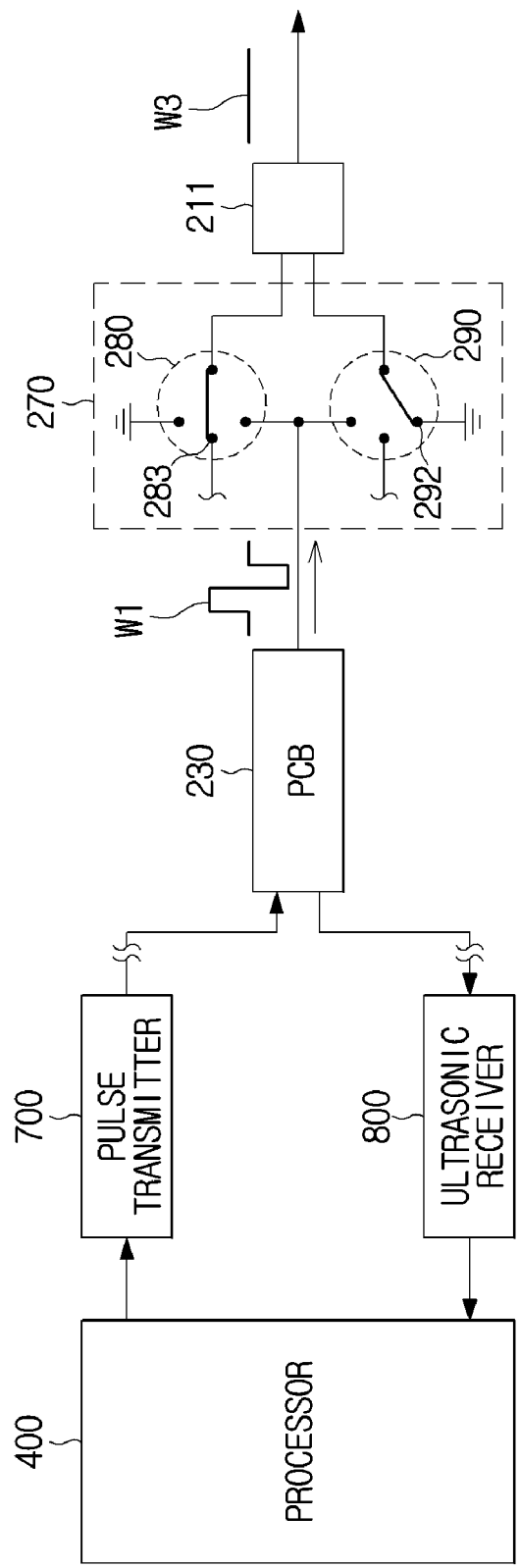
Figure 13D:
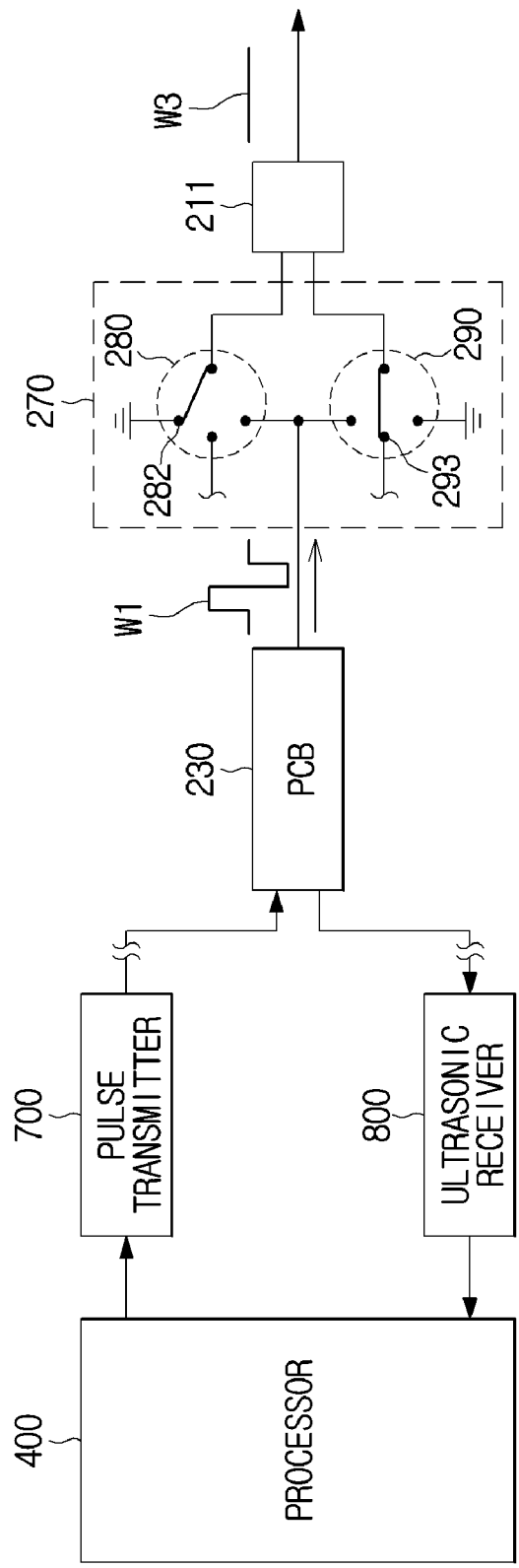
Figure 13E:
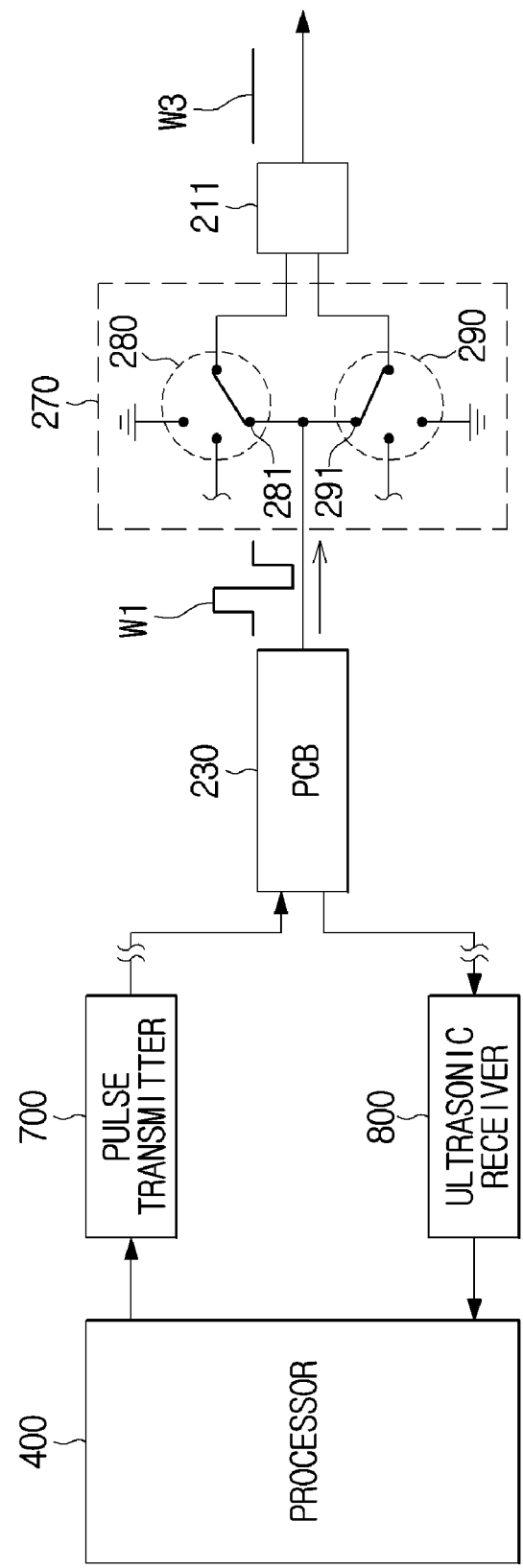
FIG. 13E is a conceptual diagram illustrating operation states of a first switching element and a second switching element in a manner that the first and second switching elements contained in the switching element are connected to a pulse signal reception terminal such that a signal from which the received pulse signal is removed is transmitted.

FIG. 11 is a conceptual diagram illustrating operation states of a first switching element and a second switching element which are configured to transmit the same waveform as the pulse signal received by the switching element according to an embodiment of the present disclosure. FIG. 12 is a conceptual diagram illustrating operation states of a first switching element and a second switching element which are configured to transmit inversion waveforms of the pulse signals received by the switching circuit according to an embodiment of the present disclosure. FIG. 13A is a conceptual diagram illustrating operation states of a first switching element and a second switching element in a manner that the first and second switching elements contained in the switching circuit are connected to a ground terminal such that a signal from which the received pulse signal is removed is transmitted. FIGS. 13B to 13D are conceptual diagrams illustrating operation states of a first switching element and a second switching element in a manner that the first and second switching elements contained in the switching circuit are connected to any one of a ground terminal and a predetermined terminal such that a signal from which the received pulse signal is removed is transmitted. FIG. 13E is a conceptual diagram illustrating operation states of a first switching element and a second switching element in a manner that the first and second switching elements contained in the switching element are connected to a pulse signal reception terminal such that a signal from which the received pulse signal is removed is transmitted.

Referring to FIG. 11, the positive pulse signal W1 generated and transmitted from the pulse transmitter 700 of the main body of the ultrasonic imaging apparatus 100 may be received by the PCB 230 of the ultrasonic probe 200, such that the positive pulse signal W1 may be received by the switching element 270 before arriving at the transducer element 211.

For pulse inversion harmonic imaging, two pulse signals having the same shape and opposite phases are successively transmitted, and the positive pulse signal W1 may be transmitted to the target object through the ultrasonic probe 200. If the positive pulse signal W2 is received by the switching circuit 270, the processor 400 or the control board 260 may control the first switching element 280 or the second switching element 290 contained in the switching circuit 270 according to a control command entered by the user who uses the input module 150 or according to a control command stored in the memory 600.

As shown in FIG. 11, the first switching element 280 may be connected to the pulse signal reception terminal 281, and the second switching element 290 may be connected to the ground terminal 292. If the first switching element 280 is connected to the pulse signal reception terminal 281 and the second switching element 290 is connected to the ground terminal 292, the positive pulse signal W1 configured to pass through the switching circuit 270 may be output as the positive pulse signal W1 having the same waveform as the signal received by the switching circuit 170. That is, the positive pulse signal W1 having passed through the switching circuit 270 may be transferred to the target object through the transducer element 211.

Referring to FIG. 12, the positive pulse signal W1 generated and transmitted from the pulse transmitter 700 of the main body of the ultrasonic imaging apparatus 100 is received by the PCB 230 of the ultrasonic probe 200 such that the positive pulse signal W1 may be received by the switching element 270 before arriving at the transducer element 211 as shown in FIG. 11.

For pulse inversion harmonic imaging, if the positive pulse signal W1 is received by the switching circuit 270, the processor 400 or the control board 260 may control the first switching element 280 and the second switching element 290 contained in the switching circuit 270 according to a control command stored in the memory 600 or a user-input control command entered through the input module 150.

Referring to FIG. 12, the first switching element 280 may be connected to the ground terminal 282, and the second switching element 290 may be connected to the pulse signal reception terminal 291. If the first switching element 280 is connected to the ground terminal 283 and the second switching element 290 is connected to the pulse signal reception terminal 291, the positive pulse signal W1 having passed through the switching circuit 270 may be output as the negative pulse signal W1 that is symmetrical to the signal received by the switching circuit 270 whereas it has an inversion waveform. That is, the negative pulse signal W1 having passed through the switching circuit 270 may be transmitted to the target object through the transducer element 211.

The negative pulse signal W2 and the positive pulse signal W1 are symmetrical to each other and the phase of the negative pulse signal W2 is opposite to the phase of the positive pulse signal W1. If the negative pulse signal W2 and the positive pulse signal W1 are summed, the fundamental frequency part may be offset.

In the related art, the main body of the ultrasonic imaging apparatus 100 transmits each of the negative pulse signal and the positive pulse signal. In this case, the positive pulse signal and the negative pulse signal having correct symmetry may not be transmitted due to a difference between the transmission element or transmitter for transmitting the positive pulse signal and the other transmission element or transmitter for transmitting the negative pulse signal. Even when the positive pulse signal and the negative pulse signal are symmetrical, the completely symmetrical signals may not be transmitted to the target object when the pulse signal is modulated to arrive at the ultrasonic probe 200 after passing through the cable 130 and is then transmitted from the transducer element 211 to the target object. Therefore, the completely symmetrical positive pulse and negative pulse signals do not arrive at the target object, such that the preferable pulse inversion harmonic imaging scheme may not be carried out.

In accordance with the above-mentioned embodiment, even when the pulse transmitter 700 of the main body of the ultrasonic imaging apparatus 100 transmits two successive pulse signals for pulse inversion harmonic imaging as illustrated in FIG. 12, the signal having the same waveform as the positive pulse signal W1 may be transmitted. Therefore, even when the asymmetrical pulse phenomenon caused by a difference between the transmission elements or transmitters for transmitting the pulse signals does not occur, the positive pulse signal W1 having the same waveform is transmitted, such that asymmetry encountered when the pulse signal passes through the cable 130 can be addressed. In addition, only the waveform of the positive pulse signal W1 received by the PCB 230 of the ultrasonic probe 200 and then transferred to the switching circuit 270 is inverted by switching of the first switching element 280 and the second switching element 290, such that the positive pulse signal W1 symmetrical to the negative pulse signal W2 may be transferred to the transducer array 211.

Referring to FIGS. 13A to 13E, the positive pulse signal W1 generated and transmitted from the pulse transmitter 700 of the main body of the ultrasonic imaging apparatus 100 in the same manner as in FIGS. 11 and 12 may be received by the PCB 230 of the ultrasonic probe 200, such that the positive pulse signal W1 may be received by the switching element 270 before arriving at the transducer element 211.

If the positive pulse signal W1 is received by the switching circuit 270, the processor 400 or the control board 260 may control the first switching element 280 and the second switching element 290 contained in the switching circuit 270 according to a user-input control command received from the input module 150 or according to a control command stored in the memory 600.

Referring to FIG. 13A, the first switching element 280 may be connected to the ground terminal 282, and the second switching element 290 may be connected to the ground terminal 292. If the first switching element 280 and the second switching element 290 are connected to the ground terminals 282 and 292, respectively, the positive pulse signal W1 scheduled to pass through the switching circuit 270 at the corresponding time may be output as the other signal W3 having no pulse signal. That is, when using the successive pulse signals transmitted according to successive time lapse, the pulse signal may be zero at a specific time at which the first switching element 280 and the second switching element 290 are respectively connected to the ground terminal 282 and 292, such that the resultant signal having a zero value may be transmitted.

Referring to FIG. 13B, the first switching element 280 and the second switching element 290 may be connected to the predetermined terminals 283 and 293, respectively.

As described above, the predetermined terminal 283 or 293 may be a terminal having an arbitrary potential or may be a terminal having no potential. That is, the predetermined terminal 283 or 293 may be assigned a predetermined potential, such that the predetermined terminal 283 may be connected to the first switching element 280 or the predetermined terminal 293 may be connected to the second switching element 290. In this case, the predetermined terminal 283 of the first switching element 280 and the predetermined terminal 293 of the second switching element 290 may have the same potential or different potentials.

In addition, if the predetermined terminal 283 or 293 has no potential, even when the first switching element 280 is connected to the predetermined terminal 283 or the second switching element 290 is connected to the predetermined terminal 293, the predetermined terminal 283 or 293 also has no potential, which means that the predetermined terminals (283, 293) are not connected to anything.

If the first switching element 280 and the second switching 290 are respectively connected to the predetermined terminal 283 and the predetermined terminal 293, the positive pulse signal W1 scheduled to pass through the switching circuit 270 at the corresponding time may be output as the signal W1 having no pulse signal. That is, when using the successive pulse signals transmitted according to successive time lapse, the pulse signal may be zero at a specific time at which the first switching element 280 and the second switching element 290 are respectively connected to the predetermined terminals 283 and 293, such that the resultant signal having a zero value may be transmitted.

Referring to FIG. 13C, the first switching element 280 may be connected to the predetermined terminal 293, and the second switching element 290 may be connected to the ground terminal 292. In this case, the positive pulse signal W1 scheduled to pass through the switching circuit 270 at the corresponding time may be output as the signal W1 having no pulse signal. That is, when using the successive pulse signals transmitted according to successive time lapse, the pulse signal may be zero at a specific time at which the first switching element 280 and the second switching element 290 are respectively connected to the predetermined terminals 283 and 293, such that the resultant signal having a zero value may be transmitted.

Referring to FIG. 13D, the first switching element 280 may be connected to the ground terminal 282, and the second switching element 290 may be connected to the predetermined terminal 293. If the first and second switching elements 280 and 290 are connected as described above, the positive pulse signal W1 scheduled to pass through the switching circuit 270 at the corresponding time may be output as the signal W3 having no pulse signal. That is, when using the successive pulse signals transmitted according to successive time lapse, the pulse signal may be zero at a specific time at which the first switching element 280 is connected to the ground terminals 282 and the second switching element 290 is connected to the predetermined terminal 293, such that the resultant signal having a zero value may be transmitted.

Referring to FIG. 13E, the first switching element 280 and the second switching element 290 may be respectively connected to the pulse signal reception terminals 281 and 291. If the first switching element 280 and the second switching element 290 are respectively connected to the pulse signal reception terminals 281 and 291, the positive pulse signal W1 scheduled to pass through the switching circuit 270 at the corresponding time may be output as the signal W3 having no pulse signal. That is, when using the successive pulse signals transmitted according to successive time lapse, the pulse signal may be zero at a specific time at which the first switching element 280 and the second switching element 290 are respectively connected to the pulse signal reception terminals 281 and 291, such that the resultant signal having a zero value may be transmitted.

In the related art, when the pulse signals are transmitted to the ultrasonic probe 200 and then transferred from the PCB 230 to the transducer element 211, drooping P1 and rolling P2 of the pulse signals may occur as illustrated in FIGS. 6A and 6B. In other words, the pulse signal transferred from the pulse transmitter 700 must alternately have the voltage of −80V or the voltage of +80V in the same manner as in the positive pulse signal or the negative pulse signal shown in FIG. 4, such that the pulse signal may have another voltage other than voltage having a repeated period, resulting in drooping or rolling of the pulse signal. Since FIGS. 6A and 6B have exemplarily disclosed rectangular pulse signals, drooping P1 or rolling P2 of the signals may occur. However, when using a different signal having periodicity instead of the rectangular pulse signal, drooping P1 or rolling P2 of the signal may occur when another voltage other than the voltage having periodicity is applied to the transducer element 211. Drooping P1 or rolling P2 of such signals may deteriorate transmission of the pulse signals having symmetrical characteristics during the pulse inversion harmonic imaging process. Therefore, when drooping P1 or rolling P2 of the voltage occurs, the first switching element 280 is connected to the ground terminal 282 and the second switching element 290 is connected to the ground terminal 292 under the control of the processor 400 or the control board 260, the pulse signal applied at the corresponding time is removed, resulting in prevention of the drooping P1 or rolling P2 of the pulse signal. If drooping P1 or rolling P2 of the pulse signal is removed, resolution of the ultrasonic image may increase. The effects according to one embodiment will be described later with reference to FIGS. 19A and 19B.

Stability of the target object may also be improved by controlling the first switching element 280 and the second switching element 290 illustrated in FIGS. 13A to 13E. In other words, assuming that a faulty or abnormal signal occurs in ultrasonic or pulse signals received from the ultrasonic imaging apparatus 100 and it is impossible to control the ultrasonic imaging apparatus 100, if such signal arrives at the target object such as a human, there may be a high risk of damaging or hurting the target object, such that blocking of signals is needed. Accordingly, if the above-mentioned abnormal signal is monitored, the processor 400 or the control board 260 may control the first switching element 280 or the second switching element 290 to be connected to one of the pulse signal reception terminal (281 or 291), the ground terminal (282 or 292), and the predetermined terminal (283 or 293), such that the abnormal signal can be prevented or blocked. The abnormal signal may be detected by a temperature sensor (not shown) contained in the ultrasonic imaging apparatus 100 or the ultrasonic probe 200 or by the processor 400. The above-mentioned effects according to the above-mentioned embodiment will also be described with reference to FIG. 22.

In addition, through control of the first switching element 280 and the second switching element 290 illustrated in FIGS. 13A to 13E, the stabilization problem of the transducer element 211 in transmission of the pulse signal may be obviated.

That is, in different composite modes, when the pulse signals are transmitted through the transducer element 211, one pulse signal having a high-amplitude voltage value is first transmitted, and the other pulse signal having a low-amplitude voltage value is then transmitted.

In this case, the transducer element 211 may not be stabilized and may vibrate by the residual current or voltage between transmission of the pulse signal having a high-amplitude voltage value and transmission of the other pulse signal having a low-amplitude voltage value. Although the transducer element 211 may not vibrate between transmission of the pulse signal having a high-amplitude voltage value and transmission of the other pulse signal having a low-amplitude voltage value, if one pulse signal transmission and the other pulse signal transmission having a time difference therebetween are performed at different time points, the transducer element 211 may vibrate by the initial transmission pulse signal, there is a need to stabilize the transducer element 211 so as to remove such vibration.

Therefore, the processor 400 or the control board 260 may control the first switching element 280 and the second switching element 290 to be connected to any one of the pulse signal reception terminal (281 or 291), the ground terminal (282 or 292), and the predetermined terminal (283 or 293) between pulse transmission time points of pulse signals having a time difference therebetween, such that the residual voltage or current of the pulse signal is removed, such that the transducer element 211 can be stabilized. The effects according to the above-mentioned embodiment will be described later with reference to FIGS. 20A and 20B.

Figure 14:
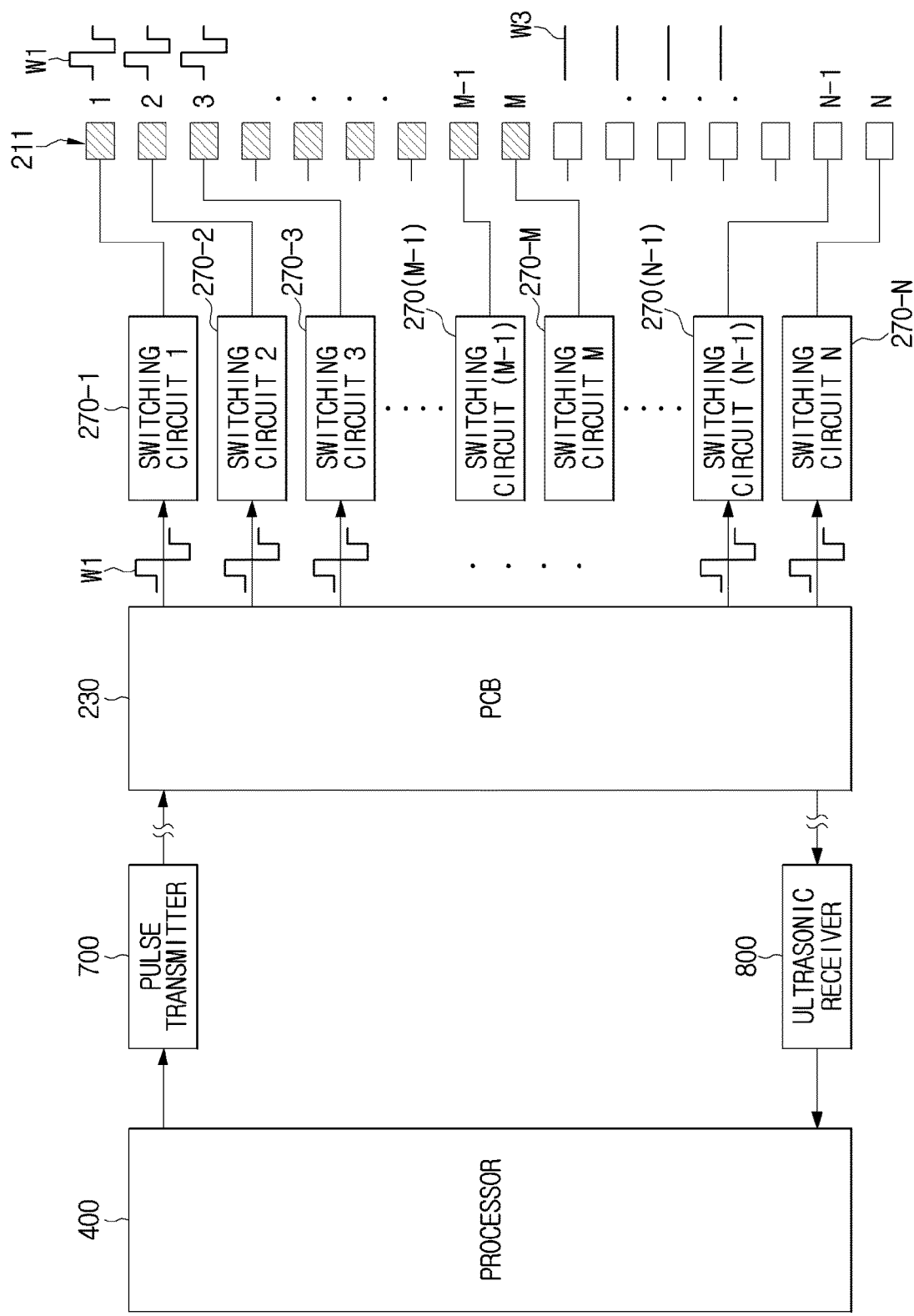
FIG. 14 is a conceptual diagram illustrating that plural switching circuits configured to change waveforms of pulse signals are respectively connected to plural transducer elements and a switching circuit operates per transducer element.

FIG. 14 is a conceptual diagram illustrating that plural switching circuits configured to change waveforms of pulse signals are respectively connected to plural transducer elements and a switching circuit operates per transducer element.

Referring to FIG. 14, the respective transducer elements 211 may be respectively connected to the respective switching circuits (270-1 to 270-N). In addition, the respective switching circuits (270-1 to 270-N) may be connected to the PCB 230 and may receive the pulse signal from the main body of the ultrasonic imaging apparatus 100.

As illustrated in FIGS. 9 to 13E, the processor 400 or the control board 260 may change a waveform of the pulse signal received by the switching circuit by controlling the plurality of switching circuits (270-1 to 270-N). Since the switching circuits (270-1 to 270-N) are respectively connected to the transducer elements 211, the first switching element 280 and the second switching element 290 of each switching circuit are controlled such that waveforms of Tx/Rx pulse signals of the transducer element 211 may be independently controlled.

Referring to FIG. 14, the pulse transmitter 700 of the ultrasonic imaging apparatus 100 may transmit the positive pulse signal W1, and the positive pulse signal W1 may be transferred to the switching circuits (270-1 to 270-N) after passing through the PCB 230 of the ultrasonic probe 200.

In order to transmit the positive pulse signal W1 through M transducer elements (1$^{st}$ to M-th transducer elements) from among the transducer elements 211 connected to the plural switching circuits, the first switching element 280 and the second switching element 290 of the switching circuits (1$^{st}$ to M-th transducer elements) connected to the respective transducer elements (1$^{st}$ to M-th transducer elements) can be controlled. That is, the first switching element 280 including the corresponding switching circuits (1$^{st}$ to M-th) may be connected to the pulse signal reception terminal 281, and the second switching element 290 may be connected to the ground terminal 292 or the predetermined terminal 293.

In addition, assuming that the remaining transducer elements other than M transducer elements (1$^{st}$ to M-th transducer elements) do not participate in pulse signal transmission, the first switching element 280 and the second switching element 290 of the remaining switching circuits other than the above-mentioned switching circuits (1$^{st}$ to M-th) may be connected to the pulse signal reception terminals (281, 291), the ground terminals (282, 292), or the predetermined terminals (283, 293). The effects according to one embodiment will be described later with reference to FIG. 21.

That is, the plurality of transducer elements 211 may selectively adjust pulse signal waveform modification and pulse signal transmission/reception (Tx/Rx). Some transducer elements (1$^{st}$ to M-th) may perform pulse signal Tx/Rx, and some other transducer elements (i.e., the remaining transducer elements other than the 1$^{st}$ to M-th transducer elements) may not perform pulse signal Tx/Rx.

As described above, pulse signal interference between contiguous transducer elements 211 may be removed by controlling the respective switching circuits connected to the plurality of transducer elements 211. Referring to FIG. 14, since the M-th transducer element is used for pulse signal transmission, the contiguous transducer elements not receiving the pulse signal may vibrate by influence of pulse signal Tx/Rx of the M-th transducer element. Such influence can be reduced by controlling the switching circuit 270 using the schemes illustrated in FIGS. 13A to 13E.

Figure 15:
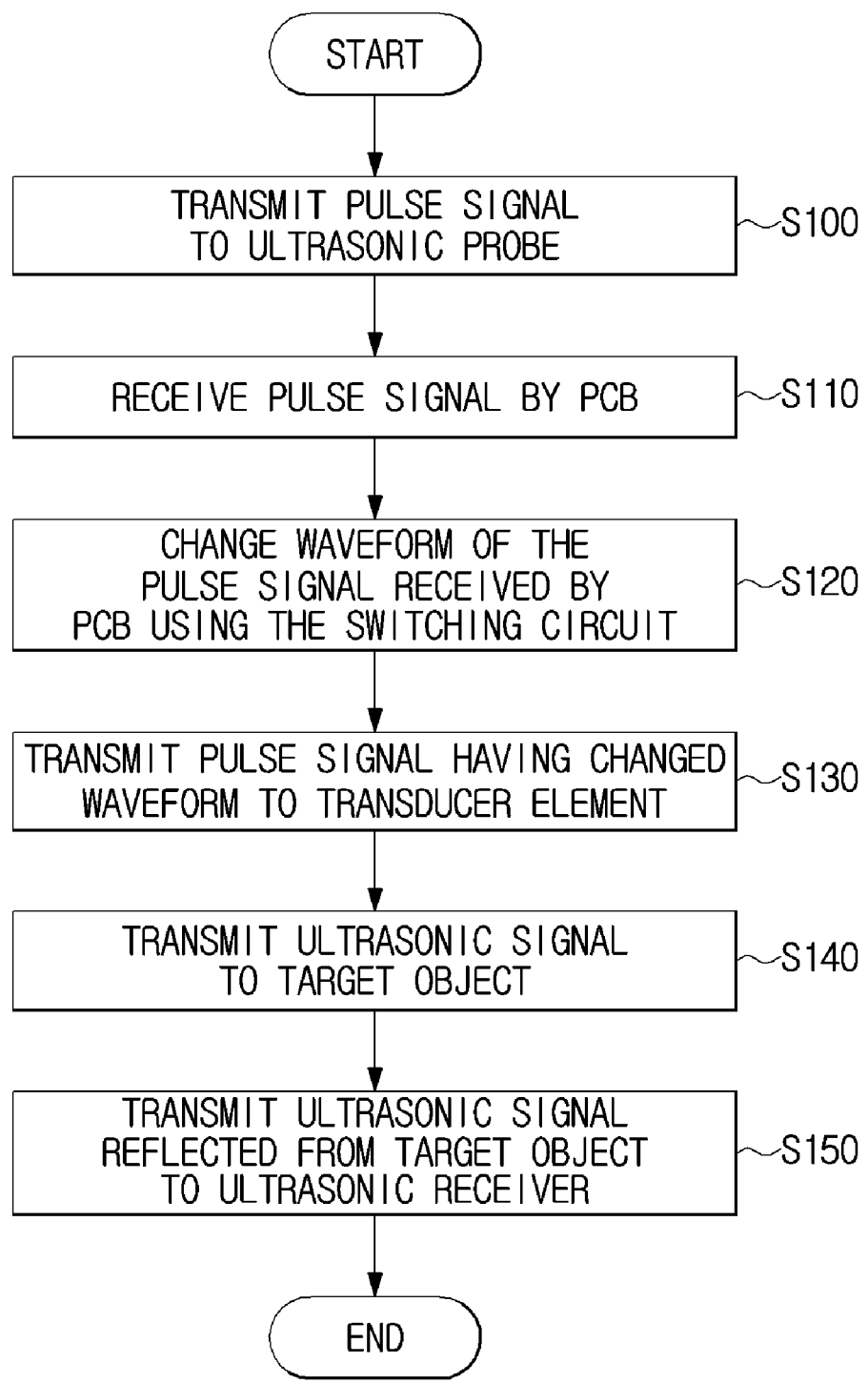
FIG. 15 is a flowchart illustrating a method for controlling an ultrasonic imaging apparatus configured to change waveforms of pulse signals according to an embodiment of the present disclosure.
Figure 16:
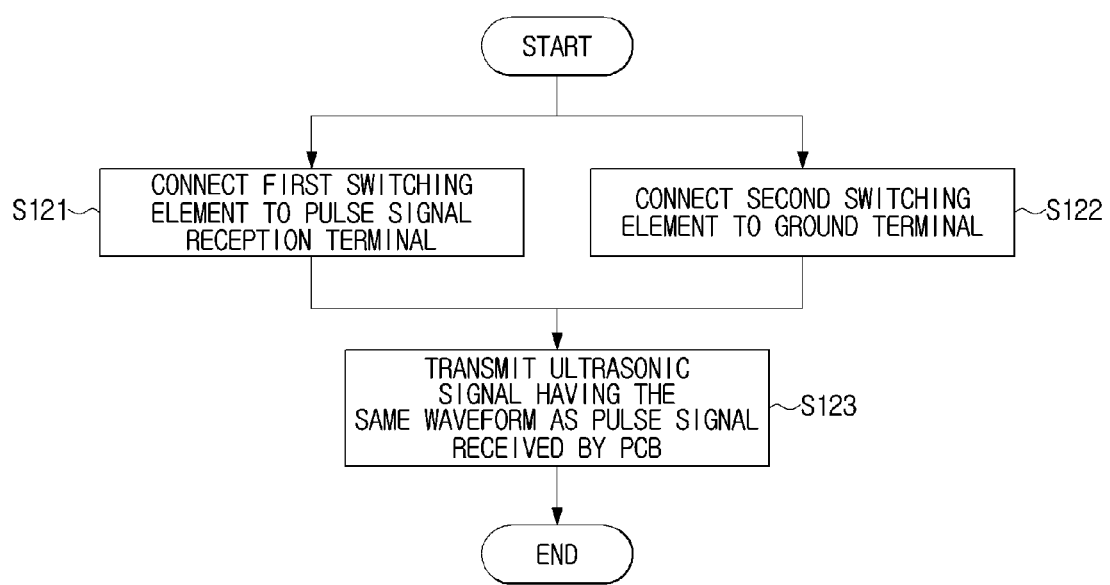
FIG. 16 is a flowchart illustrating a method for controlling a switching circuit so as to transmit ultrasonic signals having the same waveform as a pulse signal received by a printed circuit board (PCB) according to an embodiment of the present disclosure.
Figure 17:
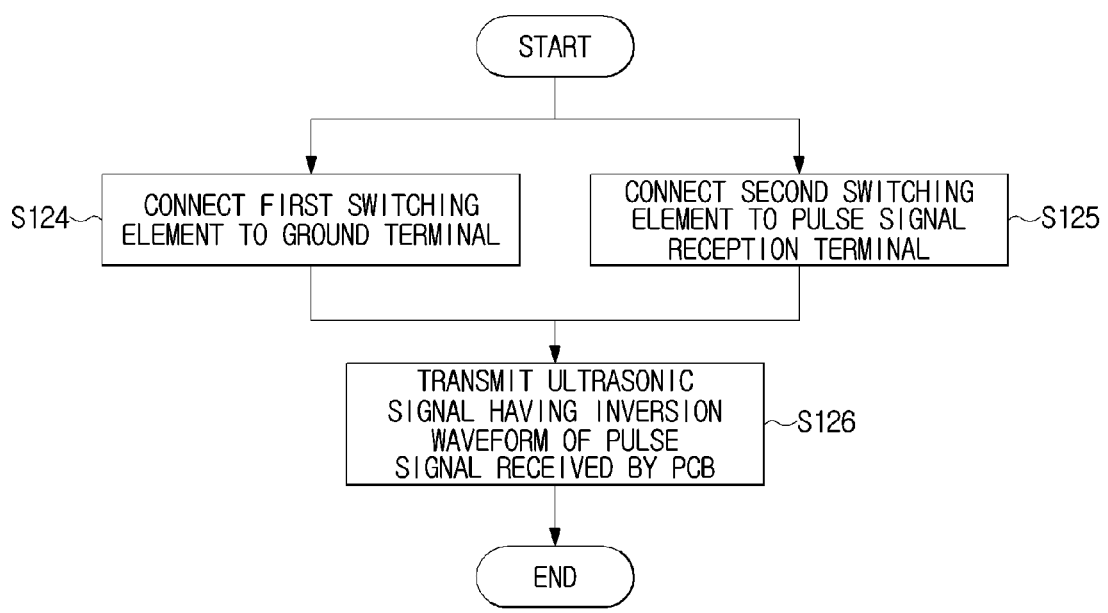
FIG. 17 is a flowchart illustrating a method for controlling a switching circuit so as to transmit ultrasonic signals having an inversion waveform of the pulse signal received by the PCB according to an embodiment of the present disclosure.

FIG. 15 is a flowchart illustrating a method for controlling an ultrasonic imaging apparatus configured to change waveforms of pulse signals according to an embodiment of the present disclosure. FIG. 16 is a flowchart illustrating a method for controlling a switching circuit so as to transmit ultrasonic signals having the same waveform as a pulse signal received by a printed circuit board (PCB) according to an embodiment of the present disclosure. FIG. 17 is a flowchart illustrating a method for controlling a switching circuit so as to transmit ultrasonic signals having an inversion waveform of the pulse signal received by the PCB according to an embodiment of the present disclosure. FIGS. 18A to 18E are flowcharts illustrating methods for controlling the switching circuit so as to transmit ultrasonic signals having a waveform from which the pulse signal received by the PCB is removed according to an embodiment of the present disclosure.

Referring to FIG. 15, the pulse transmitter 700 may transmit the pulse signal to the ultrasonic probe 200 under the control of the processor 400 (S100). If the user inputs a control command for pulse signal transmission through the input module 150 according to pulse inversion harmonic imaging of the embodiment, the pulse transmitter 700 may transmit the positive pulse signal. The pulse signal transmitted from the pulse transmitter 700 may be received by the PCB 230 of the ultrasonic probe 200 after passing through the cable 130 (S110).

The pulse signal received by the PCB 230 may be transferred to the switching circuit 270. As described above, the switching circuit 270 may be located in the IC 240 such as ASIC, or may be independently connected to the transducer element 211.

If the pulse signal is applied to the switching circuit 270, the processor 400 may change a waveform of the pulse signal by controlling the first switching element and the second switching element 290 contained in the switching circuit 270 (S120). The operation of the switching circuit 270 configured to transmit the signal having the same waveform as the pulse signal received by the 230 is shown in FIG. 16. As illustrated in FIG. 11, if the first switching element 280 is connected to the pulse signal reception terminal 281 (S121) and the second switching element 290 is connected to the ground terminal 292 (S122), the switching circuit 270 may transmit the signal W1 having the same waveform as the pulse signal received by the PCB 230 to the transducer element 211 (S130). That is, in order to allow the ultrasonic probe 200 to transmit the positive pulse signal to the target object according to pulse inversion harmonic imaging, the ultrasonic probe 200 may transmit the signal W1 having the same waveform as the positive pulse signal that is transmitted from the pulse transmitter 700 and then received by the PCB 230, to the transducer element 211.

If the waveform of the pulse signal is modified in the switching circuit 270 and then transmitted to the transducer element 211, the ultrasonic probe 200 may transmit ultrasonic signals to the target object (S140). In this case, if the signal W1 having the same waveform as the positive pulse signal received by the PCB 230 is transferred to the transducer element 211, the ultrasonic probe 200 may transmit the ultrasonic signal having the same waveform as the pulse signal that is transmitted from the pulse transmitter 700 and then received by the PCB 230, to the target object (S123).

The operations of the switching circuit 270 configured to transmit the signal corresponding to an inversion waveform of the pulse signal received by the PCB 230 are shown in FIG. 17. As illustrated in FIG. 12, if the first switching element 280 is connected to the ground terminal 282 (S124) and the second switching element 290 is connected to the pulse signal reception terminal 291 (S125), the switching circuit 270 may transmit the signal W1 corresponding to an inversion waveform of the pulse signal received by the PCB 230 to the transducer element 211 (S130). According to the pulse inversion harmonic imaging scheme, the positive pulse signal and the negative pulse signal symmetrical to the positive pulse signal must be simultaneously and successively transmitted to the target object. Therefore, if the switching action of the switching circuit 270 is performed in a manner that the ultrasonic probe 200 transmits the negative pulse signal to the target object, the signal W2 corresponding to an inversion waveform of the positive pulse signal that is transmitted from the pulse transmitter and then received by the PCB 230, may be transmitted to the transducer element 211.

If the waveform of the pulse signal is modified in the switching circuit 270 and the resultant pulse signal having the modified waveform is applied to the transducer element 211, the ultrasonic probe 200 may transmit the ultrasonic signal to the target object (S140). In this case, if the signal W2 corresponding to an inversion waveform of the positive pulse signal received by the PCB 230 is applied to the transducer element 211, the ultrasonic probe 200 may transmit the ultrasonic signal that is transmitted from the pulse transmitter 700 and received by the PCB 230, to the target object (S126).

Operations of the switching circuit 270 for transmitting the signal from which the pulse signal received by the PCB 230 is removed are illustrated in FIGS. 18A to 18E, and the operations of FIGS. 18A to 18E are identical to those of FIGS. 13A to 13E.

Figure 18A:
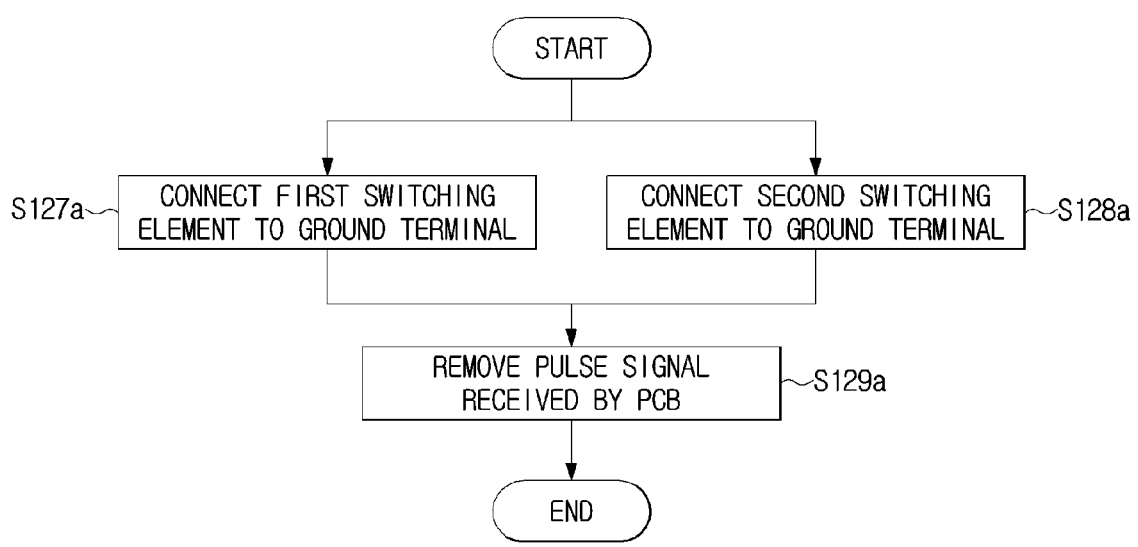
FIGS. 18A to 18E are flowcharts illustrating methods for controlling the switching circuit so as to transmit ultrasonic signals having a waveform from which the pulse signal received by the PCB is removed according to an embodiment of the present disclosure.

Referring to FIG. 18A, if the first switching element 280 is connected to the ground terminal 282 (S127a) and the second switching element 290 is connected to the ground terminal 292 (S128a), the switching circuit 270 may transmit the signal W3 from which the pulse signal received by the PCB 230 is removed (S129a) to the transducer element 211.

Figure 18B:
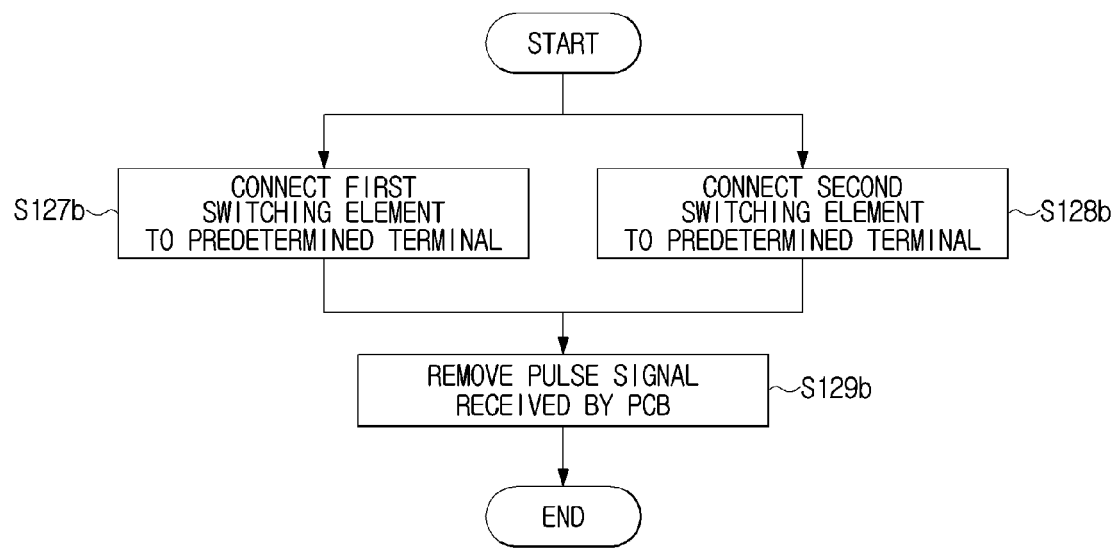

Referring to FIG. 18B, if the first switching element 280 is connected to the predetermined terminal 283 (S127b) and the second switching element 290 is connected to the predetermined terminal 293 (S128b), the signal W3 from which the pulse signal received by the PCB 230 of the switching circuit 270 is removed may be transmitted to the transducer element 211 (S130).

Figure 18C:
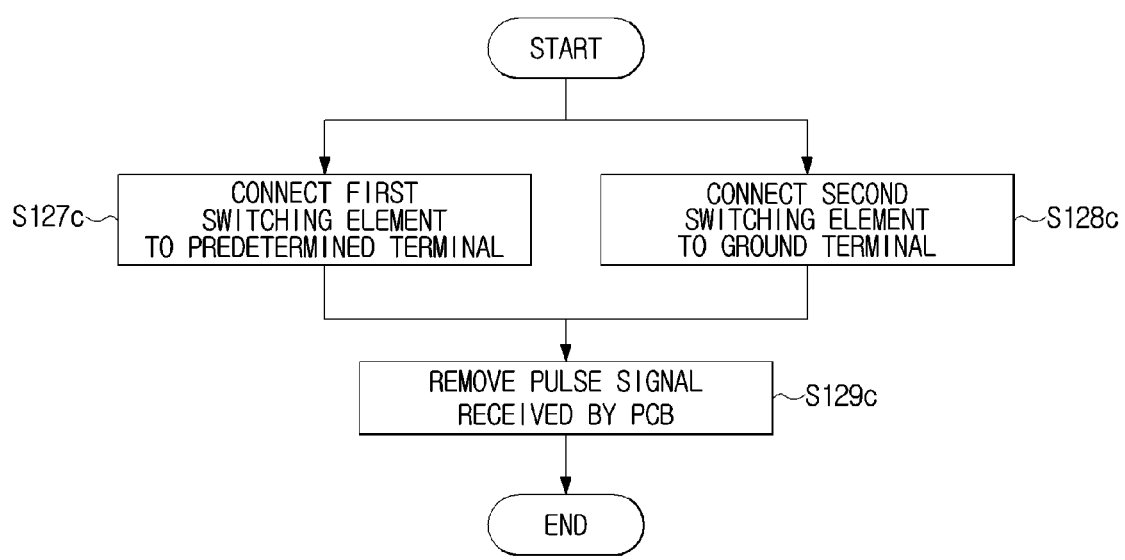

Referring to FIG. 18C, if the first switching element 280 is connected to the predetermined terminal 283 (S127c) and the second switching element 290 is connected to the ground terminal 292 (S128c), the signal W3 from which the pulse signal received by the PCB 230 of the switching circuit 270 is removed may be transmitted to the transducer element 211 (S130).

Figure 18D:
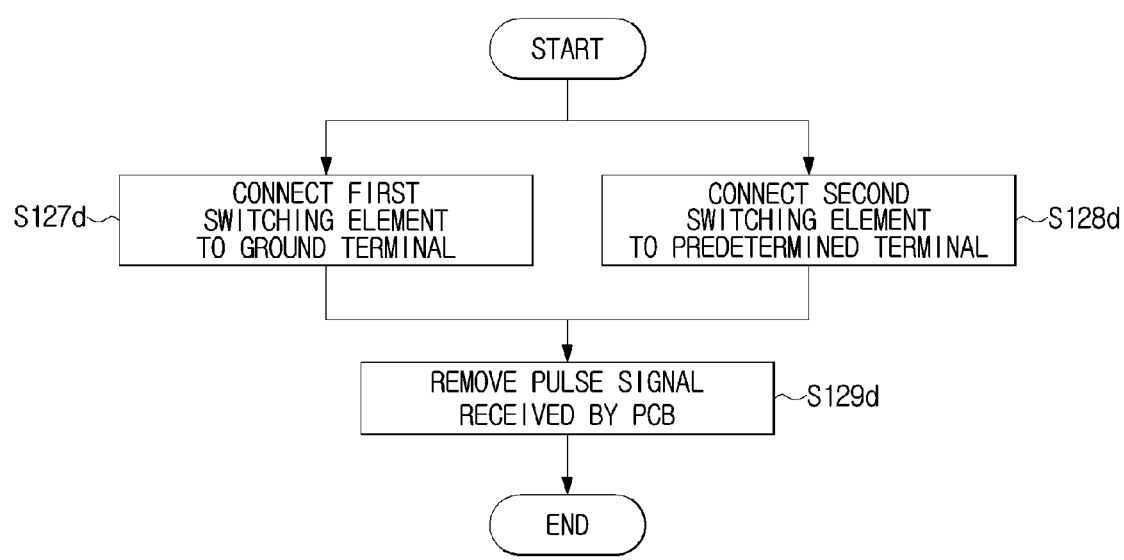

Referring to FIG. 18D, if the first switching element 280 is connected to the ground terminal 283 (S127d) and the second switching element 290 is connected to the predetermined terminal 293 (S128d), the signal W3 from which the pulse signal received by the PCB 230 of the switching circuit 270 is removed (S129d) may be transmitted to the transducer element 211 (S130).

Figure 18E:
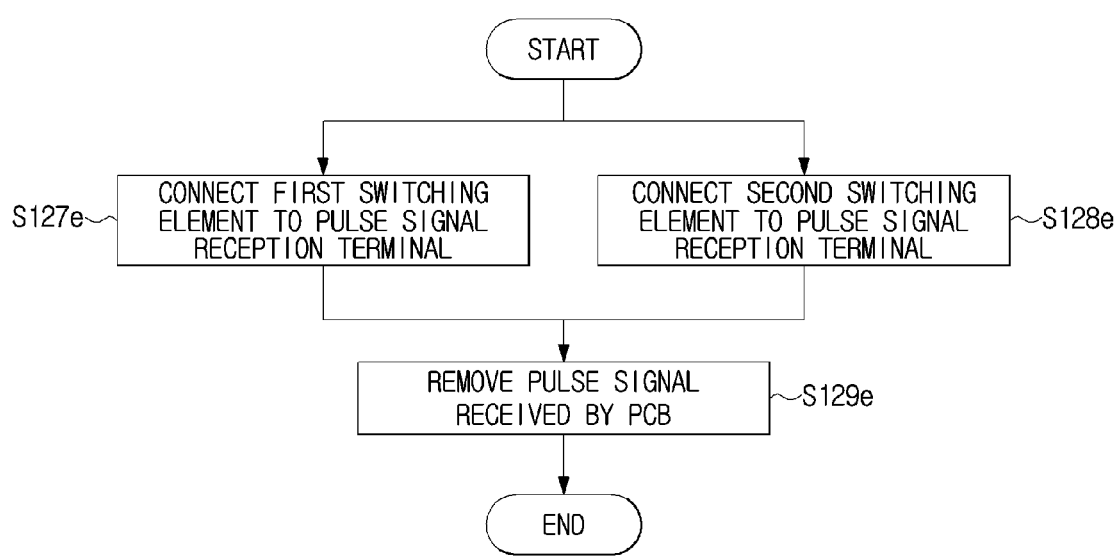

Referring to FIG. 18E, if the first switching element 280 is connected to the pulse signal reception terminal 281 (S127e) and the second switching element 290 is connected to the pulse signal reception terminal 291 (S128e), the signal W3 from which the pulse signal received by the PCB 230 of the switching circuit 270 is removed (S129e) may be transmitted to the transducer element 211 (S130).

As described above, the first switching element 280 and the second switching element 290 are controlled to block the pulse signal so that only the transducer element used for pulse signal transmission can be selectively used. If the abnormal signal occurs, the first switching element 280 and the second switching element 290 may block signal occurrence and may separate the signal from the user, resulting in improved user stability. That is, the transducer element not used for pulse signal transmission may be grounded such that resolution of the ultrasonic image can be improved. Furthermore, the transducer element is stabilized after transmission of the pulse signal, such that a simultaneous mode image can be improved in quality.

As described above, the ultrasonic signal transferred to the target object returns to the ultrasonic probe 200, the ultrasonic signal returned to the ultrasonic probe 200 may be transmitted to the ultrasonic receiver 800 of the main body of the ultrasonic imaging apparatus 100 (S150), and may be image-processed under the control of the processor 400, such that the processed image result may be displayed on the display 160.

Although not shown in the drawings, if the first switching element 280 and the second switching element 290 of the switching circuit 270 are connected to the pulse signal reception terminals (281, 291), the ground terminals (282, 292), and the predetermined terminals (283, 293) as illustrated in FIGS. 13A to 13E, the pulse signal transmitted from the pulse transmitter 700 to the PCB 230 is blocked or cut off at the connection time point, such that no ultrasonic signals may be transmitted.

In addition, as illustrated in FIG. 14, the switching circuits 270 respectively connected to the transducer elements 211 are controlled, such that the first switching element 280 and the second switching element 290 contained in the switching circuit 270 connected to the transducer element 211 configured not to transmit the ultrasonic signal may be respectively connected to the pulse signal reception terminals (281, 291), the ground terminals (282, 292), and the predetermined terminals (283, 293).

FIGS. 19A to 22 are conceptual diagrams illustrating exemplary methods for changing a time point at which the same waveform as the pulse signal received by the switching element is transmitted, a time point at which an inversion waveform of the pulse signal received by the switching element is transmitted, and a time point at which the signal from which the pulse signal is removed is transmitted.

If the first switching element 280 is connected to any one of the pulse signal reception terminal 281, the ground terminal 282, and the predetermined terminal 283, and if the second switching element 290 is connected to any one of the pulse signal reception terminal 291, the ground terminal 292, and the predetermined terminal 293, the positive pulse signal W1 scheduled to pass through the switching circuit 270 at the corresponding time may be output as the signal W3 from which the pulse signal is removed. Since the pulse signal is removed as described above, drooping or rolling of the pulse signal can be removed and stability of the target object can be improved. In addition, the transducer element 211 can be stabilized, and the transducer element 211 to be used for pulse signal transmission can be selectively used.

A specific time at which the first switching element 280 and the second switching element 290 are respectively connected to the pulse signal reception terminals (281, 291), the ground terminals (282, 292), or the predetermined terminals (283, 293) may be selected at random. In addition, a signal output time at which the signal W3 from which the pulse signal is removed is output may be changed according to such connection time.

That is, the specific time at which the first switching element 280 and the second switching element 290 are connected to the pulse signal reception terminals (281, 291), the ground terminals (282, 292), or the predetermined terminals (283, 293) may be selected at random, and a duration time of such connection state may also be determined at random.

Figure 19A:
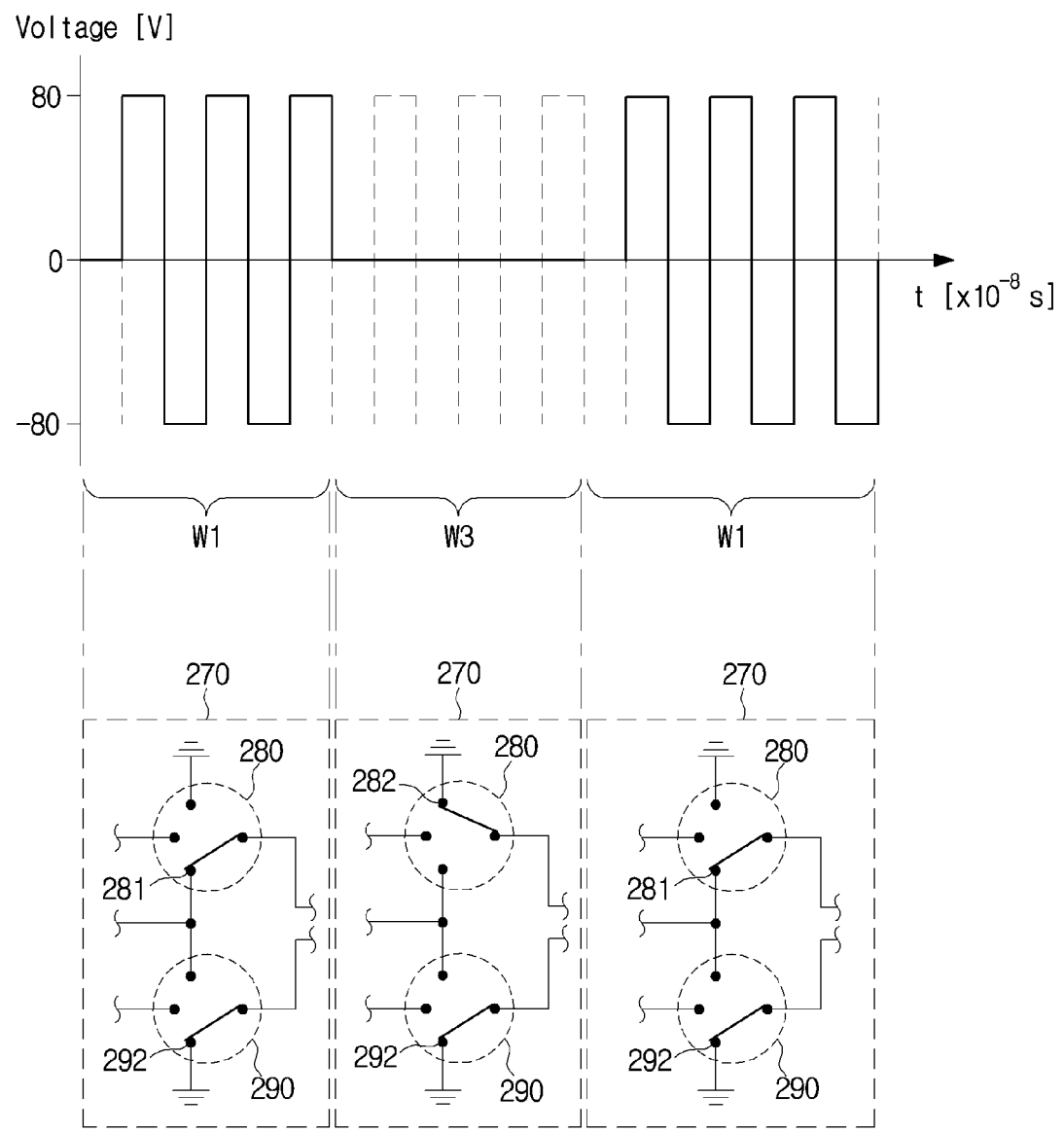
FIGS. 19A to 22 are conceptual diagrams illustrating exemplary methods for changing a time point at which the same waveform as the pulse signal received by the switching element is transmitted, a time point at which an inversion waveform of the pulse signal received by the switching element is transmitted, and a time point at which the signal from which the pulse signal is removed is transmitted.

Referring to FIG. 19A, assuming that the first switching element 280 is connected to the pulse signal reception terminal 281 and the second switching element 290 is connected to the ground terminal 292, the positive pulse signal W1 having passed through the switching circuit 270 may be output as the positive pulse signal W1 having the same waveform as the signal received by the switching circuit 270. That is, the positive pulse signal W1 having passed through the switching circuit 270 may be transferred to the target object through the transducer element 211.

While the positive pulse signal W1 having the same waveform as the signal received by the switching circuit 270 is output during a predetermined time, the first switching element 280 may be connected to the ground terminal 282, and the positive pulse signal W1 scheduled to pass through the switching circuit 270 for a predetermined time starting from a connection start time may be output as the other signal W3 from which the pulse signal is removed. The signal W3 from which the pulse signal is removed may also be output not only through the switching of FIG. 13A but also through the switching of FIGS. 13B to 13E.

After lapse of a predetermined time, the first switching element 280 may be re-connected to the pulse signal reception terminal 281, and the positive pulse signal W1 scheduled to pass through the switching circuit 270 for a predetermined time starting from the connection time may be output as the positive pulse signal W1 having the same waveform as the signal received by the switching circuit 270.

Figure 19B:
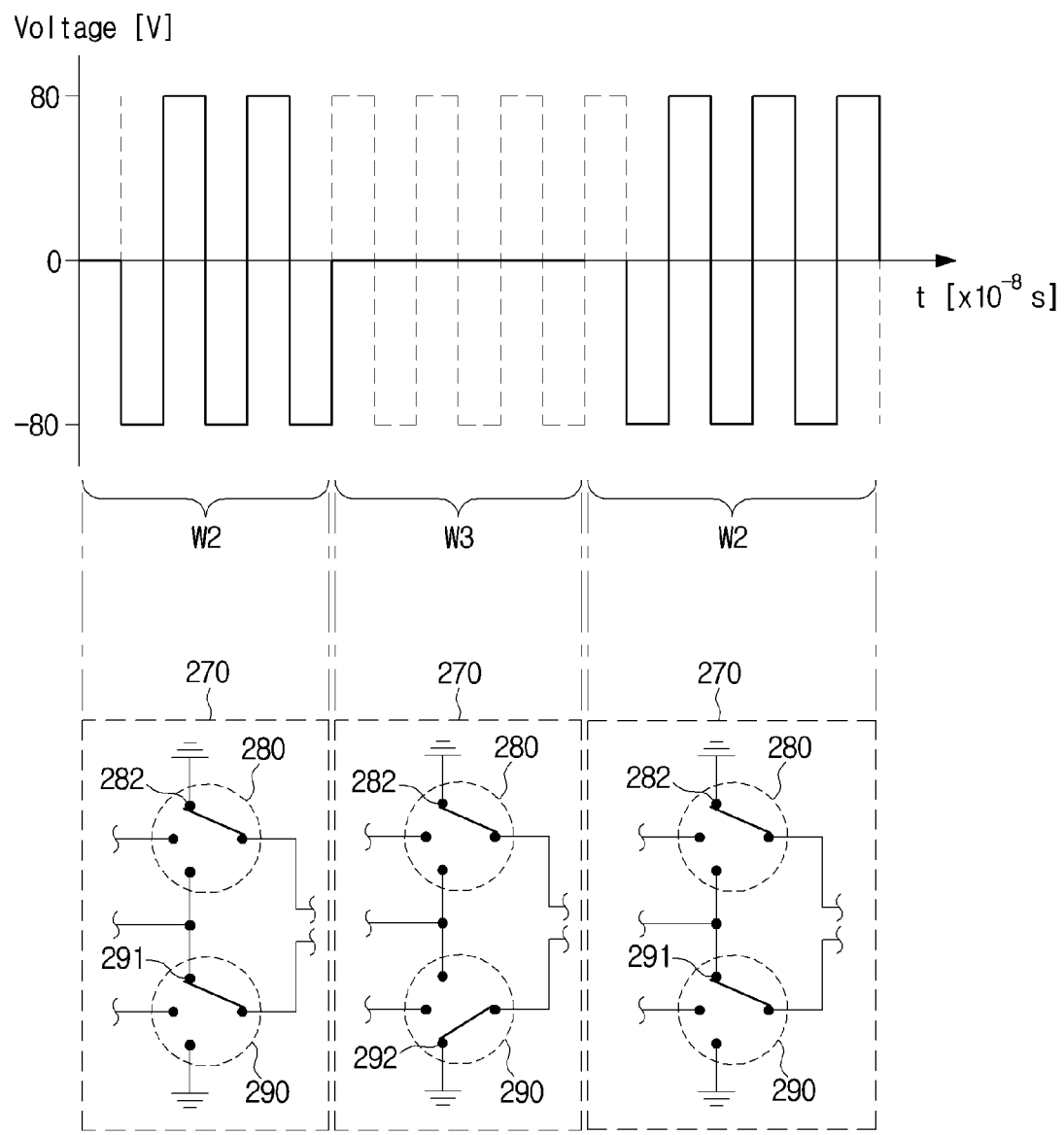

Referring to FIG. 19B, if the first switching element 280 is connected to the ground terminal 282 and the second switching element 290 is connected to the pulse signal reception terminal 291, the positive pulse signal W1 scheduled to pass through the switching circuit 270 may be output as the negative pulse signal W1 that is symmetrical to the signal received by the switching circuit 270 and has an inversion waveform of the received signal. In other words, the negative pulse signal W1 having passed through the switching circuit 270 may be transferred to the target object through the transducer element 211.

While the negative pulse signal W2 having an inversion waveform of the signal received by the switching circuit 270 is output during a predetermined time, the second switching element 290 may be connected to the ground terminal 292, and the positive pulse signal W1 scheduled to pass through the switching circuit 270 for a predetermined time starting from a connection start time may be output as the other signal W3 from which the pulse signal is removed. The signal W3 from which the pulse signal is removed may also be output not only through the switching of FIG. 13A but also through the switching of FIGS. 13B to 13E.

After lapse of a predetermined time, the second switching element 290 may be re-connected to the pulse signal reception terminal 291, and the positive pulse signal W1 scheduled to pass through the switching circuit 270 for a predetermined time starting from the connection time may be output as the negative pulse signal W2 that is symmetrical to the signal received by the switching circuit 270 and has an inversion waveform of the received signal.

The pulse signal is removed through the above-mentioned switching, such that drooping P1 or rolling P2 of the pulse signal can be prevented from occurring. If the drooping P1 or rolling P2 of the pulse signal is removed, resolution of the ultrasonic image may be increased and improved.

Figure 20A:
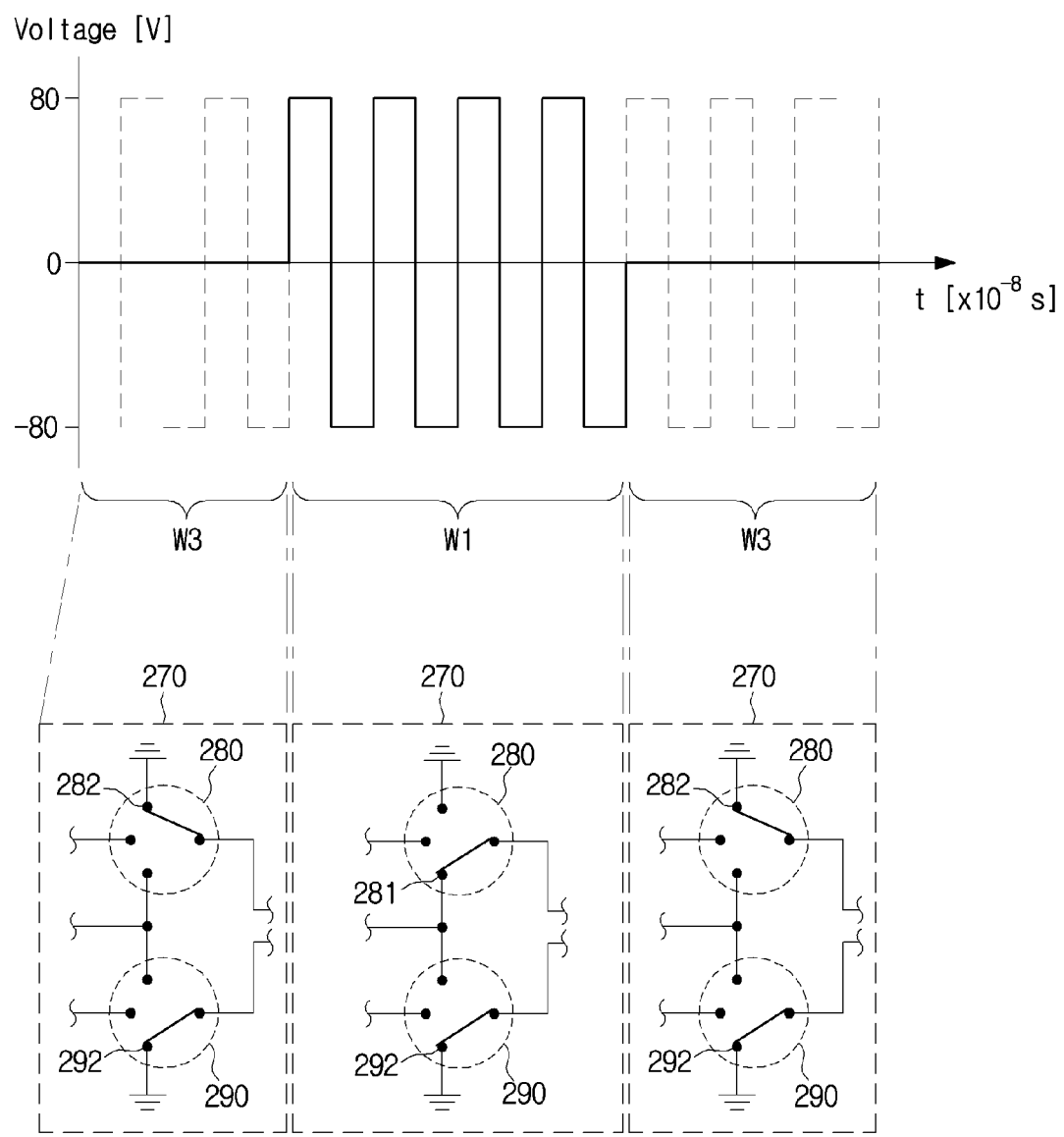

Referring to FIG. 20A, if the first switching element 280 is connected to the ground terminal 282 and the second switching element 290 is connected to the ground terminal 292, the positive pulse signal W1 scheduled to pass through the switching circuit 270 may be output as the signal W3 from which the pulse signal is removed. That is, the pulse signal may be zero at a specific time at which the first switching element 280 and the second switching element 290 are respectively connected to the ground terminal 282 and 292, such that the resultant signal having a zero value may be transmitted. The signal W3 from which the pulse signal is removed may be output not only through the switching of FIG. 13A but also through the switching of FIGS. 13B to 13E.

While the signal W3 from which the pulse signal received by the switching circuit 270 is removed is output during a predetermined time, the first switching element 280 may be connected to the pulse signal reception terminal 281, and may be output as the positive pulse signal W1 having the same waveform as the signal received by the switching circuit 270 during a predetermined time starting from the connection start time.

After lapse of a predetermined time, the first switching element 280 may be re-connected to the ground terminal 282, and the positive pulse signal W1 scheduled to pass through the switching circuit 270 for a predetermined time starting from the connection start time may be output as the signal W3 from which the pulse signal is removed.

Figure 20B:
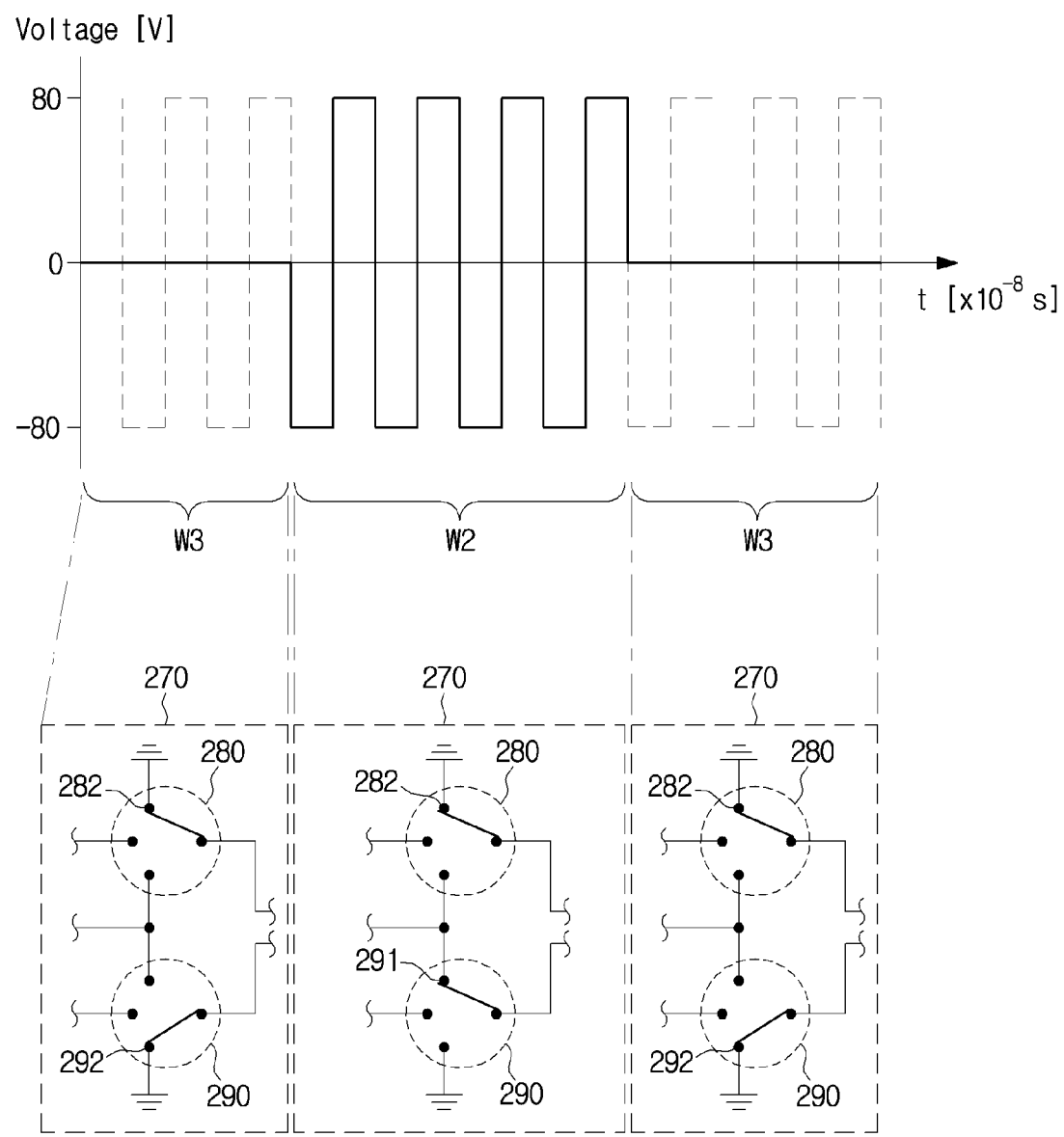

Referring to FIG. 20B, if the first switching element 280 and the second switching element 290 are respectively connected to the ground terminals 282 and 292, the positive pulse signal W1 scheduled to pass through the switching circuit 270 may be output as the signal W1 from which the pulse signal is removed. That is, the pulse signal may be zero at a specific time at which the first switching element 280 and the second switching element 290 are respectively connected to the ground terminal 282 and 292, such that the resultant signal having a zero value may be transmitted. The signal W3 from which the pulse signal is removed may be output not only through the switching of FIG. 13A but also through the switching of FIGS. 13B to 13E.

While the signal W3 from which the pulse signal received by the switching circuit 270 is removed is output during a predetermined time, the second switching element 290 may be connected to the pulse signal reception terminal 291, and may be output as the positive pulse signal W2 having the same waveform as the signal received by the switching circuit 270 during a predetermined time starting from the connection start time.

After lapse of a predetermined time, the second switching element 290 may be re-connected to the ground terminal 292, and the positive pulse signal W1 scheduled to pass through the switching circuit 270 for a predetermined time starting from the connection start time may be output as the signal W3 from which the pulse signal is removed.

That is, the residual voltage or residual current of the pulse signal is removed through the above-mentioned switching, such that the transducer element 211 can be stabilized and the simultaneous mode image can be improved.

Figure 21:
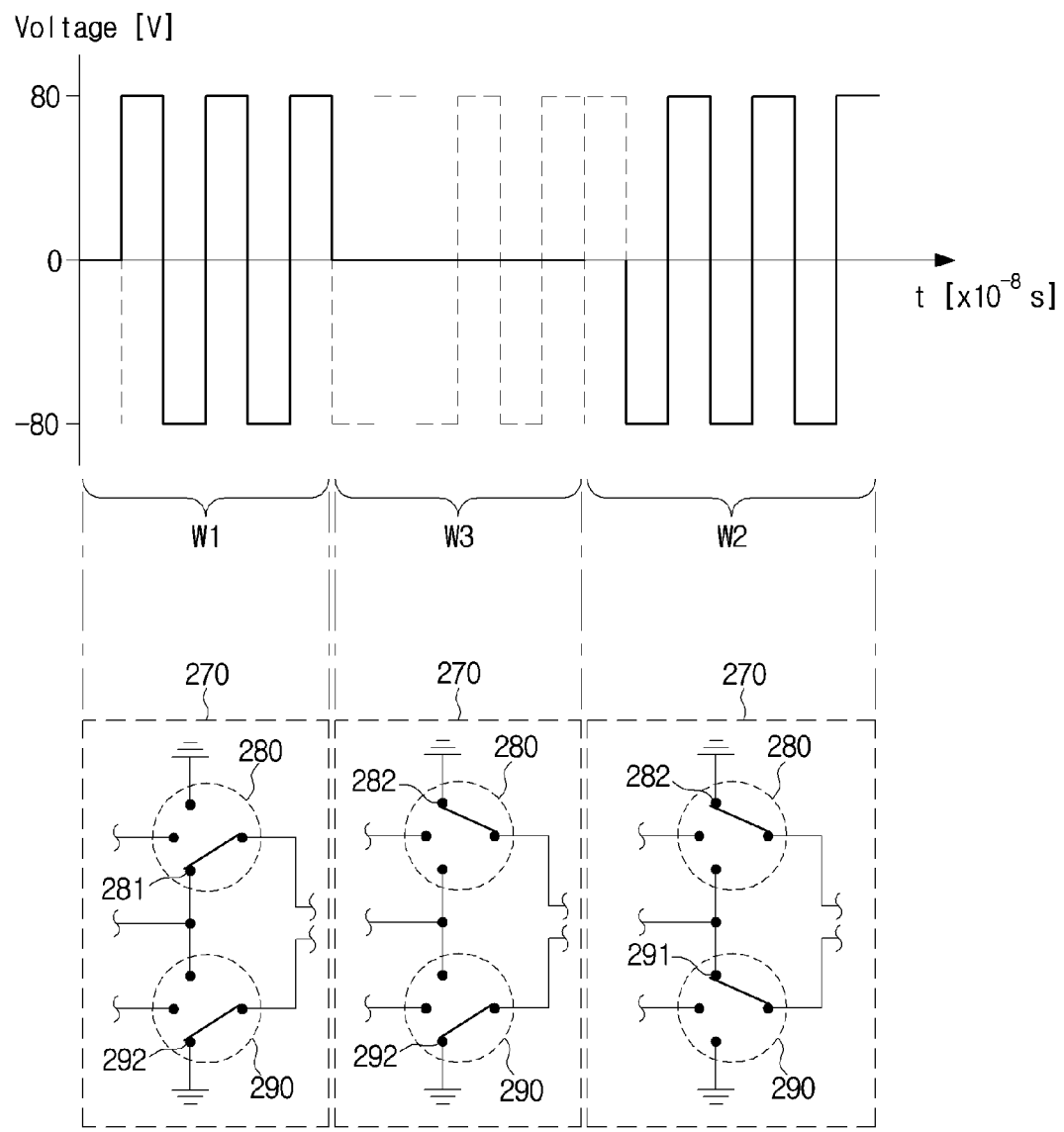

Referring to FIG. 21, if the first switching element 280 is connected to the pulse signal reception terminal 281 and the second switching element 290 is connected to the ground terminal 292, the positive pulse signal W1 having passed through the switching circuit 270 may be output as the positive pulse signal W1 having the same waveform as the signal received by the switching circuit 270. That is, the positive pulse signal W1 having passed through the switching circuit 270 may arrive at the target object through the transducer element 211.

While the positive pulse signal W1 having the same waveform as the signal received by the switching circuit 270 for a predetermined time, the first switching element 280 may be connected to the ground terminal 282, and the positive pulse signal W1 scheduled to pass through the switching circuit 270 for a predetermined time starting from the connection start time may be output as the signal W3 from which the pulse signal is removed. The signal W3 from which the pulse signal is removed may also be output not only through the switching of FIG. 13A but also through the switching of FIGS. 13B to 13E.

After lapse of a predetermined time, the second switching element 290 may be connected to the pulse signal reception terminal 291, and the positive pulse signal W1 scheduled to pass through the switching circuit 270 for a predetermined time starting from the connection time may be output as the positive pulse signal W2 that is symmetrical to the signal received by the switching circuit 270 and has an inversion waveform of the received signal.

The transducer elements not used in pulse signal Tx/Rx through the above-mentioned switching control may be grounded, resulting in improvement of resolution of the ultrasonic image.

Figure 22:
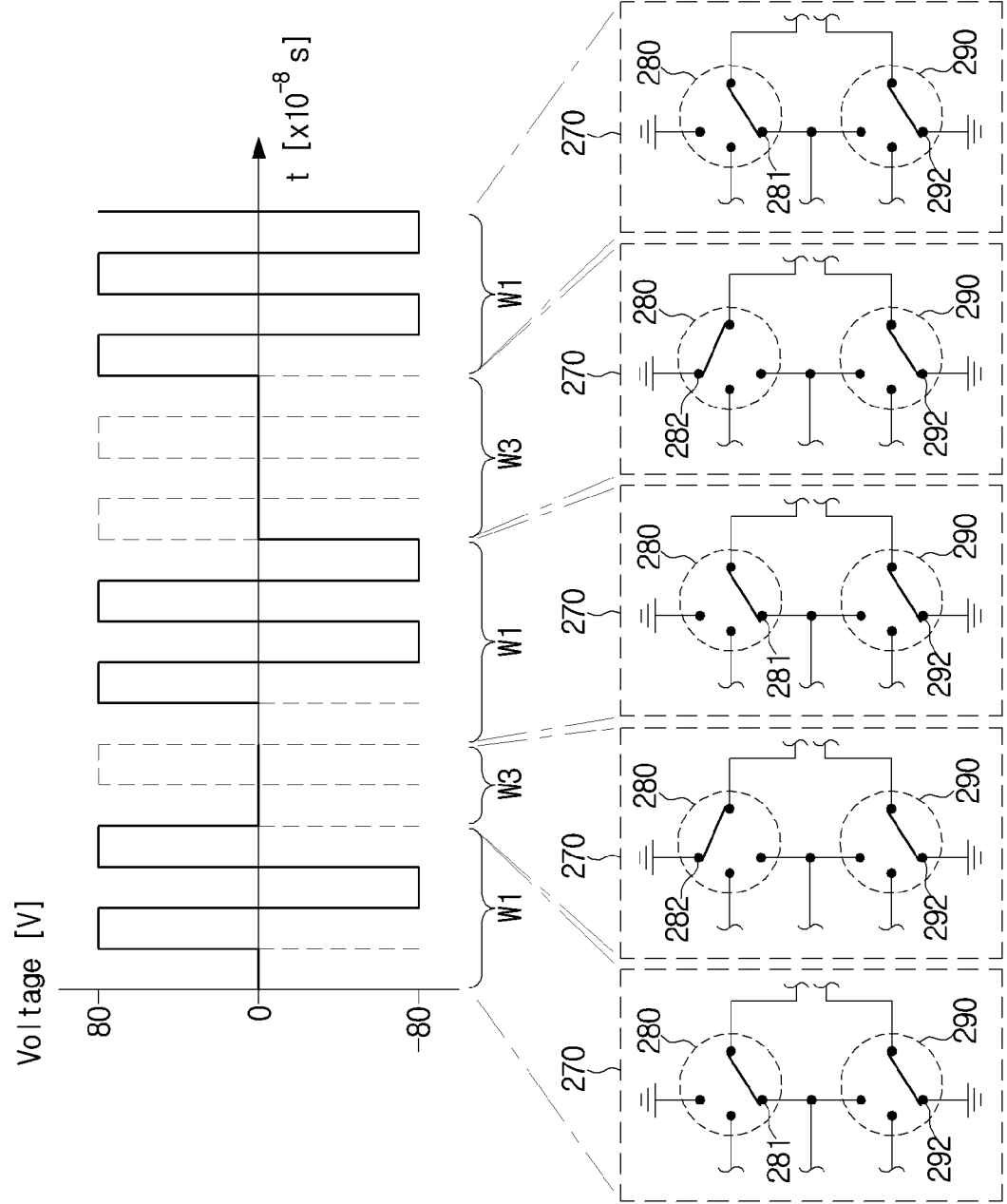

Referring to FIG. 22, the switching operation of FIG. 19A is repeatedly performed at intervals of a predetermined time, such that the positive pulse signal W1 scheduled to pass through the switching circuit 270 may be output as the positive pulse signal W1 having the same waveform as the signal received by the switching circuit 270 or may be output as the signal W3 having no pulse signal.

That is, as illustrated in FIGS. 19A to 22, the waveform of the positive pulse signal W1 scheduled to pass through the switching circuit 270 may be adjusted through switching of the first switching element 280 and the second switching element 290 contained in the switching circuit 270, and the waveform adjustment timing point of the positive pulse signal W1 may also be adjusted. Stability of the target object may be improved through the above-mentioned switching method. That is, assuming that the abnormal signal occurs in the ultrasonic or pulse signal received from the ultrasonic imaging apparatus 100 and it is impossible to control the ultrasonic imaging apparatus 100, if such signal arrives at the target object such as a human, there may be a high risk of damaging or hurting the target object, such that blocking of signals is needed. Therefore, if the above-mentioned abnormal signal is monitored, the abnormal signal may be prevented through the above-mentioned switching.

FIGS. 23A to 24B are conceptual diagrams illustrating a method for transmitting ultrasonic pulse signals through switching of a transmission (Tx) element and a method for receiving ultrasonic pulse signals through switching of a reception (Rx) element according to an embodiment of the present disclosure.

Ultrasonic diagnosis methods using the ultrasonic probe 200 are classified into a pulsed wave (PW) ultrasonic diagnosis method and a contiguous wave (CW) ultrasonic diagnosis method.

A transmission element and a reception element according to the PW method are identical to each other, and flow of a specific part of the target object may be measured using position information needed for ultrasonic diagnosis. In addition, the PW scheme is mainly utilized to perform low-speed blood flow measurement, and a maximum detectable flow speed is about 1 m/s.

Meanwhile, according to the CW method, the Tx element and the Rx element may be implemented as different elements, and it may be possible to obtain all kinds of information from the ultrasonic signals without using the position information needed for ultrasonic diagnosis.

That is, the ultrasonic system may transmit the ultrasonic signal to the target object using the ultrasonic probe 200 including at least one Tx element and at least one Rx element, and may receive the echo ultrasonic signal reflected from the target object using the same ultrasonic probe 200, resulting in formation of the digital signal. The ultrasonic system may extract the Doppler signal by processing the digital signal, and may form the CW (Continuous Wave) Doppler image using the extracted Doppler signal.

In addition, the CW method is mainly utilized for measurement of abnormal high-speed flow speed, and a maximum detectable flow speed is about 7 m/s.

Figure 23A:
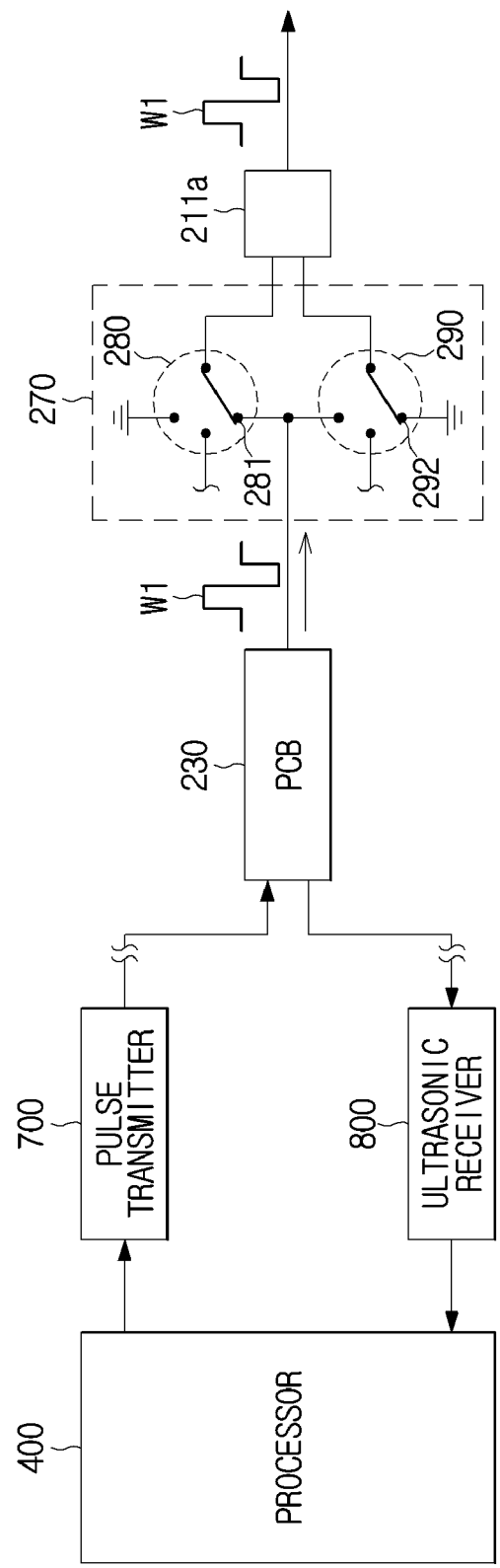
FIGS. 23A to 24B are conceptual diagrams illustrating a method for transmitting ultrasonic pulse signals through switching of a transmission (Tx) element and a method for receiving ultrasonic pulse signals through switching of a reception (Rx) element according to an embodiment of the present disclosure.

Referring to FIG. 23A, according to the CW ultrasonic signal transmission, the ultrasonic pulse signal may be transmitted through the above-mentioned switching of FIG. 11. That is, in order to transmit the ultrasonic pulse signal through the CW-based transmission (Tx) element 211a, the first switching element 280 may be connected to the pulse signal reception terminal 281, and the second switching element 290 may be connected to the ground terminal 292.

If the first switching element 280 is connected to the pulse signal reception terminal 281 and the second switching element 290 is connected to the ground terminal 292, the positive pulse signal W1 scheduled to pass through the switching circuit may be output as the positive pulse signal W1 having the same waveform as the signal received by the switching circuit 270. That is, the positive pulse signal W1 having passed through the switching circuit 270 may be transferred to the target object through the Tx element 211a.

Figure 23B:
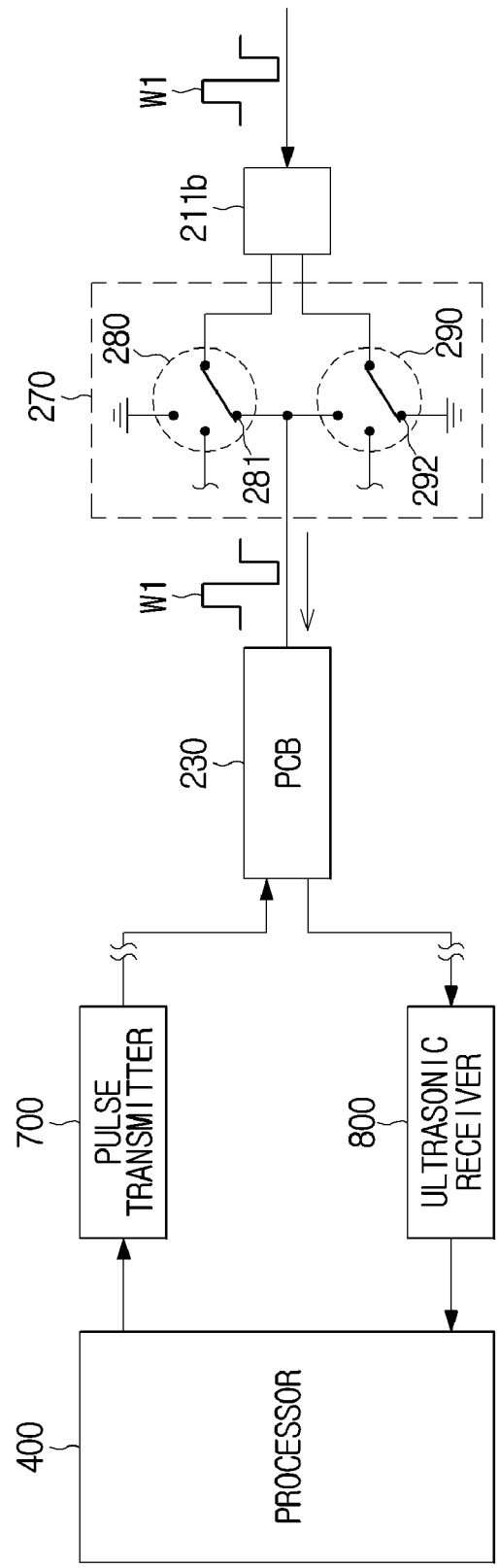

Referring to FIG. 23B, according to the CW-based ultrasonic signal transmission, the ultrasonic imaging apparatus may receive the ultrasonic pulse signal reflected from the target object through switching. That is, in order to receive the ultrasonic pulse signal reflected from the target object through the Rx element 211*b* according to the CW ultrasonic diagnosis method, the first switching element 280 may be connected to the pulse signal reception terminal 281 and the second switching element 290 may be connected to the ground terminal 292.

If the first switching element 280 is connected to the pulse signal reception terminal 281 and the second switching element 290 is connected to the ground terminal 292, the positive pulse signal W1 reflected from the target object may pass through the switching circuit 270 such that the positive pulse signal W1 may be transferred as another positive pulse signal W1 having the same waveform to the PCB 230. That is, the negative pulse signal W1 reflected from the target object may be transferred to the PCB 230 through the Rx element 211*b*.

Figure 24A:
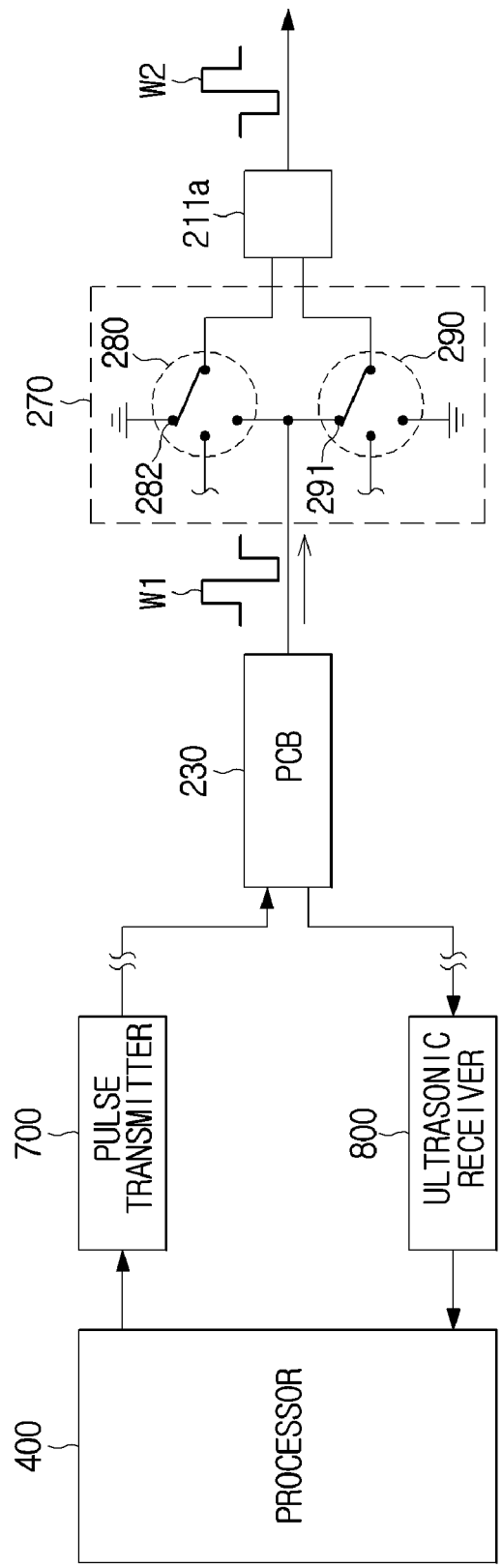

Referring to FIG. 24A, according to the CW-based ultrasonic signal transmission, the ultrasonic pulse signal may be transmitted through the above-mentioned switching of FIG. 12. That is, in order to transmit the ultrasonic pulse signal through the Tx element 211*a* using the CW method, the first switching element 280 may be connected to the ground terminal 282, and the second switching element may be connected to the pulse signal reception terminal 291.

If the first switching element 280 is connected to the ground terminal 83 and the second switching element 290 is connected to the pulse signal reception terminal 291, the positive pulse signal W1 scheduled to pass through the switching circuit 270 may be output as the negative pulse signal W1 that is symmetrical to the signal received by the switching circuit 270 and has an inversion waveform of the received signal. That is, the negative pulse signal W1 having passed through the switching circuit 270 may be transferred to the target object through the Tx element 211*a*.

Figure 24B:
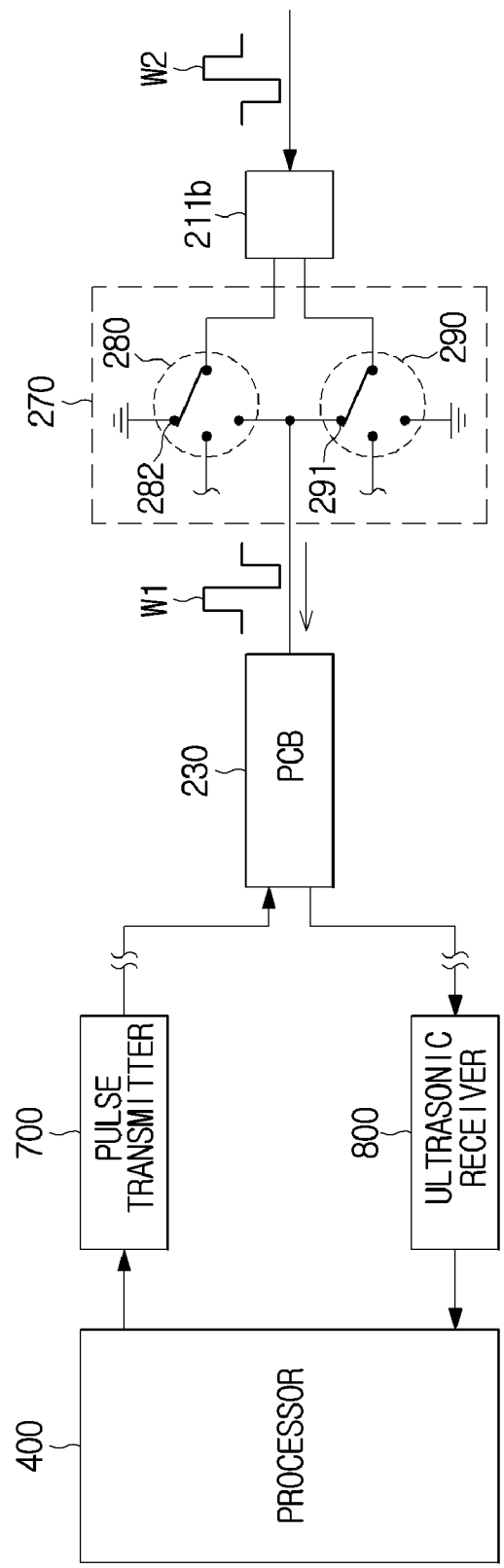

Referring to FIG. 24B, according to CW-based ultrasonic signal transmission, the ultrasonic imaging apparatus may receive the ultrasonic pulse signal reflected from the target object through switching as described above. In other words, in order to receive the ultrasonic pulse signal reflected from the target object through the Rx element 211*b* according to the CW method, the first switching element 280 may be connected to the ground terminal 282, and the second switching element 290 may be connected to the pulse signal reception terminal 291.

If the first switching element 280 is connected to the ground terminal 282 and the second switching element 290 is connected to the pulse signal reception terminal 291, the negative pulse signal W1 reflected from the target object may pass through the switching circuit 270 such that the negative pulse signal W1 may be output as the positive pulse signal W1 having an inversion waveform, and the resultant pulse signal W1 having the inversion waveform may arrive at the PCB 230. That is, the negative pulse signal W1 reflected from the target object may be transmitted to the PCB 230 through the Rx element 211*b*.

In addition to the above-mentioned switching methods of the switching circuit 270 illustrated in FIGS. 23*a* to 24*b*, various switching methods for the first switching element 280 and the second switching element 290 may be used in various ways. Detailed embodiments of the above-mentioned switching are identical to those of FIGS. 11 to 13E. That is, the waveform of the pulse signal that is transmitted to the target object through the Tx element 211*a* according to various switching methods may be modified, and the waveform of the pulse signal that is received by the Rx element 211*b* and then transmitted to the PCB 230 may also be modified.

According to the CW-based ultrasonic transmission/reception (Tx/Rx) method, the image of the ultrasonic image may be improved through the switching methods illustrated in FIGS. 13A to 13E.

That is, interference of the ultrasonic pulse signal can be removed through switching of the switching circuit 270 connected to the elements not used in transmission/reception (Tx/Rx) of the ultrasonic pulse signal from among the Tx element 211*a* and the Rx element 211*b*.

According to the CW method, transmission and reception of the ultrasonic pulse signal may be successively performed, and the Tx element 211*a* and the Rx element 211*b* may be arranged separately from each other. Therefore, if the ultrasonic pulse signal is successively transmitted through the Tx element 211*a*, interference of unused elements occurs such that the image quality of the ultrasonic image may be deteriorated. In order to address the above-mentioned issue, the switching operation of the switching circuit 270 for the Tx element not used in transmission of the ultrasonic pulse signal is controlled as shown in FIGS. 13A to 13E, resulting in improvement of the image quality of the ultrasonic image.

In addition, according to the CW method, the Tx element 211*a* and the Rx element 211*b* may be arranged separately from each other, and transmission and reception of the ultrasonic pulse signal are successively performed, such that a difference in frequency between the received ultrasonic signals is detected and blood flow information of the target object can be measured. In this case, when the blood flow information is monitored, the Tx/Rx focusing operation for a target site to be monitored is carried out. A maximum value of the Tx/Rx focusing delay according to the CW method may correspond to one cycle of the ultrasonic Tx signal.

Therefore, assuming that a maximum value of the Tx/Rx focusing delay is set to 480 ns (1 cycle), information corresponding to 480 ns must be contained in the corresponding signal for use in the ultrasonic imaging apparatus. In this case, if resolution is 16 nsc, the maximum number of expressible cases is 30.

However, although the maximum delay value is 240 ns when using the switching methods of FIGS. 11 and 12, the number of cases capable of expressing the same resolution as in 16 ns may be 15.

Since the ultrasonic pulse signal may be inverted in phase, only the maximum Tx/Rx delay value corresponding to a half cycle is needed. In contrast, assuming that the methods of FIGS. 11 to 12 are used on the condition that the number of cases of expressing the resolution is kept at 30, the resolution may be increased up to 8 ns.

The ultrasonic pulse signal reception may have the same number of delay cases in the same manner as in ultrasonic pulse signal transmission, image resolution may be doubled. In contrast, if the maximum delay value for the ultrasonic pulse signal reception is identical to that of the ultrasonic pulse signal transmission, the number of delay cases may be halved.

According to the CW-based ultrasonic signal transmission/reception scheme, the pulse signal transmitted/received by the ultrasonic probe is inverted by controlling the switching elements mounted to the ultrasonic probe, such that the residual signal occurrence caused by reception of the asymmetrical inversion signal is removed, resulting in improvement of the image resolution. In addition, the pulse signal is blocked by controlling the switching element, such that only the transducer elements used in pulse transmission/reception (Tx/Rx) may be selectively used. Since occurrence of the abnormal signal is blocked, user stability can be improved.

In addition, the transducer element not used in pulse transmission/reception (Tx/Rx) is grounded, resulting in resolution improvement of the ultrasonic image. Furthermore, after transmission of the pulse signal, the transducer element is stabilized so that the simultaneous mode image is improved in quality.

As is apparent from the above description, according to pulse inversion harmonic imaging, a waveform of a pulse signal transmitted from the ultrasonic imaging apparatus is symmetrically inverted and transmitted by a switching circuit of the ultrasonic probe, the residual signal caused by reception of an asymmetrical inversion signal may not occur. The switching circuit of the ultrasonic probe improves symmetry of the pulse signals by manipulating the switching element, such that the degree of freedom in FET characteristics regarding either a symmetrical width of additional pulse signals or symmetry of the pulse signals can be improved. In addition, the ultrasonic imaging apparatus need not use a transmitter configured to transmit an inversion pulse signal, resulting in a simplified system structure. Extension or stretching of pulse signals can be prevented by controlling the switching circuit of the ultrasonic probe. Furthermore, the plurality of transducer arrays may be selectively used to transmit and receive such pulse signals, resulting in improvement of user stability.

The above-mentioned embodiments have exemplarily disclosed the ultrasonic probe, the ultrasonic imaging apparatus including the same, and the method for controlling the ultrasonic imaging apparatus with reference to the attached drawings, the scope or spirit of the present disclosure is not limited thereto, and the above-mentioned embodiments are merely exemplary in all technical aspects. Although the above-mentioned embodiments of the present disclosure have been disclosed herein merely for illustrative purposes, the scope or spirit of the embodiments is not limited thereto, and those skilled in the art will appreciate that various modifications, additions and substitutions are possible, without departing from the scope and spirit of the disclosure as disclosed in the accompanying claims. For example, adequate effects of the present disclosure may be achieved even if the foregoing processes and methods may be carried out in different order than described above, and/or the aforementioned elements, such as systems, structures, devices, or circuits, may be combined or coupled in different forms and modes than as described above or be substituted or switched with other components or equivalents.

Although a few embodiments of the present disclosure have been shown and described, it would be appreciated by those skilled in the art that changes may be made in these embodiments without departing from the principles and spirit of the invention, the scope of which is defined in the claims and their equivalents.

What is claimed is:

1. An ultrasonic probe comprising:
   a transducer array configured to transmit and receive an ultrasonic signal;
   a printed circuit board (PCB) electrically connected to the transducer array to transmit a pulse signal, which is received from a main body of an ultrasonic imaging apparatus, to the transducer array; and
   a switching circuit configured to change a waveform of the pulse signal, which is received from the main body of the ultrasonic imaging apparatus and transmitted from the PCB to the transducer array,
   wherein the switching circuit includes a first switching element and a second switching element,
   wherein the transducer array includes a transducer element directly connected to the first switching element by a first signal line and directly connected to the second switching element by a second signal line,
   wherein the first switching element and the second switching element each includes a pulse signal reception terminal and a ground terminal,
   wherein the transducer element is connected to the pulse signal reception terminal or the ground terminal of the first switching element through the first signal line, and
   wherein the transducer element is connected to the pulse signal reception terminal or the ground terminal of the second switching element through the second signal line.

2. The ultrasonic probe according to claim 1,
   wherein the first switching element is configured to connect the transducer element to any one of the pulse signal reception terminal, the ground terminal, and a predetermined terminal through the first signal line, and the second switching element is configured to connect the transducer element to any one of the pulse signal reception terminal, the ground terminal, and a predetermined terminal through the second signal line.

3. The ultrasonic probe according to claim 1, wherein:
   the transducer array includes a plurality of transducer elements; and
   wherein the switching circuit includes a plurality of switching circuits corresponding to respective transducer elements.

4. The ultrasonic probe according to claim 3, wherein:
   when the first switching element is connected to the pulse signal reception terminal and the second switching element is connected to the ground terminal, one of the plurality of transducer elements transmits an ultrasonic signal having the same waveform as the pulse signal, which is received from the main body of the ultrasonic imaging apparatus and transmitted from received by the PCB to the transducer array.

5. The ultrasonic probe according to claim 3, wherein:
   when the first switching element is connected to the ground terminal and the second switching element is connected to the pulse signal reception terminal, one of the plurality of transducer elements receives an ultrasonic signal corresponding to an inversion waveform of the pulse signal, which is received from the main body of the ultrasonic imaging apparatus and transmitted from the PCB to the transducer array.

6. The ultrasonic probe according to claim 3, wherein one of the plurality of transducer elements transmits no ultrasonic signal when each of the first switching element and the second switching element are connected to the pulse signal reception terminal, the ground terminal, and the predetermined terminal.

7. The ultrasonic probe according to claim 6, wherein:
   one of the plurality of switching elements, in which each of the first switching element and the second switching element is connected to any one of the pulse signal reception terminal, the ground terminal, and the predetermined terminal, is configured to prevent the pulse signal, which is received from the main body of the ultrasonic imaging apparatus and transmitted from the PCB to the transducer array, from being applied to the transducer element that transmits no ultrasonic signal.

8. The ultrasonic probe according to claim 2, further comprising:
   a control board configured to control the first switching element to be connected to the pulse signal reception terminal, the ground terminal, or the predetermined terminal, and configured to control the second switching element to be connected to the pulse signal reception terminal, the ground terminal, or the predetermined terminal.

9. The ultrasonic probe according to claim 1, wherein the printed circuit board (PCB) is configured to transmit a pulse signal received from the transducer array to the main body of the ultrasonic imaging apparatus.

10. An ultrasonic imaging apparatus comprising:
a pulse transmitter configured to generate a pulse signal and transmit the generated pulse signal;
an ultrasonic probe which includes
a printed circuit board (PCB) electrically connected to a transducer array to transmit the pulse signal, which is generated and transmitted from the pulse transmitter, to the transducer array, and
a switching circuit configured to change a waveform of the pulse signal transmitted from the PCB to the transducer array; and
a processor configured to control the switching circuit for changing a waveform of the pulse signal which is transmitted from the PCB to the transducer array,
wherein the ultrasonic probe includes a switching circuit comprising a first switching element and a second switching element,
wherein the transducer array includes a transducer element directly connected to the first switching element by a first signal line and directly connected to the second switching element by a second signal line,
wherein the first switching element and the second switching element each includes a pulse signal reception terminal and a ground terminal,
wherein the transducer element is connected to the pulse signal reception terminal or the ground terminal of the first switching element through the first signal line, and
wherein the transducer element is connected to the pulse signal reception terminal or the ground terminal of the second switching element through the second signal line.

11. The ultrasonic imaging apparatus according to claim 10,
wherein the first switching element is configured to connect the transducer element to any one of the pulse signal reception terminal, the ground terminal, and a predetermined terminal through the first signal line, and the second switching element is configured to connect to any one of the pulse signal reception terminal, the ground terminal, and a predetermined terminal through the second signal line.

12. The ultrasonic imaging apparatus according to claim 10, wherein:
the transducer array includes a plurality of transducer elements; and
the switching circuit is provided in plural to correspond to respective transducer elements.

13. The ultrasonic imaging apparatus according to claim 12, wherein:
the processor connects the first switching element to the pulse signal reception terminal, connects the second switching element to the ground terminal, and thus controls transmission of an ultrasonic signal having the same waveform as the pulse signal transmitted from the PCB to the transducer array.

14. The ultrasonic imaging apparatus according to claim 12, wherein:
the processor connects the first switching element to the ground terminal, connects the second switching element to the pulse signal reception terminal, and thus controls transmission of an ultrasonic signal having an inversion waveform of the pulse signal received by the pulse signal transmitted from the PCB to the transducer array.

15. The ultrasonic imaging apparatus according to claim 12, wherein the processor connects each of the first switching element and the second switching element to any one of the pulse signal reception terminal, the ground terminal, and the predetermined terminal, such that no ultrasonic signal is transmitted.

16. The ultrasonic imaging apparatus according to claim 15, wherein:
one of the plurality of switching elements, in which each of the first switching element and the second switching element is connected to any one of the pulse signal reception terminal, the ground terminal, and the predetermined terminal, is configured to prevent the pulse signal pulse signal, which is transmitted from the PCB to the transducer array, from being applied to one of the plurality of transducer elements.

17. The ultrasonic imaging apparatus according to claim 10, wherein the printed circuit board (PCB) is configured to transmit the pulse signal received from the transducer array to a main body of the ultrasonic imaging apparatus.

18. A method for controlling an ultrasonic imaging apparatus equipped with an ultrasonic probe including a transducer array and a switching circuit comprising a first switching element and a second switching element which are directly connected to the transducer array, and each of the first and second switching elements include a pulse signal reception terminal and a ground terminal, the method comprising:
connecting the transducer array to the pulse signal reception terminal or the ground terminal of the first switching element;
connecting the transducer array to the pulse signal reception terminal or a ground terminal of the second switching element;
transmitting a pulse signal to the ultrasonic probe; and
changing a waveform of the pulse signal received by the ultrasonic probe.

19. An ultrasonic probe comprising:
a transducer transmission element configured to transmit an ultrasonic signal to an object;
a transducer reception element configured to receive the ultrasonic signal from the object;
a printed circuit board (PCB) electrically connected to the transducer transmission element and the transducer reception element, configured to transmit a pulse signal received from a main body of an ultrasonic imaging apparatus to the transducer transmission element, and configured to transmit a pulse signal received from the transducer reception element to the main body of the ultrasonic imaging apparatus; and
a switching circuit configured to change not only a waveform of the pulse signal transmitted from the PCB to the transducer transmission element, but also a waveform of the pulse signal received by the transducer reception element and transmitted to the PCB,
wherein the switching circuit includes a first switching element and a second switching element,
wherein the transducer transmission element or the transducer reception element is directly connected to the first switching element by a first signal line and directly connected to the second switching element by a second signal line, the first switching element and the second switching element each includes a pulse signal reception terminal and a ground terminal, the transducer element is connected to the pulse signal reception terminal or the ground terminal of the first switching element through the first signal line, and the transducer element is connected to the pulse signal reception terminal or the ground terminal of the second switching element through the second signal line.

20. The ultrasonic probe according to claim 19, wherein the first switching element is configured to connect the transducer transmission element or the transducer reception element to any one of the pulse signal reception terminal, the ground terminal, and a predetermined terminal through the first signal line, and the second switching element is configured to connect the transducer transmission element or the transducer reception element to any one of the pulse signal reception terminal, the ground terminal, and a predetermined terminal through the second signal line.

* * * * *